US012188052B2

(12) United States Patent
Cerutti et al.

(10) Patent No.: US 12,188,052 B2
(45) Date of Patent: *Jan. 7, 2025

(54) BACULOVIRUS EXPRESSION SYSTEM

(71) Applicants: CENTRE NATIONAL DE LA RECHERCHE SCIENTIFIQUE (CNRS), Paris (FR); INSTITUT NATIONAL DE LA RECHERCHE AGRONOMIQUE, Paris (FR)

(72) Inventors: Martine Cerutti, Saint Christol les Ales (FR); Sylvie Juliant, Saint Christol les Ales (FR); Coralie Bernon, Boisset-et-Gaujac (FR)

(73) Assignees: CENTRE NATIONAL DE LA RECHERCHE SCIENTIFIQUE (CNRS), Paris (FR); INSTITUT NATIONAL DE LA RECHERCHE AGRONOMIQUE, Paris (FR)

( * ) Notice: Subject to any disclaimer, the term of this patent is extended or adjusted under 35 U.S.C. 154(b) by 561 days.

This patent is subject to a terminal disclaimer.

(21) Appl. No.: 16/758,811

(22) PCT Filed: Oct. 25, 2018

(86) PCT No.: PCT/FR2018/052652
§ 371 (c)(1),
(2) Date: Apr. 23, 2020

(87) PCT Pub. No.: WO2019/081858
PCT Pub. Date: May 2, 2019

(65) Prior Publication Data
US 2020/0263144 A1    Aug. 20, 2020

(30) Foreign Application Priority Data

Oct. 25, 2017 (FR) ...................... 1760068

(51) Int. Cl.
*C12N 7/00* (2006.01)
*C12N 15/86* (2006.01)
*C12P 21/00* (2006.01)

(52) U.S. Cl.
CPC .............. *C12N 7/00* (2013.01); *C12N 15/86* (2013.01); *C12P 21/00* (2013.01); *C12N 2710/14043* (2013.01); *C12N 2710/14051* (2013.01)

(58) Field of Classification Search
None
See application file for complete search history.

(56) References Cited

U.S. PATENT DOCUMENTS 9,212,374 B2   12/2015   Roy et al.
2023/0063208 A1   3/2023   Cerutti et al.

FOREIGN PATENT DOCUMENTS

WO    01/12829 A2    2/2001
WO    2010/055292 A2    5/2010
WO    2013/005194 A2    1/2013
WO    2018/024998 A1    2/2018

OTHER PUBLICATIONS

Noad et al. BMC Molecular Biol 10, 87 (2009). https://doi.org/10.1186/1471-2199-10-87.*
Kost et al. Nature Biotechnology, vol. 23, No. 5, pp. 567-575, 2005.*
Cerutti et al mAbs, 4:3, 294-309, 2012.*
Juliant et al. Methods Mol Biol 2013;988:59-77.*
Palmberger D, Wilson IB, Berger I, Grabherr R, Rendic D. SweetBac: a new approach for the production of mammalianised glycoproteins in insect cells. PLoS One. 2012;7(4):e34226.
Chang GD, Chen CJ, Lin CY, Chen HC, Chen H. Improvement of glycosylation in insect cells with mammalian glycosyltransferases. J Biotechnol. Apr. 10, 2003;102(1):61-71.
Possee RD, Hitchman RB, Richards KS, Mann SG, Siaterli E, Nixon CP, Irving H, Assenberg R, Alderton D, Owens RJ, King LA. Generation of baculovirus vectors for the high-throughput production of proteins in insect cells. Biotechnol Bioeng. Dec. 15, 2008;101(6):1115-22.
Tan J, D'Agostaro AF, Bendiak B, Reck F, Sarkar M, Squire JA, Leong P, Schachter H. The human UDP-N-acetylglucosamine:alpha-6-D-mannoside-beta-1,2-N-acetylglucosaminyltransferase II gene (MGAT2). Cloning of genomic DNA, localization to chromosome 14q21, expression in insect cells and purification of the recombinant protein. Eur J Biochem. Jul. 15, 1995;231(2):317-28.
D'Agostaro G, Bendiak B, Tropak M. Cloning of cDNA encoding the membrane-bound form of bovine beta 1,4-galactosyltransferase. Eur J Biochem. Jul. 15, 1989;183(1):211-7.
Munster AK, Eckhardt M, Potvin B, Mühlenhoff M, Stanley P, Gerardy-Schahn R. Mammalian cytidine 5'-monophosphate N-acetylneuraminic acid synthetase: a nuclear protein with evolutionarily conserved structural motifs. Proc Natl Acad Sci U S A. Aug. 4, 1998;95(16):9140-5.
Lawrence SM, Huddleston KA, Pitts LR, Nguyen N, Lee YC, Vann WF, Coleman TA, Betenbaugh MJ. Cloning and expression of the human N-acetylneuraminic acid phosphate synthase gene with 2-keto-3-deoxy-D-glycero-D-galacto-nononic acid biosynthetic ability. J Biol Chem. Jun. 9, 2000;275(23):17869-77.
Kitagawa H, Paulson JC. Cloning of a novel alpha 2,3-sialyltransferase that sialylates glycoprotein and glycolipid carbohydrate groups. J Biol Chem. Jan. 14, 1994;269(2):1394-401.
Grundmann U, Nerlich C, Rein T, Zettlmeissl G. Complete cDNA sequence encoding human beta-galactoside alpha-2,6-sialyltransferase. Nucleic Acids Res. Feb. 11, 1990;18(3):667.

(Continued)

*Primary Examiner* — Oluwatosin A Ogunbiyi
(74) *Attorney, Agent, or Firm* — Arrigo, Lee, Guttman & Mouta-Bellum, LLP; Carla Mouta-Bellum

(57) ABSTRACT

Method for preparing, in an insect cell, a recombinant baculovirus comprising one or more transgene(s) each encoding a protein maturation enzyme and n transgenes each encoding a polypeptide of interest, by homologous recombination between a replication deficient baculovirus genome which comprises one or more transgene(s) each encoding a protein maturation enzyme and n transfer vectors each comprising one of the n transgenes each encoding a polypeptide of interest, n being an integer at least equal to 2.

24 Claims, 18 Drawing Sheets

Figure 1:
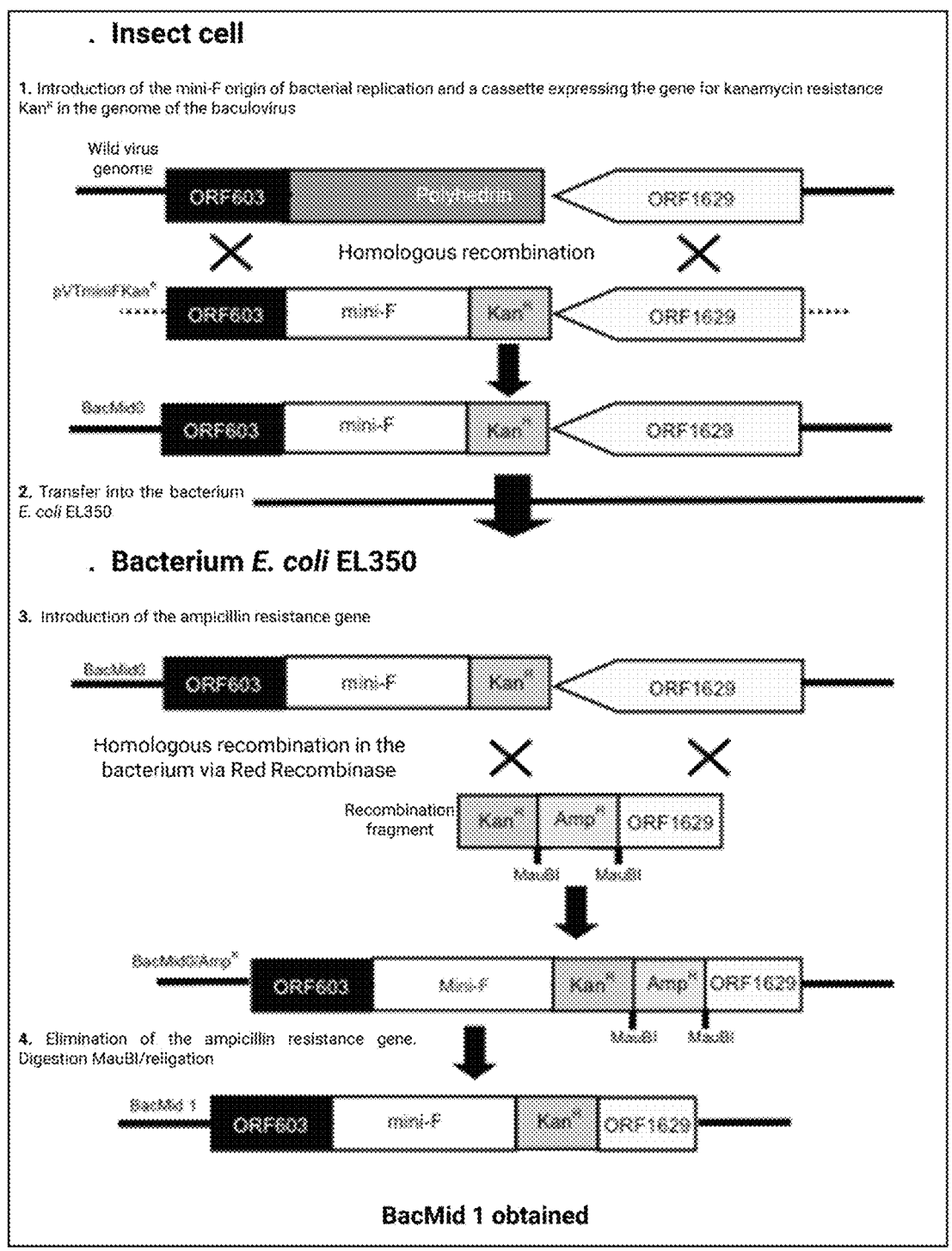

Specification includes a Sequence Listing.

(56) References Cited

OTHER PUBLICATIONS

Cieplik M, Klenk HD, Garten W. Identification and characterization of spodoptera frugiperda furin: a thermostable subtilisin-like endopeptidase. Biol Chem. Dec. 1998;379(12):1433-40.
Juliant S, Lévěque M, Cérutti P, Ozil A, Choblet S, Violet ML, Slomianny MC, Harduin-Lepers A, Cérutti M. Engineering the baculovirus genome to produce galactosylated antibodies in lepidopteran cells. Methods Mol Biol. 2013;988:59-77.
Jarvis DL, Finn EE. Biochemical analysis of the N-glycosylation pathway in baculovirus-infected lepidopteran insect cells. Virology. Oct. 1, 1995;212(2):500-11.
Ribeiro JP, Pau W, Pifferi C, Renaudet O, Varrot A, Mahal LK, Imberty A. Characterization of a high-affinity sialic acid-specific CBM40 from Clostridium perfringens and engineering of a divalent form. Biochem J. Jul. 15, 2016;473(14):2109-18.
Poul M-A et al, "Design of cassette baculovirus vectors for the productoin of therapeutic antibodies in insect cells," Immunotechnology, vol. 1(3), pp. 189-196, 1995.
Lakshmi S Vijayachandran et al, "Gene gymnastics," Bioengineered, vol. 4(5), pp. 279-287, 2013.
Yuta Kanai et al., Multiple large foreign protein expression by a single recombinant baculovirus: A system for production of multivalent vaccines, Protein Expression and Purification, vol. 91(1), 77-84, 2013.
D.L. Jarvis et al, "Novel Baculovirus Expression Vectors That Provide Sialylation of Recombinant Glycoproteins in Lepidopteran Insect Cells," Journal of Virology, vol. 75(13), pp. 6223-6227, 2001.
Je, Y.H. et al., "Generation of Baculovirus Expression Vector Defective Autographa californica Nuclear Polyhydrosis Virus Genome Maintained in *Eschcheria coli* for Occ+ Virus Production" Int. J. Indust. Entomol. vol. 2, No. 2, 2001, pp. 155-160.
St. Angelo, Carol et al., "Two of the Three Influenza Viral Polymerase Proteins Expressed by Using Baculovirus Vectors Form a Complex in Insect Cells", Journal of Virology, Feb. 1987, pp. 361-365.
Van Oers, Monique M., "Opportunities and challenges for the baculovirus expression system", Journal of Invertebrate Pathology, 107, (2011) S3-S15.
Gay et al., "Insertion of transposon Tn7 into the *Escherichia coli* glmS transcriptional terminator," Biochem J., 234:111-117 (1986).
Drocourt et al., "Chemical synthesis and biological activities of analogues of 2',5'-oligoadenylates containing 8-substituted adenosine derivatives," Nucleic Acids Research, 18(13):4439-4446 (1990).
Gentz et al., "Promoters Recognized by *Escherichia coli* RNA Polymerase Selected by Function: Highly Efficient Promoters from Bacteriophage T5," J. Bacteriology, 164(1):70-77 (1985).
Kwon et al, "Bipartite Modular Structure of Intrinsic, RNA Hairpin-independent Termination Signal for Phage RNA Polymerases" J Biol. Chem., 274(49):34940-34947 (1999).
Possee et al., "Generation of Baculovirus Vectors for the High-Throughput Production of Proteins in Insect Cells," Biotechnology and Bioengineering, 101(6):1115-1122 (2008).
Pijlman et al., "Spontaneous excision of BAC vector sequences from bacmid-derived baculovirus expression vectors upon passage in insect cells," Journal of General Virology, 84(10):2669-2678 (2003).
Weyer U. et al., A Baculovirus Dual Expression Vector Derived from the Autographa Californica Nuclear Polyhedrosis Virus Polyhedrin and p10 Promoters: Coexpression of Two Influenza Virus Genes in Insect Cells J Gen Virol 2967-2974, 1991.
Juliant S et al. Engineering the Baculovirus Genome to Produce Galactosylated Antibodies in Lepidopteran Cells. Glycosylation Engineering of Biopharmaceuticals: Methods and Protocols, Methods in Molecular Biology, vol. 988, DOI 10.1007/978-1-62703-327-5_5, 2013.

* cited by examiner (*) Infectious viral DNA if recombination in locus PH has also taken place.

(*) Infectious viral DNA if recombination in locus gp37 has also taken place.

Figure 6

1. Construction of a specific pVT/gp37 (pVT/gp37-Cγ1)
This transfer vector contains the following expression cassette:
. Viral promoter P10
. DNA sequence encoding for a signal sequence of a human immunoglobulin (secretion sequence)
. 2 unique restriction sites for in phase cloning of the variable region (VH) of the antibody (region which gives the specificity of the antibody)
. DNA sequence which encodes a constant region of human IgG epsilon, mu or alpha (γ1-4)

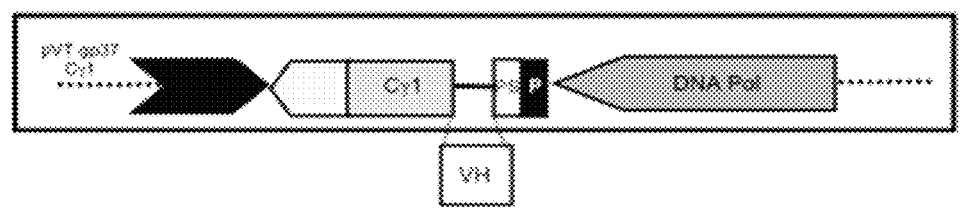

2. Insertion of DNAc encoding the variable region of the antibody (VH). There is then reconstitution of DNAc encoding the totality of the heavy chain.

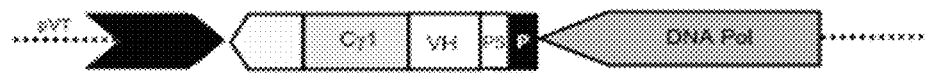

3. Generation of recombinant baculoviruses. Recombination between pVTgp37 loaded with the heavy chain + pVTPH loaded with the light chain + Bacmid 2

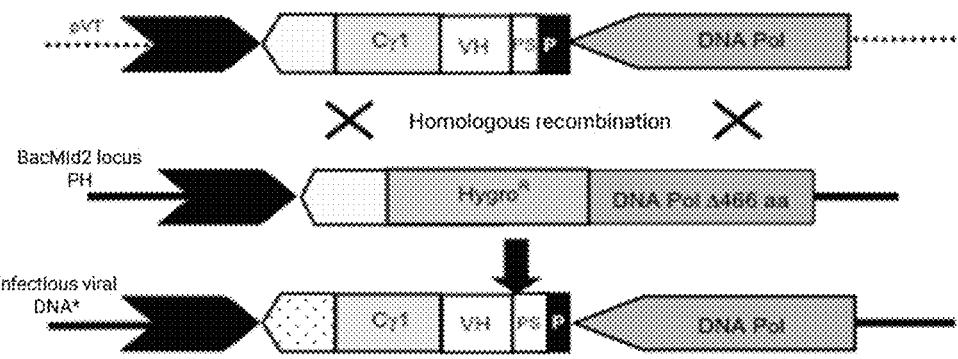

(*) Infectious viral DNA if recombination in locus PH has also taken place.

(*) Infectious viral DNA if 2nd locus gp37 recombination has also taken place.

(*) Infectious viral DNA if the 2 other recombinations, carried out respectively in loci PH and gp37 have also taken place.

Figure 15
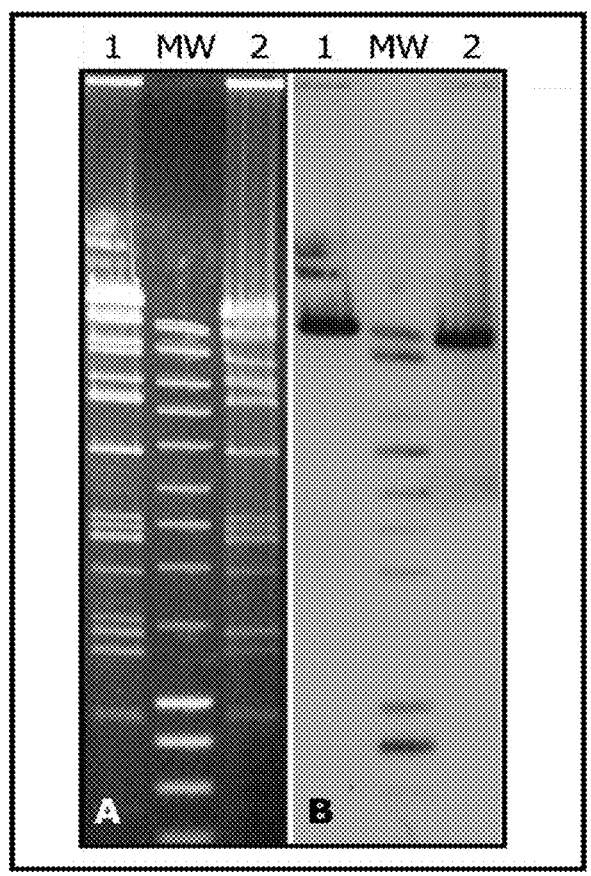
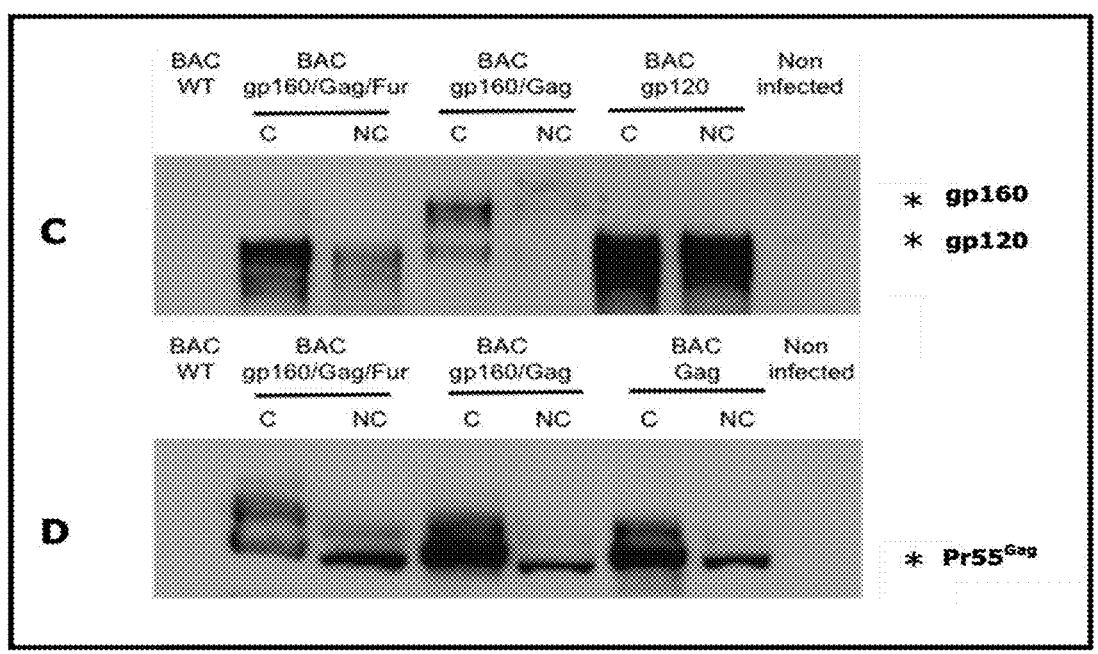

Figure 19
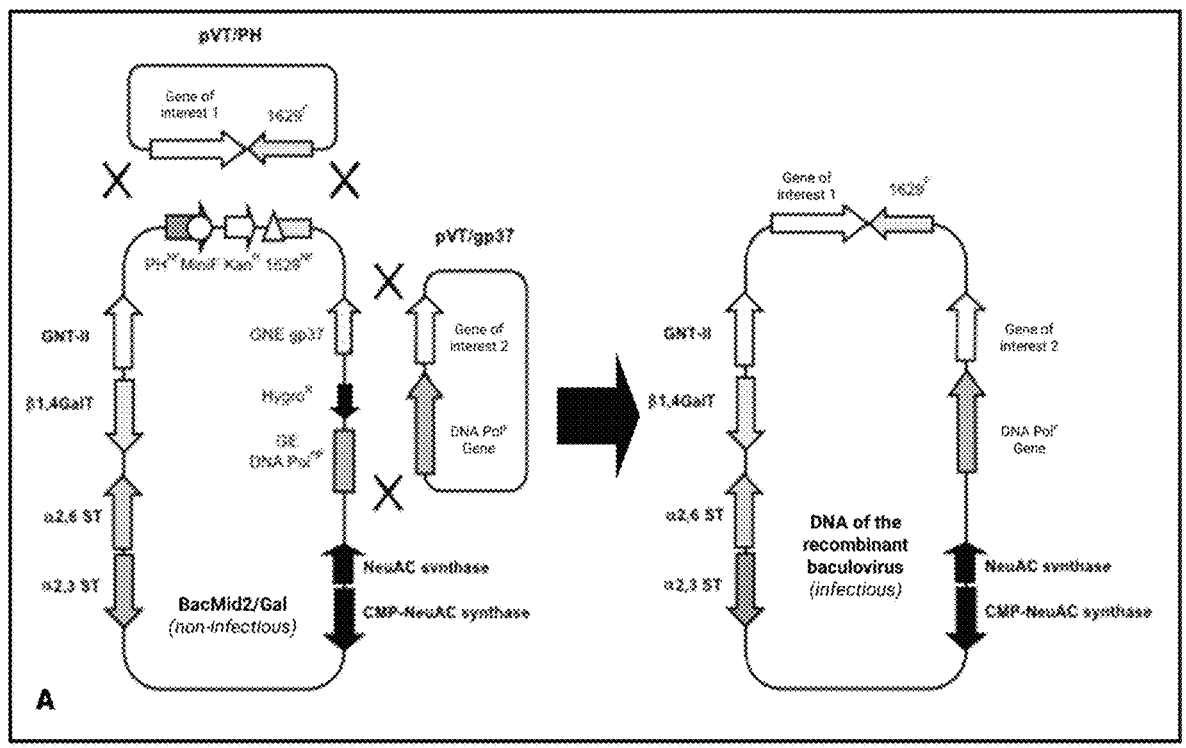
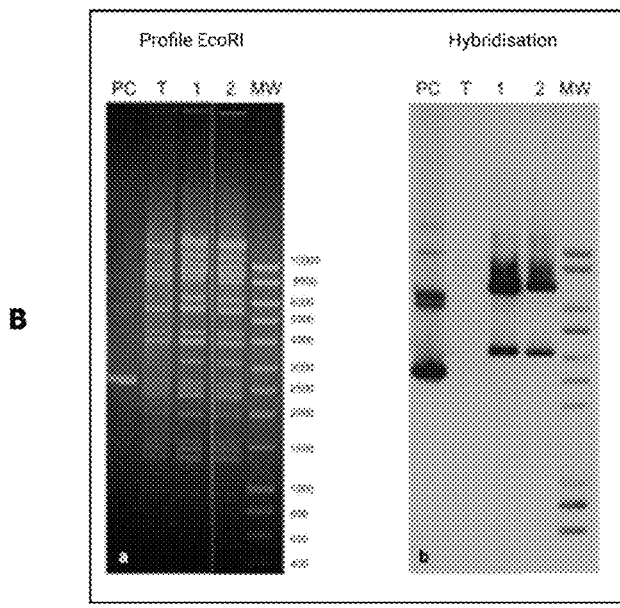

SEQUENCE LISTING

```
<160> NUMBER OF SEQ ID NOS: 21

<210> SEQ ID NO 1
<211> LENGTH: 75
<212> TYPE: DNA
<213> ORGANISM: Artificial Sequence
<220> FEATURE:
<223> OTHER INFORMATION: P10 wild

<400> SEQUENCE: 1
ataagaatta ttatcaaatc atttgtatat taattaaaat actatactgt aaattacatt     60
ttatttacaa tcatg                                                      75

<210> SEQ ID NO 2
<211> LENGTH: 71
<212> TYPE: DNA
<213> ORGANISM: Artificial Sequence
<220> FEATURE:
<223> OTHER INFORMATION: P10S1A

<400> SEQUENCE: 2
ataagtattt taatcttttc gtttgtataa attaatttat actatactgt ataaaaaaac     60
ctataaatat g                                                          71
```

```
<210> SEQ ID NO 3
<211> LENGTH: 71
<212> TYPE: DNA
<213> ORGANISM: Artificial Sequence
<220> FEATURE:
<223> OTHER INFORMATION: P10S1B

<400> SEQUENCE: 3
ataagtattt taatctttc gtttgtacca ctgcagtggt actatactgt ataaaaaaac    60
ctataaatat g                                                       71

<210> SEQ ID NO 4
<211> LENGTH: 19
<212> TYPE: DNA
<213> ORGANISM: Artificial Sequence
<220> FEATURE:
<223> OTHER INFORMATION: Sens39k

<400> SEQUENCE: 4
cgcagcaatt ccagcgagc                                               19

<210> SEQ ID NO 5
<211> LENGTH: 65
<212> TYPE: DNA
<213> ORGANISM: Artificial Sequence
<220> FEATURE:
<223> OTHER INFORMATION: Anti-sens mut39k

<400> SEQUENCE: 5
ctctagacct aaggcataaa agttttttat ttaatctgac atatttgtat cttgtgtatt   60
atcgc                                                              65

<210> SEQ ID NO 6
<211> LENGTH: 57
<212> TYPE: DNA
<213> ORGANISM: Artificial Sequence
<220> FEATURE:
<223> OTHER INFORMATION: Sens mut39k

<400> SEQUENCE: 6
gccttaggtc tagagtatat ttaatggttt ttattattgt tattattaat accctcc     57

<210> SEQ ID NO 7
<211> LENGTH: 21
<212> TYPE: DNA
<213> ORGANISM: Artificial Sequence
<220> FEATURE:
<223> OTHER INFORMATION: Antisens 39k

<400> SEQUENCE: 7
cctggtaatt tttgaccacg g                                            21

<210> SEQ ID NO 8
<211> LENGTH: 20
<212> TYPE: DNA
<213> ORGANISM: Artificial Sequence
<220> FEATURE:
<223> OTHER INFORMATION: Sens iap2

<400> SEQUENCE: 8
gatattgtgt gctcaatgtc                                              20

<210> SEQ ID NO 9
<211> LENGTH: 30
<212> TYPE: DNA
```

```
<213> ORGANISM: Artificial Sequence
<220> FEATURE:
<223> OTHER INFORMATION: Anti-sens BstBI

<400> SEQUENCE: 9
cctaaggtct agattcgaat acgtgtgtcg                                     30

<210> SEQ ID NO 10
<211> LENGTH: 37
<212> TYPE: DNA
<213> ORGANISM: Artificial Sequence
<220> FEATURE:
<223> OTHER INFORMATION: Sens BstBI

<400> SEQUENCE: 10
cgaatctaga ccttaggccg cggctaagcg ttaaacc                             37

<210> SEQ ID NO 11
<211> LENGTH: 23
<212> TYPE: DNA
<213> ORGANISM: Artificial Sequence
<220> FEATURE:
<223> OTHER INFORMATION: Anti-sens iap2

<400> SEQUENCE: 11
cgatcaccgt cgctgtcgtc ttc                                            23

<210> SEQ ID NO 12
<211> LENGTH: 24
<212> TYPE: DNA
<213> ORGANISM: Artificial Sequence
<220> FEATURE:
<223> OTHER INFORMATION: Sens orf51

<400> SEQUENCE: 12
ggaaaactct ttccgaagac gaac                                           24

<210> SEQ ID NO 13
<211> LENGTH: 40
<212> TYPE: DNA
<213> ORGANISM: Artificial Sequence
<220> FEATURE:
<223> OTHER INFORMATION: Anti-sens Xba/orf51

<400> SEQUENCE: 13
cctaaggtct agagtgcctt tgtttgcta ttttgcgccg                           40

<210> SEQ ID NO 14
<211> LENGTH: 31
<212> TYPE: DNA
<213> ORGANISM: Artificial Sequence
<220> FEATURE:
<223> OTHER INFORMATION: Sens Xba/orf51

<400> SEQUENCE: 14
ctctagacct taggtccgcg ctctcccacg c                                   31

<210> SEQ ID NO 15
<211> LENGTH: 28
<212> TYPE: DNA
<213> ORGANISM: Artificial Sequence
<220> FEATURE:
<223> OTHER INFORMATION: Anti-sens orf51

<400> SEQUENCE: 15
ggtgcagaac ataatgacgt ggccttac                                       28
```

<210> SEQ ID NO 16
<211> LENGTH: 116
<212> TYPE: DNA
<213> ORGANISM: Artificial Sequence
<220> FEATURE:
<223> OTHER INFORMATION: gene gp37 modified

<400> SEQUENCE: 16
tttagccatt tgagcgtatc tgcattcgtc gtctagacct aggatcccgc agcaaacaat      60
gcaattaata atgcaatgat tatgattata cttatagaac actaatcgga ataata         116

<210> SEQ ID NO 17
<211> LENGTH: 112
<212> TYPE: DNA
<213> ORGANISM: Artificial sequence
<220> FEATURE:
<223> OTHER INFORMATION: Synthetic promoter P10S1

<400> SEQUENCE: 17
ataagtattt taatcttttc gtttgtatat taattaaaat actatactgt ataaaaaaac      60
ctataaatat cccggattat tcataccgtc ccaccatcgg gcgtacgcca cc              112

<210> SEQ ID NO 18
<211> LENGTH: 32
<212> TYPE: DNA
<213> ORGANISM: Artificial Sequence
<220> FEATURE:
<223> OTHER INFORMATION: PCR primer senspif1

<400> SEQUENCE: 18
gaatacaacg ccacatctat tcctagtaca ac                                   32

<210> SEQ ID NO 19
<211> LENGTH: 50
<212> TYPE: DNA
<213> ORGANISM: Artificial Sequence
<220> FEATURE:
<223> OTHER INFORMATION: PCR primer pif1bac5'

<400> SEQUENCE: 19
ctagaggcgt taacctaagg tacttattgg agaatgtccg agtattttg                 50

<210> SEQ ID NO 20
<211> LENGTH: 50
<212> TYPE: DNA
<213> ORGANISM: Artificial Sequence
<220> FEATURE:
<223> OTHER INFORMATION: PCR primer pif1for3'

<400> SEQUENCE: 20
ccttaggtta acgcctctag aacatgagca ttttaaaagt tgtagaagcg                 50

<210> SEQ ID NO 21
<211> LENGTH: 33
<212> TYPE: DNA
<213> ORGANISM: Artificial Sequence
<220> FEATURE:
<223> OTHER INFORMATION: PCR primer revpif1

<400> SEQUENCE: 21
cattaacaat tactacggcg cattttgacc atc                                  33

BACULOVIRUS EXPRESSION SYSTEM

TECHNICAL FIELD

The invention relates to a method for producing a recombinant baculovirus of which the genome comprises one or more transgene(s) each encoding a protein maturation enzyme and at least two transgenes each encoding a polypeptide of interest, baculoviruses or recombinant baculovirus genomes obtained by this method, sets of homologous recombination elements, cells comprising a recombinant baculovirus or a recombinant baculovirus genome as well as the use of baculoviruses or recombinant baculovirus genomes for the production of polypeptides of interest.

TECHNOLOGICAL BACKGROUND

Baculoviruses are a family of rod-shaped viruses, specific to arthropods, which comprises four genera (Alphabaculovirus, Betabaculovirus, Deltabaculovirus, Gammabaculovirus) encompassing 49 species. Baculoviruses are not capable of replicating in the cells of mammals or other vertebrae.

The baculovirus genome is constituted of a double-stranded DNA molecule, circular, of a size comprised between 80 and 180 kpb. The baculovirus genome associates with highly basic proteins of 605 kDa, within a nucleocapsid with helicoidal symmetry, which contains a capsid protein of 39 kDa. The size of the genome determines the length of the nucleocapsid. The nucleocapsid is next enclosed in a lipoprotein envelope to form the viral particle or virion. These structures may be covered with a crystalline or polyhedral matrix essentially constituted of a single protein (polyhedrin) of around 30 kDa. Polyhedrons are large structures of which the size varies from 1 to 15 µm diameter with an outer polysaccharide envelope which confers additional protection.

Baculoviruses, of which the genome has been modified genetically, are used in biotechnology for the production, of recombinant proteins (i.e. recombinant baculoviruses). After penetration in an insect cell, these recombinant baculoviruses are going to use the machinery of the insect cell to produce the recombinant protein.

Recombinant baculoviruses are obtained by inserting one or more genes originating from other species (for example from human beings, other vertebrates, bacteria and viruses) into the genome of a parent baculovirus. These genes are placed under the control of a viral or cellular promoter (for example the promoter of the polyhedrin gene) to generate a recombinant baculovirus genome. The promoter enables the transcription of the foreign gene into messenger RNA which in its turn is translated into protein in the insect cell infected by the recombinant baculovirus. The advantage of using this system is that the level of production of the recombinant protein in insect cells infected by the recombinant baculovirus may be very important. The recombinant protein may next be purified from infected cells if the protein is intracellular or instead from the culture medium if the protein is secreted. The baculovirus expression system is widely used in industry and in research laboratories. In addition to the important productivity of the baculovirus expression system, this system is also highly appreciated because it makes it possible to produce biologically active recombinant proteins. Indeed, insect cells generally make it possible to obtain appropriate post-translational modifications.

However, certain proteins require post-translational modifications that insect cells are not capable of carrying out. These post-translational modifications being normally carried out by maturation enzymes of specific proteins.

For example, the majority of human glycoproteins have a so-called complex glycosylation, they are in general sialylated (FIG. 12A). Sialylation is an important element in the stabilisation of the structure of certain proteins, it makes them more soluble, more resistant to heat and more resistant to proteases. The level of sialylation of a protein may directly influence its half-life in the serum, desialylated proteins being rapidly captured by receptors to asialoproteins. There is an exception to this half-life model, antibodies. Indeed, the half-life of antibodies is essentially controlled via their interaction with a receptor at the domain Fc (FcR) (Fc for "crystallisable fragment": particular constant region of the antibodies (FIG. 13)), called receptor FcRn. Glycosylation has however a very important role in the control of the activity of antibodies quite particularly the N-glycosylation present in the CH2 domain of the constant region of the IgG on Asn297 (FIG. 13). Indeed, the nature of this N-glycosylation enables the modulation of what is called the effector activities of the antibodies, activities that are going to make it possible for example to kill a tumoral cell targeted by an antibody. It has notably been demonstrated that (i) ADCC (Antibody Dependent Cell-mediated Cytotoxicity) is increased very significantly when α1,6 fucose is eliminated from the core of the glycan and (ii) CDC (Complement Dependent Cytotoxicity) is dependent on the presence of galactose. Finally, even if the mechanical action is still very controversial, the sialylation of this glycan motif could be important for blocking the proinflammatory activity of antibodies.

Thus, if it is wished to produced highly cytotoxic antibodies, antibodies capable of inducing high ADCC and CDC activities, for example to destroy specifically a tumour, the ideal is to produce galactosylated antibodies. On the other hand, an antibody that will be used simply as a ligand, a ligand of a cellular receptor for example to induce apoptosis, or instead to carry out imaging by specifically marking a tissue, it will be desirable to use an antibody incapable of inducing cellular cytotoxicity, in this case a sialylated antibody will be the most suitable.

Numerous studies on the N-glycosylation potential of insect cells very clearly show that if the addition of glycans is specific, that is to say that it is always carried out on asparagine residues identical to those which are glycosylated naturally on the original protein expressed by the tissue (for example the Asn297 of the antibodies), the structure of glycans is different, they are shorter and there are no complex glycans (FIG. 12B). It has also been shown that these truncated structures result from the absence or the low activity of several enzymes involved in the biosynthesis of complex glycans such as N-acetylglucosaminyltransferase II (GnT-II) and β-1,4 galactosyltransferase (β-1,4 GalT), sialyltransferases and the absence of a sugar-nucleotide, CMP-NeuAc.

With the aim of obtaining correctly matured proteins of interest, it is thus important to complete the enzymatic maturation potential of the insect cell.

Baculoviruses comprising genes encoding protein maturation enzymes have already been described.

The article of Palmberger et al. (2012) relates to a recombinant baculovirus comprising in its genome sequences encoding for two glycosylation enzymes in a same locus. This baculovirus is used for the production of the antibodies 3D6 anti-gp41 of HIV. Two genes encoding the heavy and light chains of the antibodies were inserted into the genome of this baculovirus. These recombinant baculoviruses are generated from a bacmid (infectious in insect cells) in a bacterium. The construction method uses the Cre/Lox system and Tn7 transposition for an iterative integration of the different genes (genes of interest and protein maturation genes). A selection of the bacteria on different antibiotics is then necessary to isolate the infectious recombinant bacmids that will next be introduced, in the form of DNA, into insect cells to produce recombinant baculoviruses.

The article of Chang et al. (2003) discloses a recombinant baculovirus expressing both a polypeptide of interest (human α1-antitrypsin) and a series of glycosyltransferases in a single locus. The recombination is carried out in insect cells, with a non-infectious linearized viral DNA. The repair of this DNA consecutive to the homologous recombination with the transfer vectors makes it possible to reconstruct a circular and thus infectious viral DNA.

The methods for constructing these baculovirus are based on steps of iterative integrations of genes of interest and protein maturation genes bringing into play conventional integration systems.
  (i) either in a bacterium such as the Tn7 transposition or the cre/lox system (Palmberger et al. 2012)
  (ii) or conventional homologous recombination steps in an insect cell between a linearized viral DNA and a transfer vector (Chang et al. 2003).

In both cases, for each integrated transgene, a step of selection is necessary either (i) in the bacterium, a selection based on the presence of antibiotic resistance gene adjacent to the transgene, or (ii) in the insect cell, each recombination step necessitates the presence, in the viral DNA, of a new unique site for specific cleavage of a restriction enzyme to be able again to linearize the viral DNA and to perform a new integration. The repair of this DNA consecutive to homologous recombination with the transfer vectors makes it possible to reconstruct a circular and thus infectious viral DNA.

Thus, there still exists a need to develop methods that are easy to implement and which make it possible to produce recombinant proteins of interest, notably proteins comprising several distinct sub-units, such as antibodies in baculovirus expression systems and which may notably be developed on an industrial scale and which are capable of inducing an appropriate maturation of the protein of interest.

It is in particular necessary, in order to produce certain recombinant proteins of interest, composed of several peptide sub-units, to have a baculovirus expression system in which several transgenes, each encoding a sub-unit, may be integrated easily and preferably in a single step.

Yet, to be able to integrate several transgenes in a baculovirus, the methods known until now have necessitated:
  Either carrying out several successive steps, each step enabling the integration of one or two transgenes ("head to tail"). Thus, it has been technically possible, but very laborious, to integrate more than two transgenes an a baculovirus genome in a single step;
  Or to integrate multiple transgenes in a single locus. However, the homologous recombination for the integration of a DNA fragment of large size composed of several transgenes (expression cassettes) is often complicated, or even impossible, without inducing reworking of the viral genome. It is thus preferable to spread out uniformly, in the genome of a baculovirus, the positions of integration of several transgenes.

In order to eliminate the step of selection of recombinant baculoviruses having integrated with success a transgene of interest, a method has been proposed based on the joint use:
  of a baculovirus in which a gene essential for viral replication is non-functional, and
  of a transfer vector comprising a nucleotide sequence enabling to restore the function of a gene essential for replication, and a transgene encoding for a polypeptide of interest.

This method is notably described in the patent application WO 01/12829 and in the article of Possee et al., 2008.

However, this method only makes it possible to integrate one or two transgenes of interest (head to tail), in a single locus. The operation must be repeated several times to integrate a third or a fourth transgene in another locus, bound to another gene essential for replication which will have to be non-functional.

In addition, the integration of a transgene upstream or downstream of a gene essential for replication as described by Possee is capable of generating viruses of which the replication could be altered, and thus viruses replicating insufficiently, that is to say having in the culture supernatant a much lower content of infectious viral particles (PFU/ml) than a wild virus.

On the basis of this finding, the Applicant has developed a method that is particularly efficient and easy to implement for preparing homogeneous and stable recombinant baculoviruses, and which makes it possible to envisage a development at the industrial level for the production of recombinant proteins, for example multimeric proteins comprising several distinct sub-units.

SUMMARY OF THE INVENTION

In a first aspect the invention relates to a method for producing a recombinant baculovirus of which the genome comprises one or more transgene(s) each encoding a protein maturation enzyme and n transgenes each encoding a polypeptide of interest, said method comprising the steps of:
  a) Preparing, in an insect cell, a baculovirus genome capable of replicating which comprises one or more transgene(s) each encoding a protein maturation enzyme and n transgenes each encoding a polypeptide of interest, by homologous recombination between:
    a1) a replication deficient recombinant baculovirus genome in which n genes essential for viral replication are non-functional and which comprises one or more transgene(s) each encoding a protein maturation enzyme, and
    a2) n transfer vectors each comprising:
      i) a nucleotide sequence enabling to restore the function of one of the n non-functional genes essential for viral replication,
      ii) one of the n transgenes encoding a polypeptide of interest, the set of nucleotide sequences i) of the n transfer vectors being capable of restoring the replication of the replication deficient baculovirus genome, n being an integer at least equal to 2; and
  b) generating a recombinant baculovirus in an insect cell which comprises the recombinant baculovirus genome obtained at step a).

In a second aspect the invention relates to a recombinant baculovirus or a recombinant baculovirus genome comprising:
  a) n nucleotide sequences of formula (I):

[transgene encoding a polypeptide of interest]–
  [spacer nucleotide sequence]–[gene essential for
  functional viral replication]            (I), said spacer of nucleic acid sequence is constituted of 0 to 600 pb, preferably from 1 to 600 pairs of bases, said gene essential for functional viral replication is selected from 1629 (ORF9), Pk1 (ORF10), lef-1 (ORF14), ORF34, lef-11 (ORF37), p47 (ORF40), lef8 (ORF50), DNAJ domain (ORF51), ORF53, vp1054 (ORF54), Lef-9 (ORF62), DNA Pol (ORF65), lef-3 (ORF67), ORF73, ORF75, ORF81, p95 (ORF83), vp39 (ORF89), lef-4 (ORF90), p33 (ORF92), helicase (ORF95), Vp80 (ORF104), ORF106-107, odv-ec43 (ORF109), gp64/67 (ORF128), ORF132, ORF133, odv-ec27 (ORF144), ORF146, ie1 (ORF147), lef-2 (ORF6);

n being an integer at least equal to 2; and b) one or more transgene(s) each encoding a protein maturation enzyme.

In a third aspect the invention relates to a set of homologous recombination elements comprising:
  a) a replication deficient baculovirus genome in which n genes essential for viral replication are non-functional and which comprises one or more transgene(s) each encoding a protein maturation enzyme;
  b) n transfer vectors each comprising:
    i) a sequence of nucleic acids enabling to restore the function of one of the n non-functional genes essential for viral replication,
    ii) a transgene encoding a polypeptide of interest,
  n being an integer at least equal to 2.

In a fourth aspect the invention relates to a cell comprising a recombinant baculovirus or a recombinant baculovirus genome according to the invention or a set of homologous recombination elements according to the invention.

In a fifth aspect the invention relates to the use of a recombinant baculovirus or a recombinant baculovirus genome according to the invention or a cell according to the invention for the production of n polypeptides of interest.

DESCRIPTION DETAILED OF THE INVENTION

Definitions

Within the context of the present invention the expression "baculovirus" is taken to designate a rod-shaped virus specific to arthropods. A baculovirus generally comprises a nucleocapsid enclosing a baculovirus genome. Examples of baculoviruses are BmNPV, AcMNPV, ApNPV, BsSNPV, CfMNPV, EoSNPV, HaNPV, HzNPV, LdMNPV, MbMNPV, OpMNPV, SlMNPV, SeMNPV and TeNPV.

Within the context of the present invention the expression "baculovirus genome" is taken to designate the whole of the genetic material of a baculovirus, comprising in particular all the encoding and non-encoding nucleotide sequences of a baculovirus.

Within the context of the present invention the expression "replication deficient baculovirus genome" is taken to designate a baculovirus genome in which at least two genes essential for viral replication have been either deleted (entirely or partially) or mutated in such a way that the baculovirus genome has lost its ability to replicate in an insect cell. For example, the gene essential for viral replication no longer expresses itself or it is transcribed then translated into a non-functional protein. Thus, the genes deleted (entirely or partially) or mutated are called "non-functional genes essential for viral replications". The viral replication deficient baculovirus genomes are produced from parent baculovirus genomes using molecular biology techniques well known to those skilled in the art, and notably enabling the insertion and/or the deletion of nucleotide sequences in the parent baculovirus genome. Preferably, the replication deficient baculovirus viral genome comprises at least one nucleotide sequence which allows it to replicate within a bacterial cell. The nucleotide sequences enabling replication within a bacterial cell are not transgenes of interest in the sense of the invention. An example of bacterial replication element is the nucleotide sequence "Mini-F". Such replication elements are well known in the prior art. The bacterial cell may be *Escherichia coli*. A baculovirus genome which comprises a nucleotide sequence which makes it possible to replicate within a bacterial cell is known by the denomination "Bacmid". Preferably, the replication deficient baculovirus genome also comprises one or more nucleotide sequences encoding one or more selection markers enabling to select or to identify the bacterial cells transfected by the replication deficient baculovirus genome. The selection nucleotide sequences are not transgenes of interest in the sense of the invention. It may be for example an ampicillin resistance gene, a kanamycin resistance gene, a hygromycin resistance gene, a zeocin resistance gene and/or a tetracycline resistance gene.

Within the context of the present invention the expression "recombinant baculovirus genome" is taken to designate a baculovirus genome which comprises one or more transgene(s) each encoding a protein maturation enzyme and n transgenes each encoding a polypeptide of interest. The term "recombinant baculovirus genome" according to the invention corresponds to the baculovirus genome obtained by the implementation of the method according to the invention, that is to say the baculovirus genome obtained by homologous recombination between the replication deficient baculovirus genome and n transfer vectors.

Within the context of the present invention the expression "recombinant baculovirus" is taken to designate a baculovirus of which the genome is a recombinant baculovirus genome, that is to say a baculovirus of which the genome comprises one or more transgene(s) each encoding a protein maturation enzyme and n transgenes each encoding a polypeptide of interest. The recombinant baculovirus may be produced after replication of the recombinant baculovirus genome in an insect cell. The recombinant baculovirus is capable of infecting insect cells. Preferably, the recombinant baculovirus according to the invention is infectious for an insect cell.

"Gene" is taken to designate a nucleotide sequence capable of being transcribed then translated into polypeptide, for example into protein. One then speaks of gene encoding a polypeptide.

Within the context of the present invention "transgene" is taken to designate a gene which is not naturally present in the genome of a baculovirus. It may be for example a gene of human origin, a gene of animal origin, a gene of plant origin, a gene of viral origin or a gene of bacterial origin. Within the context of the invention, the transgene is either a "transgene encoding a protein maturation enzyme", or a "transgene encoding a polypeptide of interest".

"Distinct transgenes" is taken to designate transgenes not having the same nucleotide sequence.

A transgene in the sense of the present invention is placed under the control of appropriate elements for its expression in the insect cell. "Appropriate elements" is taken to designate the set of elements necessary for its transcription into messenger RNA (RNAm) and for the translation of RNAm into polypeptide. Among the elements necessary for transcription, the promoter assumes particular importance. It may be a constituent promoter or a regulatable promoter and it may be of baculoviral origin or of arthropod origin (e.g. of insect origin). The important point is that the chosen promoter is suited for the expression of the transgene in the insect cell. Generally speaking, a promoter in use in the present invention may be modified so as to contain regulatory sequences. As examples of promoters it is possible to cite the promoter polyhedrin, the promoter P10, synthetic promoters derived from polyhedrin and P10 promoters, the promoter IE1 of the baculovirus CfMNPV, the promoter IE1 of the baculovirus LdMNPV, the promoter gp64 of the baculovirus OpMNPV, the promoter IE1 of the shrimp virus WSSV (white spot syndrome virus), the promoter P9 of the densovirus of *Junonia coenia* (JcDNV), the cellular promoter A3 (actin 3) of the silkworm *Bombyx mori*. In a particular embodiment, one or more transgenes is placed under the control of a synthetic promoter derived from the wild promoter P10 (SEQ ID NO: 1), preferably the synthetic promoter P10S1A (SEQ ID NO: 2) or P10S1B (SEQ ID NO: 3).

"Expression cassette" is taken to designate a nucleotide sequence generally constituted of one or more genes and suitable elements for its/their expression, for example a transgene and the suitable elements for its expression in the insect cell.

"Protein maturation enzyme" is taken to designate an enzyme involved in the maturation of proteins. In particular, the maturation operated by a protein maturation enzyme leads to the production of a stable protein and/or a protein having all or part of its biological activity. For example, the protein maturation enzyme may act at the level of the peptide sequence of a protein (for example by cleavage), at the folding level (this is the case for example of chaperone proteins), at the glycosylation level, or at the level of any other post-translational modification such as for example phosphorylation or methylation. The protein maturation enzyme may be a signal peptidase, a furin, a proprotein convertase, a glycosyltransferase, a glycosidase, a chaperone protein, an isomerase disulphide, an acyltransferase, a methyltransferase, a hydroxylase, a transglutaminase, a farnesyltransferase, a geranylgeranyltransferase, a N-myristoyltransferase, a palmityltransferase, a protein kinase, a phosphatase, a transpeptidase, a carboxylase and/or a ubiquitin ligase.

"Glycosyltransferase" is taken to designate an enzyme capable of catalysing the transfer of a monosaccharide, from an activated sugar (donor), generally by a phosphate, to an acceptor molecule (usually an alcohol or an amine). The transfer acceptor may also be a peptide residue, usually serine, threonine or more rarely tyrosine, hydroxylysine and hydroxyproline during O-glycosylations (O-mannose, O-fucose, O-GalNAc, O-GlcNAc, O-galactose and O-glucose), or an asparagine during N-glycosylation. An activated mannose may also be transferred onto a tryptophan to form a C-mannosyl tryptophan. The glycosyltransferase may be selected from N-acetylglucosaminyltransferases I, II, III, IV, V, VB, VI and IX, a galactosyltransferase, for example a beta-1,4-galactosyltransferase, for example selected from beta-1,4-galactosyltransferase 1, 2, 3, 4, 5, 6 and 7, CMP-NeuAc synthase, NeuAc synthase, protein-O-mannosyltransferases 1 and 2, protein-O-fucosyltransferases 1 and 2, protein-O-glucosyltransferase 1, protein-O-GlcNAc transferase, GalNAc transferase, fucosyltransferases 1, 2, 3, 4, 5, 6, 7, 8, 9, 10 and 11 (FUT1 b FUT11) and sialyltransferases, for example α2,3 sialyltransferase and α2,6 sialyltransferase.

"Polypeptide" is taken to designate a chain of amino acids bound by peptide bonds. For example, a polypeptide may be a protein, a protein sub-unit, a protein fragment or simply a chain of amino acids. Generally, a polypeptide is formed of at least 10 amino acids.

"Polypeptide of interest" or "recombinant polypeptide of interest" is taken to designate a polypeptide encoded by a transgene. For example, the polypeptide of interest may be a sub-unit of a multimeric protein. Advantageously, it is a polypeptide of therapeutic and/or diagnostic interest, that is to say a polypeptide that may be used in therapy or in diagnostics.

"Distinct polypeptides of interest" is taken to designate polypeptides not having the same sequence of amino acids.

"Distinct sub-units" is taken to designate sub-units of a multimeric protein not having the same sequence of amino acids. Thus, a "protein comprising n distinct sub-units" is a protein which comprises n sub-units each having a specific sequence of amino acids which are bound together by non-covalent bonds and/or covalent bonds.

"Multimeric protein" is taken to designate a protein comprising several sub-units. A multimeric protein may comprise several identical sub-units (homomultimeric protein) or several distinct sub-units (heteromultimeric protein).

"Protein complex" is taken to designate an assembly constituted of several proteins having a functional or structural bond with each other, for example a "Virus-Like-Particle" (VLP) or a multienzymatic complex.

According to the present invention, the expression "replication" or "viral replication" is understood to extend to both the replication of the baculovirus genome and the baculovirus. Given that the replication of the baculovirus genome in an insect cell is essential for the replication of the baculovirus in the insect cell. Thus, a gene essential for viral replication is taken to designate a gene essential for replication of the baculovirus in the insect cell. The replication of the baculovirus in the insect cell enables the generation of infectious baculovirus. Thus, the method of the invention makes it possible to generate an infectious recombinant baculovirus in a cell, notably an insect cell.

Within the context of the present invention the expression "homologous recombination" is taken to designate the exchange of genetic information between two different nucleotide sequences, necessitating the presence of homologous sequences between two different nucleotide sequences.

The term "antibody" is used herein in the widest sense and encompasses various antibody structures widely described in the literature, including, but without being limited thereto, antibodies whatever their origin, monoclonal antibodies, polyclonal antibodies and fragments of antibodies as long as they exhibit the desired activity (for example bond to the antigen). It may be a mono-specific or multi-specific antibody, for example bi-specific. The antibodies may be an IgA, IgD, IgE, IgG or an IgM. Examples of fragments of antibodies include, but without being limited thereto, fragments Fv, Fab, Fab', F(ab')2; diabodies; scFv/Fc; antibodies of camelid type (for example the VHH); single chain antibody molecules (for example scFv).

Method for Preparing a Recombinant Baculovirus

The invention relates to a method for producing a recombinant baculovirus of which the genome comprises one or more transgene(s) each encoding a protein maturation enzyme and n transgenes each encoding a polypeptide of interest, said method comprises the steps of:

a) Preparing, in an insect cell, a baculovirus genome capable of replicating which comprises one or more transgene(s) each encoding a protein maturation enzyme and n transgenes each encoding a polypeptide of interest, by homologous recombination between:

a1) a replication deficient baculovirus genome in which n genes essential for viral replication are non-functional and which comprises one or more transgene(s) each encoding a protein maturation enzyme, and a2) n transfer vectors each comprising:
  i) a nucleotide sequence enabling to restore the function of one of the n non-functional genes essential for viral replication,
  ii) one of the n transgenes encoding a polypeptide of interest, the set of nucleotide sequences i) of the n transfer vectors being capable of restoring the replication of the replication deficient baculovirus genome, n being an integer at least equal to 2; and b) Generating a recombinant baculovirus in an insect cell which comprises the recombinant baculovirus genome obtained at step a).

The n transgenes each encoding a polypeptide of interest are borne by the n transfer vectors which recombine with the replication deficient baculovirus viral genome in which n genes essential for viral replication are non-functional and which comprises one or more transgene(s) each encoding a protein maturation enzyme. After recombination, the n transgenes each encoding a polypeptide of interest are integrated in the genome of the recombinant baculovirus.

Step a)

The recombination takes place in an insect cell between (a1) a replication deficient baculovirus genome in which n genes essential for viral replication are non-functional and which comprises one or more transgene(s) each encoding a protein maturation enzyme and (a2) the n transfer vectors.

Advantageously, recombination within the context of the present invention takes place in a single step in the insect cell, and this is so whatever the number n of transgenes to integrate. That is to say that the recombination of the n transgenes each encoding a polypeptide of interest with the replication deficient baculovirus genome takes place simultaneously or quasi-simultaneously in the insect cell. This simultaneous recombination is one of the main advantages of the method according to the invention because it makes it possible to produce the desired recombinant baculovirus genome rapidly and in a single step.

In a particular embodiment, the replication deficient baculovirus genome is obtained from a baculovirus genome selected from or derived from the genome of BmNPV, AcMNPV, ApNPV, BsSNPV, CfMNPV, EoSNPV, HaNPV, HzNPV, LdMNPV, MbMNPV, OpMNPV, SlMNPV, SeMNPV or TeNPV, preferably AcMNPV.

In a preferred embodiment, the replication deficient baculovirus genome implemented in the method is in circular form. Thus, the method according to the invention does not necessitate the linearization of the replication deficient genome.

The transfer vectors may also contain one or more nucleotide sequences that allow them to replicate within a bacterial cell. They may also contain genes encoding a selection marker enabling to select or to identify bacterial cells transformed with a transfer vector.

One of the main advantages of the method of the invention is that the ability of the replication deficient viral baculovirus genome to replicate is restored by recombination with the n transfer vectors. Indeed, each of the n transfer vectors encode, in addition to one of the n transgenes encoding a polypeptide of interest, a nucleotide sequence enabling to restore the function of one of the n non-functional genes essential for viral replications. Thus, only a recombination with the set of n transfer vectors makes it possible to restore the replication of the replication deficient baculovirus genome. Thus, the method of the invention guarantees that only the genomes of recombinant baculoviruses containing the n transgenes encoding a polypeptide of interest are able to generate infectious recombinant baculoviruses. This method avoids having to use expensive, time consuming tests to identify the recombinant baculoviruses containing the n transgenes encoding a polypeptide of interest.

In a preferred embodiment, the genes essential for viral replication are chosen from 1629 (ORF9), Pk1 (ORF10), lef-1 (ORF14), ORF34, lef-11 (ORF37), p47 (ORF40), lef8 (ORF50), DNAJ domain (ORF51), ORF53, vp1054 (ORF54), Lef-9 (ORF62), DNA Pol (ORF65), lef-3 (ORF67), ORF73, ORF75, ORF81, p95 (ORF83), vp39 (ORF89), lef-4 (ORF90), p33 (ORF92), helicase (ORF95), vp80 (ORF104), ORF106-107, odv-ec43 (ORF109), gp64/67 (ORF128), ORF132, ORF133, odv-ec27 (ORF144), ORF146, ie1 (ORF147) and lef-2 (ORF6). These genes are preferred because they are adjacent to a gene not essential for viral replication. Thus, in a preferred embodiment, in the replication deficient baculovirus viral genome, the n non-functional genes essential for viral replication are each adjacent to a gene not essential for viral replication. As detailed throughout the present application, the n transgenes each recombine at the locus of a gene not essential for viral replication adjacent to a gene essential for viral replication that is non-functional. Given that the gene not essential for viral replication is not essential for the replication of the baculovirus genome, recombination does not affect the capacity of the recombinant baculovirus genome to replicate.

The n transgenes are integrated either within a gene not essential for viral replication or in an intergenic zone, between 2 non-essential genes, or instead upstream or downstream of a gene essential for viral replication.

When the transgene is integrated upstream or downstream of an essential gene (construction of BacMid2-GNTII-β1, 4GT-CMPNeuAcS-NeuAcS-ST3 (or BacSia3) described in example 12, with the integration of the gene ST3 downstream of orf51), the baculovirus thus generated, although viable, may however have an altered replication and thus relatively low viral titres.

According to a preferred embodiment of the invention, the n transgenes are integrated within n genes not essential for viral replication, which makes it possible to obtain baculoviruses much more stable in the course of replication cycles, and thus to obtain sufficient viral titres to envisage industrial production.

Examples of integration of a transgene within a gene not essential for viral, replication are described in the examples, notably in example 9, with the integration of the gene fur in the genes Chit/Cath, in example 10, with the integration of the gene β1,4GalT in the gene egt, in example 12 with the integration of the genes NeuAc synthase and CMP-NeuAc synthase in the gene iap2 and in example 14 relative to the cloning of the transgene a2,6-sialyltransferase I (ST6GalI) in ORF119 (PIF1) of BacMid2-GNTII-β1,4GT-CMP-NeuAcS-NeuAcS.

In the sense of the present invention, a non-functional gene essential for viral replication is adjacent to a gene not essential for viral replication when the two genes succeed each other or partially overlap on the genome of the baculovirus, preferably no other gene is comprised between the non-functional gene essential for viral replication and the gene not essential for viral replication. Advantageously, the two aforementioned genes are separated by a spacer nucleotide sequence, for example a non-encoding spacer nucleotide sequence. In particular, the spacer nucleotide sequence has a length ranging from 1 pb to 600 pb. It is also possible that no separating nucleotide sequence (i.e. 0 pb) separates the two aforementioned genes, that is to say that the two aforementioned genes are placed side by side on the genome of the baculovirus or partially overlap. Alternatively, the spacer nucleotide sequence may comprise a gene not essential for viral replication.

The Applicant has noticed that the choice of non-functional genes essential for viral replications adjacent to genes not essential for viral replication was particularly advantageous and made it possible to obtain homogeneous homologous recombination and thus to obtain homogeneous recombinant baculovirus genomes. As explained elsewhere, only a perfect recombination of the n vectors makes it possible to obtain a recombinant baculovirus genome capable of replicating in an insect cell. Thus, the genomes of the recombinant baculoviruses prepared by the method according to the invention are homogeneous to more than 90%, advantageously to more than 95%, preferably to more than 99% and in a completely preferred manner around 100%, for example the recombinant baculovirus genomes prepared by the method according to the invention are all identical.

In a particular embodiment, the gene not essential for viral replication is selected from Ph (ORF 8), ORF11, ORF13, egt (ORF15), v-ubiquitin (ORF35), 39K (ORF36), ORF38, p43 (ORF39), lef-12 (ORF41), pcna (ORF49), ORF52, ORF55, Fp (ORF61), ORF63, gp37 (ORF64), ORF68, ORF72, ORF74, ORF82, cg30 (ORF88), ORF91, pif-4 (ORF96), he65 (ORF105), ORF108, ORF110, cathepsin (ORF127), p24 (ORF129), pp34 (ORF131), ORF134, ORF145, odv-e56 (ORF148), ORF5.

Advantageously, the gene essential for viral replication/gene not essential for viral replication couple is selected from the couples listed in table 1 below:

TABLE 1

Couples of adjacent genes comprising an essential gene and a non-essential gene for viral replication

| Couple | Essential gene | Non-essential gene | Spacing between the 2 genes |
|---|---|---|---|
| 1 | 1629 (ORF9) | Ph (ORF 8) | 29 bp |
| 2 | Pk1 (ORF10) | ORF11 | 163 bp |
| 3 | lef-1 (ORF14) | ORF13 | Overlap |
|   |   | or egt (ORF15) | 112 bp |
| 4 | ORF34 | v-ubiquitin (ORF35) | 20 bp |
| 5 | lef-11 (ORF37) | 39K (ORF36) | Overlap |
|   |   | or ORF38 | Overlap |
| 6 | p47 (ORF40) | p43 (ORF39) | 7 bp |
|   |   | or lef-12 (ORF41) | Overlap |
| 7 | Lef8 (ORF50) | pcna (ORF49) | 109 bp |
| 8 | DNAJ domain (ORF51) | ORF52 | 202 bp |
| 9 | ORF53 | ORF52 | 1 bp |
| 10 | vp1054 (ORF54) | ORF55 | 91 bp |
| 11 | Lef-9 (ORF62) | Fp (ORF61) | 26 bp |
|    |   | or ORF63 | 60 bp |
| 12 | DNA Pol (ORF65) | gp37(ORF64) | 137 bp |
| 13 | lef-3 (ORF67) | ORF68 | Overlap |
| 14 | ORF73 | ORF72 | 8 bp |
| 15 | ORF75 | ORF74 | 17 bp |
| 16 | ORF81 | ORF82 | Overlap |
| 17 | p95 (ORF83) | ORF82 | Overlap |
| 18 | vp39 (ORF89) | cg30 (ORF88) | 2 bp |
| 19 | lef-4 (ORF90) | ORF91 | 0 bp |
| 20 | p33 (ORF92) | ORF91 | 37 bp |
| 21 | helicase (ORF95) | pif-4 (ORF96) | Overlap |
| 22 | vp80 (ORF104) | he65 (ORF105) | 27 bp |

TABLE 1-continued

Couples of adjacent genes comprising an essential gene and a non-essential gene for viral replication

| Couple | Essential gene | Non-essential gene | Spacing between the 2 genes |
|---|---|---|---|
| 23 | ORF106-107 | he65 (ORF105) | 544 bp |
| 24 | odv-ec43 (ORF109) | ORF108 | 11 bp |
|    |   | or ORF110 | 35 bp |
| 25 | gp64/67 (ORF128) | cathepsin (ORF127) | 224 bp |
|    |   | or p24 (ORF129) | 182 bp |
| 26 | ORF132 | pp34 (ORF131) | 211 bp |
| 27 | ORF133 | ORF134 | 50 bp |
| 28 | odv-ec27 (ORF144) | ORF145 | 69 bp |
| 29 | ORF146 | ORF145 | Overlap |
| 30 | ie1 (ORF147) | odv-e56 (ORF148) | 61 bp |
| 31 | lef-2 (ORF6) | ORF5 | Overlap |

The greyed lines/bold characters represent the non-functional essential genes in the baculoviruses of examples 1, 2 and 3 (couples 1, 12, and 25).

In an advantageous embodiment, the n nucleotide sequences enabling to restore the function of the n non-functional genes essential for viral replications each recombine with a non-functional gene essential for viral replication such as listed in table 1; whereas the n transgenes encoding a polypeptide of interest each recombine at the locus of a gene not essential for viral replication, said non-essential gene being the gene adjacent to said essential gene of which the function was restored during this step of homologous recombination, such as presented in table 1.

Thus, when the essential gene of which the function is restored is the gene 1629 (ORF9), the transgene encoding for a peptide of interest will be integrated in the non-essential gene Ph (ORF8); when the essential gene of which the function is restored is the gene Pk1 (ORF10), the transgene encoding for a peptide of interest will be integrated in the non-essential gene ORF11, and so on for each couple of adjacent genes listed in table 1.

The method according to the invention implements a mechanism of homologous intermolecular recombination. Generally speaking, the mechanism of homologous recombination consists in the exchange of homologous nucleotide sequences between the replication deficient baculovirus genome and the n transfer vectors. These nucleotide sequences may be identical or substantially homologous.

In a particularly advantageous embodiment, the transfer vectors comprise, on either side of the expression cassette of the transgene encoding a polypeptide of interest, flanking sequences homologous to the replication deficient baculovirus genome. The degree of homology of the flanking sequences with the corresponding part of the replication deficient baculovirus genome may be variable but must be sufficient to enable intermolecular recombination. For the purposes—of the present invention, it is preferable that it is greater than 70%, advantageously greater than 80%, preferably greater than 90% and in an entirely preferred manner around 100%, preferably identical. In addition, a short region of homology may be sufficient to enable intermolecular recombination, that is to say at least 10 consecutive nucleotides (or pairs of bases) common between the flanking sequences and their homologous sequences in the replication deficient baculovirus genome. Within the context of the present invention, the length of the flanking sequences may range from 10 pb (i.e. 10 pairs of bases) to 10 kb (i.e. 10,000 pairs of bases), advantageously from 100 pb to 6 kb, preferably from 200 pb to 6 kb and, in an entirely preferred manner from 400 pb to 6 kb. Thus, the genetic material located between the flanking sequences of the n transfer vectors replaces the genetic material located between the two sequences homologous to the flanking sequences of the replication deficient baculovirus genome. This intermolecular exchange makes it possible to obtain a recombinant baculovirus genome capable of generating an infectious recombinant baculovirus in the insect cell.

According to the invention, the set of nucleotide sequences i) (i.e. the nucleotide sequences enabling to restore the function of the n non-functional genes essential for viral replications) of the n transfer vectors are capable of restoring the replication of the replication deficient baculovirus genome. Indeed, intermolecular exchange makes it possible to restore the function of the n non-functional genes essential for viral replications. In other words, the restauration of the function of the n non-functional genes essential for viral replications occurs when the homologous recombination takes place correctly. This comes from the fact that the n transfer vectors each comprise a nucleotide sequence enabling to restore the function of one of the n non-functional genes essential for viral replications.

For example, when n=2, a replication deficient baculovirus genome in which two genes essential for viral replication are non-functional recombine with two transfer vectors which each comprise a nucleotide sequence enabling to restore the function of one of the two non-functional genes essential for viral replication. Which means that recombination with the first transfer vector makes it possible to restore the function of a first non-functional gene essential for viral replication and recombination with the second transfer vector makes it possible to restore the function of the second non-functional gene essential for viral replication. Thus, only the recombination of two transfer vectors with the replication deficient baculovirus genome makes it possible to restore the function of the two non-functional genes essential for viral replications and thus to restore the replication of the replication deficient baculovirus genome. This restoration of the function of the two essential genes makes it possible to obtain a recombinant baculovirus genome capable of generating infectious recombinant baculoviruses in the insect cell.

Thus, according to the method of the invention, recombination with the n transfer vectors, or multi-recombination, is necessary to restore the replication of the replication deficient baculovirus genome.

In a surprising manner, the inventors have demonstrated that multi-recombination can be done in a single step, simultaneously, in the insect cell. This is particularly advantageous since the replication deficient baculovirus genome and the n transfer vectors may be introduced at the same time in the insect cell, that is to say that the replication deficient baculovirus genome and the n transfer vectors are introduced simultaneously in the insect cell, in other words the replication deficient baculovirus genome and the n transfer vectors are introduced in a single step in the insect cell, and this is so whatever the number n of transfer vectors. Multi-recombination in a single step makes it possible to obtain easily and rapidly homogeneous recombinant baculovirus genomes.

The method according to the invention makes it possible to produce a recombinant baculovirus which comprises n transgenes each encoding a polypeptide of interest. The set of n polypeptides of interest may form, for example, a protein comprising several sub-units. The set of n polypeptides of interest may also be the constituent proteins of a protein complex, for example a VLP. The set of n polypeptides of interest are produced by an insect cell infected by the recombinant baculovirus which comprises the n transgenes each encoding a polypeptide of interest.

Thus, in a particular embodiment, the n polypeptides of interest form several distinct proteins of interest. It may involve several distinct proteins of interest comprising a single polypeptide chain, several distinct proteins of interest comprising several identical sub-units and/or several distinct proteins of interest comprising several distinct sub-units. The number of distinct proteins of interest formed by the n polypeptides of interest will be equal to or less than n. For example, three polypeptides of interest (n=3) may form (i) a first protein of interest comprising a single polypeptide chain and a second protein of interest comprising two distinct sub-units, (ii) three distinct proteins of interest each comprising a single polypeptide chain, (iii) a first protein of interest comprising several identical sub-units and a second protein of interest comprising two distinct sub-units, or (iv) three distinct proteins of interest each comprising several identical sub-units.

In another particular embodiment, the n polypeptides of interest form a single protein. In this embodiment, the protein then comprises n distinct sub-units, each of the sub-units being one of the n polypeptides of interest.

The method according to the invention is thus particularly advantageous for preparing a recombinant baculovirus which comprises transgenes encoding a protein of interest comprising several distinct sub-units, for example a protein of interest which is only active when it comprises all the sub-units. The sub-units being generally bound together by non-covalent bonds (e.g. hydrophobic bonds) and/or covalent bonds (e.g. disulphide bridges between two cysteines). The method of the invention is thus particularly advantageous for preparing a recombinant baculovirus which comprises transgenes encoding a multimeric protein, for example an antibody or an antibody fragment.

The number of transfer vectors will depend on the desired number of distinct polypeptides of interest that it is wished to produce. For example, two transfer vectors will be used for a protein comprising two distinct sub-units, three transfer vectors will be used for a protein comprising three distinct sub-units, etc. Advantageously, each transfer vector comprises a transgene encoding a polypeptide of interest different from the transgenes encoding the other polypeptides of interest comprised in the other transfer vectors. In a particular embodiment, a transfer vector may comprise more than one transgene, for example two transgenes, each encoding a polypeptide of interest. In this particular embodiment, the transgenes may be present in a same locus, preferably at the most two transgenes per locus.

Advantageously, n is an integer ranging from 2 to 31, for example ranging from 2 to 10. For example, for a protein of interest comprising several distinct sub-units, the value of n will correspond to the number of distinct sub-units of said protein of interest.

In a particular embodiment, n=2. In this case, it is possible to distinguish the following implementations:
  the two transgenes each encode a sub-unit of a protein comprising two sub-units, advantageously the two transgenes each encode a distinct sub-unit of a protein comprising two distinct sub-units. For example, the first transgene encodes the light chain of an antibody and the second transgene encodes the heavy chain of an antibody. Such an exemplary configuration is described in example 6. The protein comprising two distinct sub-units may also be a monospecific antibody or a peptide hormone comprising two distinct sub-units; or the two transgenes each encode a distinct polypeptide of interest. For example, the two distinct polypeptides of interest constitute a set of two viral proteins, a multienzymatic complex, a protein complex, for example a VLP composed of two distinct proteins.

Figure 16:
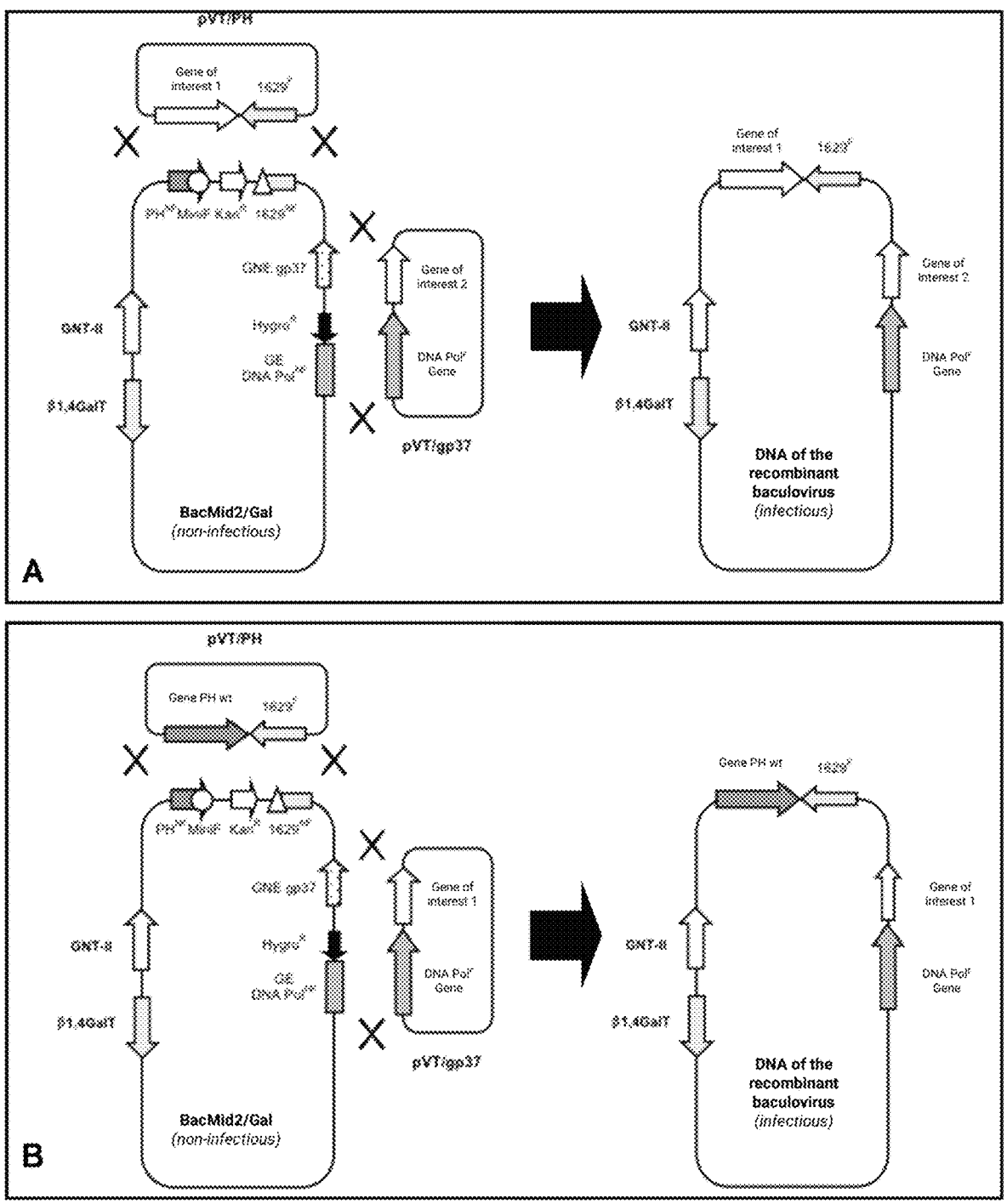
Figure 17:
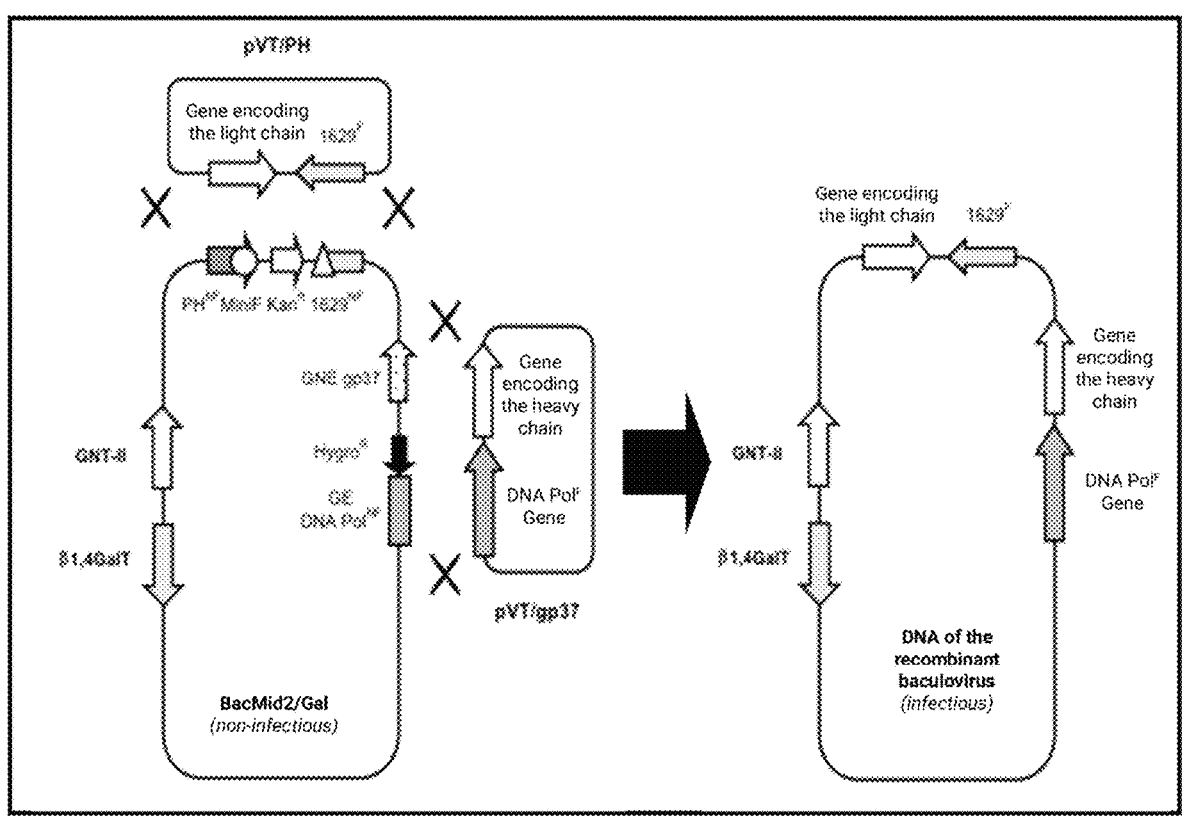

FIGS. 16, 17 and 19 diagrammatically illustrate representations of baculovirus genomes comprising two transgenes of interest.

In a particular embodiment, n=3. In this case, it is possible to distinguish the following implementations:
  the three transgenes each encode a sub-unit of a protein comprising three sub-units, advantageously the three transgenes each encode a distinct sub-unit of a protein comprising three distinct sub-units. The protein comprising three distinct sub-units may be a bispecific antibody or a peptide hormone comprising three distinct sub-units. For example, the first transgene encodes a first light chain of a bispecific antibody, the second transgene encodes a second light chain of a bispecific antibody and the third transgene a heavy chain of a bispecific antibody; or
  the three transgenes each encode a distinct polypeptide of interest. For example, the three polypeptides of interest constitute a set of three viral proteins, a multienzymatic complex, a protein complex, for example a VLP composed of three distinct proteins. Such an exemplary configuration is presented in example 7, where "BacMid3" is used for the production of 3 proteins of the flu virus (see also FIG. 10).

For this particular embodiment, the baculovirus BacMid3 described in example 3, of which the genes essential for replication 1629, DNApol and gp64 are non-functional, could be used for the simultaneous integration of these three transgenes.

In a particular embodiment, n=4. In this case, it is possible to distinguish the following implementations:
  the four transgenes each encode a sub-unit of a protein comprising four sub-units, advantageously the four transgenes each encode a distinct sub-unit of a protein comprising four distinct sub-units. The protein comprising four distinct sub-units may be a peptide hormone comprising four distinct sub-units; or
  the four transgenes each encode a distinct polypeptide of interest. For example, the four polypeptides of interest constitute a set of four viral proteins, a multienzymatic complex, a protein complex, for example a VLP composed of four distinct proteins.

Advantageously, the recombinant baculovirus produced by the implementation of the method of the invention does not comprise a nucleic acid sequence which enables it to replicate within a bacterial cell. Optionally, the nucleic acid sequence that makes it possible to replicate the replication deficient baculovirus genome within a bacterial cell may be eliminated during the step of homologous recombination in the insect cell.

Step a) is carried out after introduction into the insect cell of the transfer vectors and the replication deficient baculovirus genome. This introduction may be carried out with techniques widely described in the prior art. It is possible to cite notably the calcium phosphate technique, the DEAE dextran technique, electroporation, methods based on osmotic shock, microinjection or methods based on the use of liposomes, preferably lipofection. The method according to the invention is particularly advantageous because it makes it possible to introduce the n transfer vectors and the replication deficient baculovirus genome in a single step into the insect cell. The quantities of replication deficient baculovirus genome and transfer vectors introduced into the insect cell may vary. It is preferred to employ a quantity 5 times greater of each of the n transfer vectors with respect to the quantity of replication deficient baculovirus genome. The replication deficient baculovirus genome is advantageously introduced into the insect cell in circular form, that is to say without having been linearized beforehand. Linearization is unnecessary since the baculovirus genome is replication deficient, even in circular form since it comprises non-functional genes essential for viral replications. The absence of linearization step is one of the major advantages of the method of the invention.

As detailed above, the protein maturation enzyme may be selected from a peptidase signal, a furin, a proprotein convertase, a glycosyltransferase, a glycosidase, a protein chaperone, a disulphide isomerase, an acyltransferase, a methyltransferase, a hydroxylase, a transglutaminase, a farnesyltransferase, a geranylgeranyl-transferase, a N-myristoyltransferase, a palmityltransferase, a protein kinase, a phosphatase, a transpeptidase, a carboxylase or a ubiquitin ligase.

The choice of the protein maturation enzyme(s) will depend on the polypeptides of interest, notably the type of maturation that the polypeptides of interest will have to undergo. For example, when the polypeptides of interest form the sub-units of a glycosylated protein of interest, for example an antibody, the maturation enzyme(s) may be one or more glycosyltransferase(s) enabling to obtain the desired glycosylation. Those skilled in the art could easily select suitable glycosyltransferase(s) as a function of the desired glycosylation. For example, the glycosyltransferase(s) may be chosen from N-acetylglucosaminyltransferase I, II, II, IV, V; VB, VI, IX, a galactosyltransferase (e.g. a beta-1,4-galactosyltransferase, for example selected from beta-1,4-galactosyltransferase 1, 2, 3, 4, 5, 6 and 7), CMP-NeuAc synthase, NeuAc synthase, a sialyltransferase (e.g. α2,3 sialyltransferase or α2,6 sialyltransferase), protein-O-mannosyltransferases 1 and 2, protein-O-fucosyltransferases 1 and 2, protein-O-glucosyltransferase 1, protein-O-GlcNAc transferase, GalNAc transferase, fucosyltransferases 1, 2, 3, 4, 5, 6, 7, 8, 9, 10 and 11 (FUT1 to FUT11).

In a particular embodiment, the glycosyltransferase is one or more glycosyltransferase(s) chosen from N-acetylglucosaminyltransferase II, a beta-1,4-galactosyltransferase and a sialyltransferase.

Step a1

In a particular embodiment, the replication deficient baculovirus genome of step a1) is prepared, in a bacterial cell, by homologous recombination between:
  i) a replication deficient baculovirus genome in which n genes essential for viral replication are non-functional, and
  ii) one or more nucleotide sequence(s) each comprising one or more transgene(s) each encoding a protein maturation enzyme.

Thus, in this particular embodiment, the method of the invention comprises the steps of:
  a') Preparing, in a bacterial cell, a first replication deficient baculovirus genome in which n genes essential for viral replication are non-functional and which comprises one or more transgene(s) each encoding a protein maturation enzyme, by homologous recombination between:
    a'1) a replication deficient baculovirus genome in which n genes essential for viral replication are non-functional, and a'2) one or more nucleotide sequence(s) each comprising one or more transgene(s) each encoding a protein maturation enzyme;
a) Preparing, in an insect cell, a second baculovirus genome capable of replicating which comprises one or more transgene(s) each encoding a protein maturation enzyme and n transgenes each encoding a polypeptide of interest (recombinant baculovirus genome), by homologous recombination between:
  a1) the first replication deficient baculovirus genome obtained at step a), and
  a2) n transfer vectors each comprising:
    i) a nucleotide sequence enabling to restore the function of one of the n non-functional genes essential for viral replication,
    ii) one of the n transgenes encoding a polypeptide of interest, the set of nucleotide sequences i) of the n transfer vectors being capable of restoring the replication of the first replication deficient baculovirus genome, n being an integer at least equal to 2; and
b) Generating a recombinant baculovirus in an insect cell which comprises the recombinant baculovirus genome obtained at step b).

In this embodiment, a first recombination takes place in a bacterial cell between (a'1) a replication deficient baculovirus genome in which n genes essential for viral replication are non-functional and (a'2) one or more nucleotide sequence(s) each comprising one or more transgene(s) each encoding a protein maturation enzyme.

Preferably, the transgene(s) encoding a protein maturation enzyme each recombine at the locus of a gene not essential for viral replication, preferably at the locus of a gene not essential for viral replication non-adjacent to a non-functional gene essential for viral replication. The gene not essential for viral replication is advantageously selected from ptp (ORF1), ctx (ORF3), ORF4, ORF7, odv-e26 (ORF16), ORF17, ORF18, ORF19, ARIF-1 ORF20-21, pif2 (ORF22), protein F (ORF23), iap1 (ORF27), lef6 (ORF28), ORF29, ORF30, sod (ORF31), fgf (ORF32), gta (ORF42), ORF43, ORF44, ORF45, odv-e66 (ORF46), ORF47, ORF56, ORF57, chaB-like (ORF58/59), chaB-like (ORF60), mtase (ORF69), hcf-1 (ORF70), iap2 (ORF71), ORF86, ORF87, ORF111, ORF114, pif3 (ORF115), ORF116, ORF117, pif1 (ORF119), ORF120, ORF121, ORF122, pk2 (ORF123), ORF124, lef7 (ORF125), chitinase (ORF126), gp16 (ORF130), p35 (ORF135), p26 (ORF136), p10 (ORF137), p74 (ORF138), ORF149, ORF150, ie2 (ORF151), pe38 (ORF153) and ORF154.

In this particular embodiment, the bacterial cell is a bacterium which supports the replication of baculovirus genomes containing a mini-F origin of replication. The bacterial cell is preferably E. coli, notably DH10B or EL350.

Step b)

Step b) consists in generating a recombinant baculovirus in an insect cell which comprises the recombinant baculovirus genome obtained at step a). For example, it may be the insect cell of step a).

Advantageously, the insect cell is cultured in suitable conditions so that it expresses the recombinant baculovirus, notably in a culture medium suited to the growth of the cells. The culture medium may contain a serum of animal origin or may be a culture medium without serum.

Advantageously, the insect cell is selected from Sf9, Sf21, Tn5-b14, Lepidoptera cell lines sensitive to baculovirus AcMNPV, lines Sf21, the "High Five" line, preferably it is Sf9.

The recombinant baculovirus thus generated may be used to infect other insect cells. These insect cells infected by the recombinant baculovirus may then each produce transgenes. This production of each of the transgenes thus makes it possible to obtain the n polypeptides of interest having been matured by the protein maturation enzyme(s).

In a particular embodiment, the recombinant baculovirus may be used to infect eukaryotic cells. It has in fact been shown that the baculovirus could infect eukaryotic cells.

The method according to the invention thus makes it possible to produce easily and rapidly a recombinant baculovirus whose genome comprises one or more transgene(s) each encoding a protein maturation enzyme and n distinct transgenes each encoding a distinct polypeptide of interest.

Recombinant Baculovirus

The present invention also aims to protect a recombinant baculovirus or recombinant baculovirus genome comprising:
a) one or more transgene(s) each encoding a protein maturation enzyme, and
b) n nucleotide sequences of formula (I):

[transgene encoding a polypeptide of interest]–
[spacer nucleotide sequence]–[gene essential for
functional viral replication]     (I), said spacer nucleic acid sequence is constituted of 0 to 600 pb, preferably 1 to 600 pairs of bases,
said gene essential for functional viral replication is selected from 1629 (ORF9), Pk1 (ORF10), lef-1 (ORF14), ORF34, lef-11 (ORF37), p47 (ORF40), lef8 (ORF50), DNAJ domain (ORF51), ORF53, vp1054 (ORF54), Lef-9 (ORF62), DNA Pol (ORF65), lef-3 (ORF67), ORF73, ORF75, ORF81, p95 (ORF83), vp39 (ORF89), lef-4 (ORF90), p33 (ORF92), helicase (ORF95), Vp80 (ORF104), ORF106-107, odv-ec43 (ORF109), gp64/67 (ORF128), ORF132, ORF133, odv-ec27 (ORF144), ORF146, ie1 (ORF147), lef-2 (ORF6);
n being an integer at least equal to 2.

Advantageously, the recombinant baculovirus or the recombinant baculovirus genome according to the invention does not comprise a nucleic acid sequence which enables it to replicate within a bacterial cell. It has in fact been demonstrated that the absence of such a sequence makes it possible to increase the stability of the recombinant baculovirus, compared to a recombinant baculovirus comprising such a sequence (Piljmann et al. (2003) Journal of General Virology).

Advantageously, the recombinant baculovirus or recombinant baculovirus genome according to the invention does not comprise n genes not essential for viral replication chosen from Ph (ORF 8), ORF11, ORF13, egt (ORF15), v-ubiquitin (ORF35), 39K (ORF36), ORF38, p43 (ORF39), lef-12 (ORF41), pcna (ORF49), ORF52, ORF55, Fp (ORF61), ORF63, gp37 (ORF64), ORF68, ORF72, ORF74, ORF82, cg30 (ORF88), ORF91, pif-4 (ORF96), he65 (ORF105), ORF108, ORF110, cathepsin (ORF127), p24 (ORF129), pp34 (ORF131), ORF134, ORF145, odv-e56 (ORF148), ORF5. Advantageously, one of the n genes not essential for viral replication not comprised in the recombinant baculovirus or recombinant baculovirus genome is the gene encoding cathepsin because it has been shown that cathepsin may have a deleterious effect on the polypeptides of interest produced.

According to the invention, n is an integer at least equal to 2, for example an integer ranging from 2 to 30, for example ranging from 2 to 10, and more specifically being equal to 2, 3 or 4, as detailed in the section "Method for preparing the recombinant baculovirus" above.

According to a particular embodiment of the invention, n is greater than or equal to 3.

The present invention also aims to protect a recombinant baculovirus or a recombinant baculovirus genome, capable of being obtained by the production method according to the invention, comprising:
a) one or more transgene(s) each encoding a protein maturation enzyme, and
b) n nucleotide sequences of formula (I):

[transgene encoding a polypeptide of interest]–
[spacer nucleotide sequence]–[gene essential for
functional viral replication]          (I), said spacer nucleic acid sequence is constituted of 0 to 600 pb, preferably 1 to 600 pairs of bases, said gene essential for functional viral replication is selected from 1629 (ORF9), Pk1 (ORF10), lef-1 (ORF14), ORF34, lef-11 (ORF37), p47 (ORF40), lef8 (ORF50), DNA) domain (ORF51), ORF53, vp1054 (ORF54), Lef-9 (ORF62), DNA Pol (ORF65), lef-3 (ORF67), ORF73, ORF75, ORF81, p95 (ORF83), vp39 (ORF89), lef-4 (ORF90), p33 (ORF92), helicase (ORF95), Vp80 (ORF104), ORF106-107, odv-ec43 (ORF109), gp64/67 (ORF128), ORF132, ORF133, odv-ec27 (ORF144), ORF146, ie1 (ORF147), lef-2 (ORF6);
n being an integer at least equal to 2.

Advantageously, the n nucleotide sequences of formula (I) are spread out over the whole the genome of the recombinant baculovirus, which makes it possible to improve the stability thereof. The n nucleotide sequences of formula (I) are thus sufficiently spaced apart on the genome of the baculovirus. Advantageously, each of the n nucleotide sequences of formula (I) is spaced apart by at least 500 nucleotides with respect to another of the n nucleotide sequences of formula (I). Obtaining a recombinant baculovirus or a recombinant baculovirus genome with n nucleotide sequences of formula (I) spread out over the whole the genome does not present any particular difficulty for those skilled in the art since the distribution on the genome will be linked to the "essential gene/non-essential gene" couples that will be chosen.

Advantageously, and this is inherent in the implementation of the preparation method according to the invention, the n nucleotide sequences of formula (I) are not duplicated on the genome of the recombinant baculovirus. A decrease in the stability of the recombinant baculovirus when the sequences are duplicated on the genome (data not presented) has in fact been demonstrated.

Set of Homologous Recombination Elements

The present invention also aims to protect a set of homologous recombination elements comprising:
a) a replication deficient baculovirus genome in which n genes essential for viral replication are non-functional and which comprises one or more transgene(s) each encoding a protein maturation enzyme;
b) n transfer vectors each comprising:
i) a nucleic acid sequence enabling to restore the function of one of the n non-functional genes essential for viral replication,
ii) a transgene encoding a polypeptide of interest, n being an integer at least equal to 2.

Advantageously, the non-functional genes essential for viral replications are each adjacent to a gene not essential for viral replication, as described in the section "Method for preparing the recombinant baculovirus" above.

In a particular embodiment, the transfer vectors comprise, on either side of the expression cassette of the transgene, flanking sequences homologous to the replication deficient baculovirus genome. Advantageously, the flanking sequences of each of the transfer vectors are homologous to all or part of said non-functional gene essential for viral replication and to all or part of said gene not essential for viral replication. Advantageously, the flanking sequences have a length that may range from 10 pb (i.e. 10 pairs of bases) to 10 kb (i.e. 10,000 pairs of bases), advantageously ranging from 100 pb to 6 kb, preferably ranging from 200 pb to 6 kb and, in an entirely preferred manner ranging from 400 pb to 6 kb. The flanking sequences are described in detail in the section "Method for preparing the recombinant baculovirus" above.

Advantageously, n is an integer ranging from 2 to 31, for example ranging from 2 to 10, as detailed in the section "Method for preparing the recombinant baculovirus" above.

Cell

The present invention also aims to protect a cell comprising a recombinant baculovirus or a recombinant baculovirus genome according to the invention, or a cell comprising a set of homologous recombination elements according to the invention.

In a particular embodiment, the cell is an insect cell, preferably selected from Sf9, Sf21, Tn5-b14, Lepidoptera cell lines sensitive to baculovirus AcMNPV, lines Sf21, preferably Sf9, as described in greater detail in the section "Method for preparing the recombinant baculovirus" above.

Use

The present invention also targets the use of a recombinant baculovirus or a recombinant baculovirus genome according to the invention or a cell according to the invention for the production of n transgenes each encoding a polypeptide of interest.

The production of recombinant polypeptides of interest from a baculovirus is well described in the prior art and may easily be implemented by techniques well known to those skilled in the art.

"Mono-Recombinant" Baculovirus

In a particular embodiment, the method of the invention may be used to produce a "mono-recombinant" baculovirus, that is to say a baculovirus comprising a single transgene encoding a polypeptide of interest.

In this particular embodiment, the method for producing a recombinant baculovirus of which the genome comprises one or more transgene(s) each encoding a protein maturation enzyme and a transgene encoding a polypeptide of interest, comprises the steps of:
a) Preparing, in an insect cell, a recombinant baculovirus genome capable of replicating which comprises one or more transgene(s) each encoding a protein maturation enzyme and a transgene encoding a polypeptide of interest, by homologous recombination between:
a1) a replication deficient baculovirus genome in which n genes essential for viral replication are non-functional and which comprises one or more transgene(s) each encoding a protein maturation enzyme, and
a2) n transfer vectors each comprising a nucleotide sequence (i) enabling to restore the function of one of the n non-functional genes essential for viral replication,
one of the n vectors comprising the transgene encoding the polypeptide of interest, the set of nucleotide sequences (i) of the n transfer vectors being capable of restoring the replication of the replication deficient baculovirus genome, n being an integer at least equal to 2; and b) Generating a recombinant baculovirus in an insect cell which comprises the recombinant baculovirus genome obtained at step a).

FIGURES

FIG. 1 is a diagram which illustrates the steps of preparation of BacMid1.
Caption:
ORF: open reading frame
Polyhedrin or PH: baculovirus gene encoding polyhedrin: gene not essential for viral replication.
ORF603: baculovirus gene encoding the protein 603, non-essential gene.
ORF1629: baculovirus gene encoding the protein 1629: gene essential for viral replication
pVT: plasmid transfer vector.
Mini-F: origin of bacterial replication.
Kan®: bacterial expression cassette expressing the kanamycin resistance gene.
Amp®: bacterial expression cassette expressing the ampicillin resistance gene.
Recombination fragment: fragment of DNA containing the expression cassette to integrate in the target DNA. This fragment has flanking regions on either side of the expression cassette to be able to target specifically the region that will undergo homologous recombination via Red Recombinase.

Figure 2:
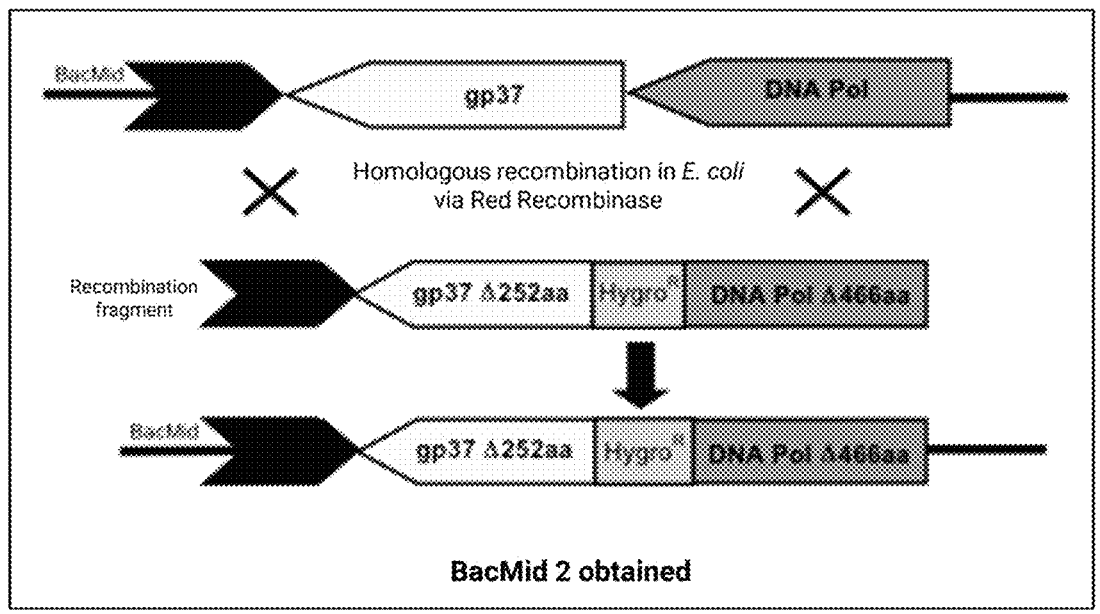

FIG. 2 is a diagram which illustrates the step of partial deletion of the gene encoding viral DNA polymerase, the gene dna pol for the preparation of BacMid2.
Caption:
gp37: baculovirus gene encoding glycoprotein gp37, gene not essential for viral replication. gp37 Δ252 aa: gene gp37 deleted from the region encoding the 252 N-terminal amino acids.
DNAPol: baculovirus gene encoding viral DNA polymerase, gene essential for viral replication.
DNAPol-Δ466 aa: dna pol gene deleted from the region encoding the 466 C-terminal amino acids.
Hygro®: bacterial expression cassette expressing the hygromycin resistance gene.
Recombination fragment: fragment of DNA containing the expression cassette to integrate in the target DNA. This fragment has flanking regions on either side of the expression cassette to be able to target specifically the region that will undergo homologous recombination via Red Recombinase.

Figure 3:
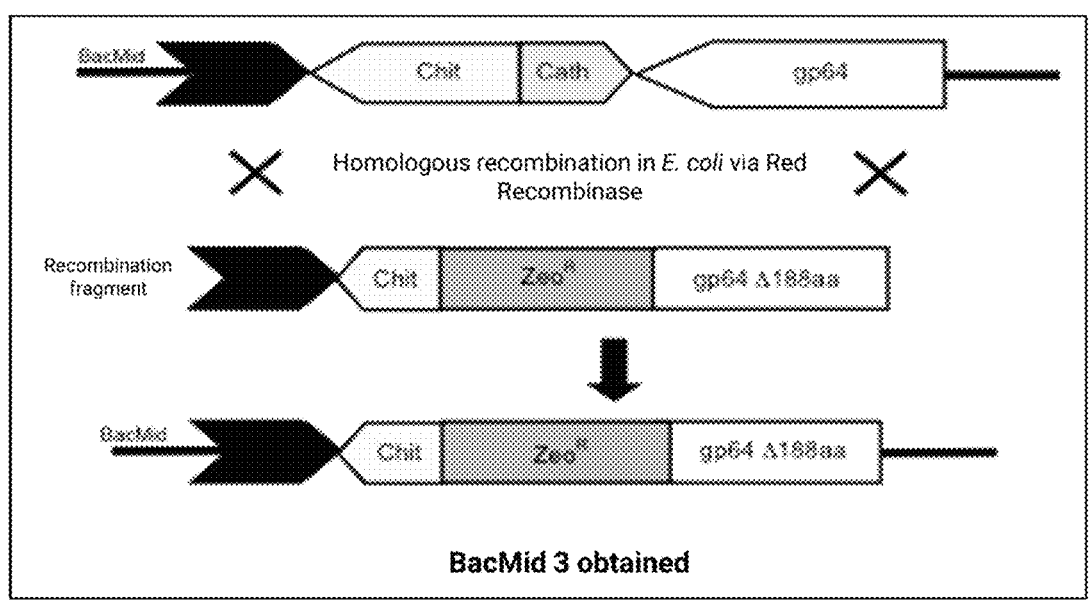

FIG. 3 is a diagram which illustrates the step of partial deletion of the gene encoding gp64 for the preparation of BacMid3.
Caption:
Chit: baculovirus gene encoding chitinase, gene not essential for viral replication.
Cath: baculovirus gene encoding viral cathepsin, gene not essential for viral replication. gp64: baculovirus gene encoding viral glycoprotein gp64, gene essential for viral replication. gp64-Δ188 aa: gene gp64 deleted from the region encoding the 188 C-terminal amino acids.
Zeo®: bacterial expression cassette expressing the zeocin resistance gene.

Recombination fragment: fragment of DNA containing the expression cassette to integrate in the target DNA. This fragment has flanking regions on either side of the expression cassette to be able to target specifically the region that will undergo homologous recombination via Red Recombinase.

Figure 4:
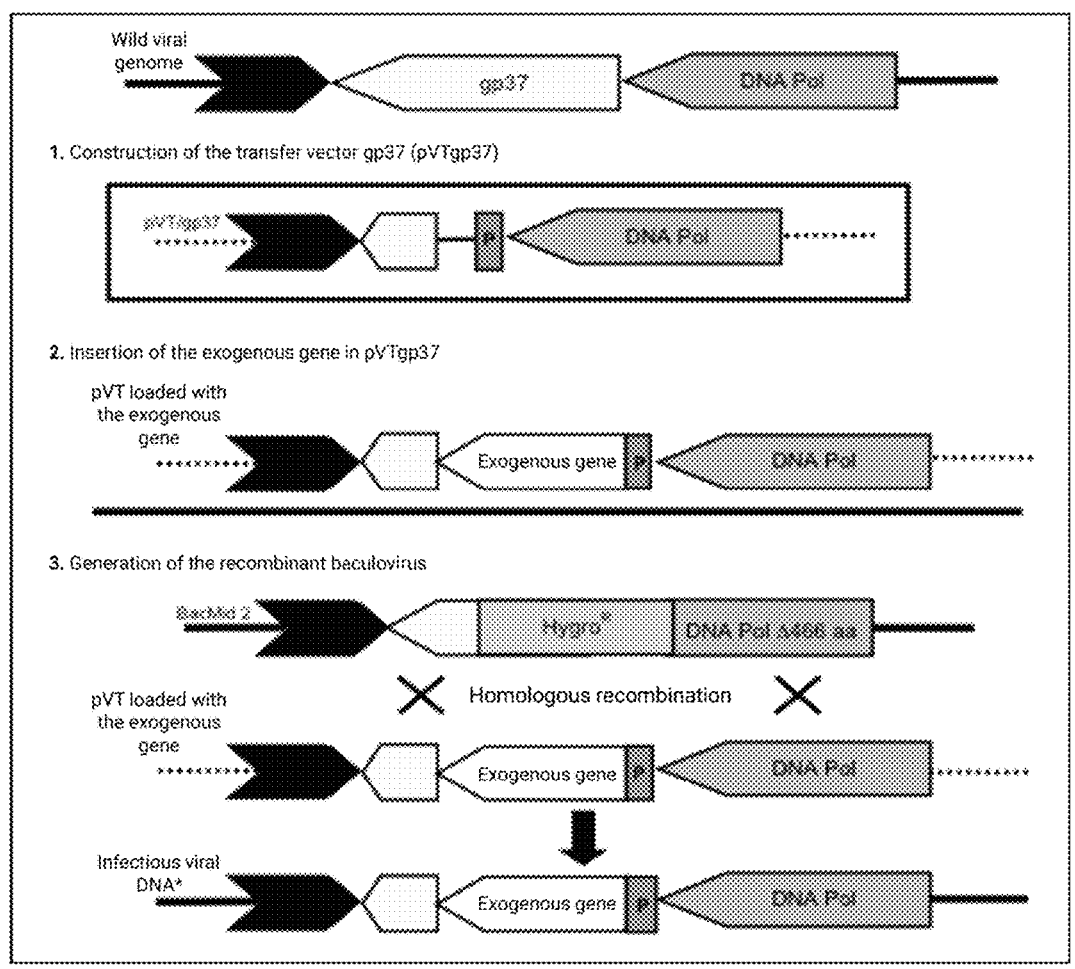

FIG. 4 is a diagram which illustrates the transfer vector pVT/gp37 and its use with BacMid2 for the generation of a recombinant baculovirus genome comprising a transgene X.
Caption:
pVT: plasmid transfer vector.
gp37: baculovirus gene encoding the glycoprotein gp37, gene not essential for viral replication.
DNAPol: baculovirus gene encoding viral DNA polymerase, gene essential for viral replication.
DNAPol.Δ466 aa: dna pol gene deleted from the region encoding the 466 C-terminal amino acids.
Exogenous gene: transgene of interest.
P: viral or cellular promoter which controls the expression of the transgene.
Hygro®: bacterial expression cassette expressing the hygromycin resistance gene.

Figure 5:
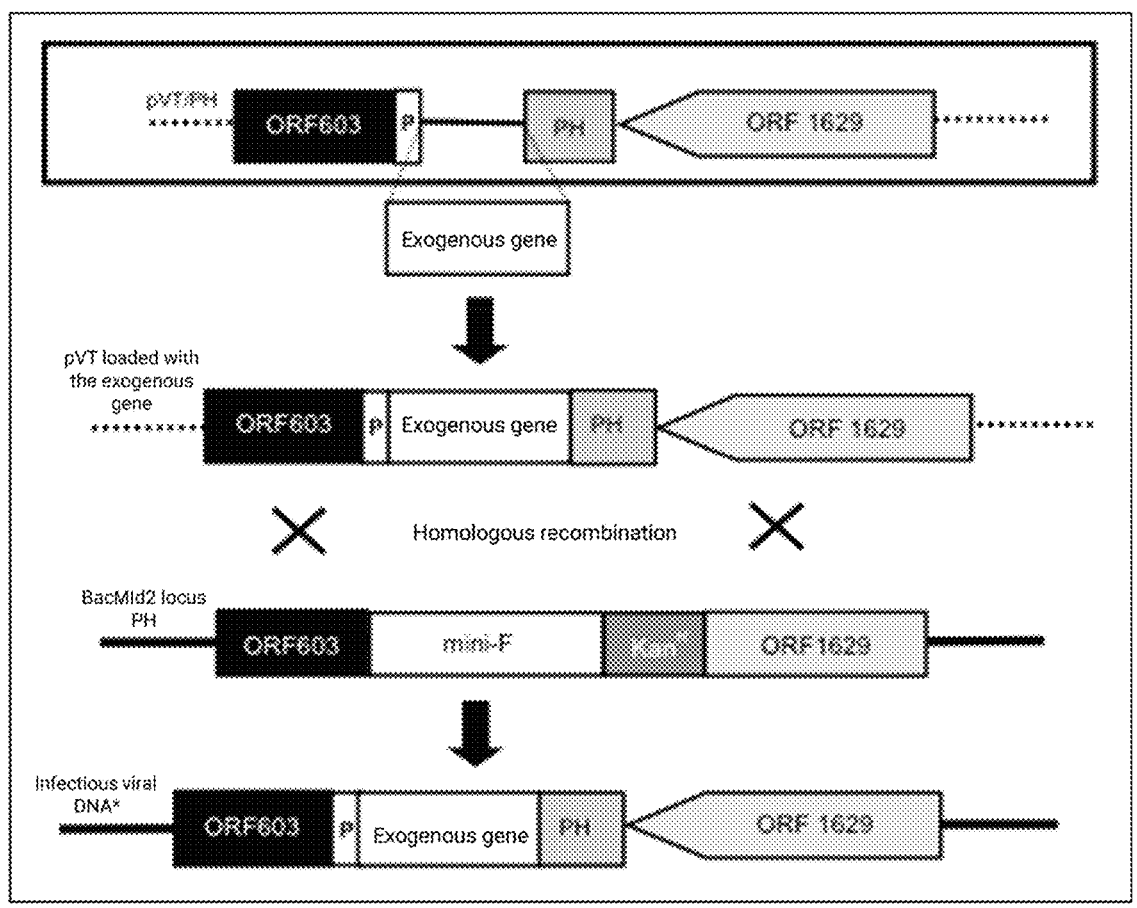

FIG. 5 is a diagram which illustrates the construction and the use of the transfer vector PH pVT/PH with BacMid2 and for the generation of a recombinant baculovirus genome comprising a transgene X.
Caption:
pVT/PH: polyhedrin transfer vector plasmid.
PH: all or part of the baculovirus gene encoding polyhedrin, gene not essential for viral replication.
ORF603: baculovirus gene encoding protein 603, non-essential gene.
ORF1629: baculovirus gene encoding protein 1629, gene essential for viral replication.
Exogenous gene: transgene of interest.
P: viral or cellular promoter which controls the expression of the transgene.
Kan®: bacterial expression cassette expressing the kanamycin resistance gene.
Mini-F: origin of bacterial replication.

FIG. 6 is a diagram which illustrates the construction and the use of the transfer vector pVT/gp37Cγ' with BacMid2 for the generation of a recombinant baculovirus genome comprising the heavy chain of an antibody.
Caption:
pVT: plasmid transfer vector.
pVT/gp37-Cγ1: plasmid transfer vector specific to the heavy chain of an immunoglobulin.
Cγ1: DNAc encoding the constant domain γ1 of a human immunoglobulin.
VH: DNAc encoding the variable domain of the heavy chain of an immunoglobulin.
DNAPol: baculovirus gene encoding viral DNA polymerase, gene essential for viral replication.
DNAPolΔ466 aa: DNAPol gene deleted from the region encoding the 466 C-terminal amino acids.
P: viral or cellular promoter which controls the expression of the transgene.
Hygro®: bacterial expression cassette expressing the hygromycin resistance gene.
PS: DNAc encoding a signal sequence (secretion of the heavy chain).

Figure 7:
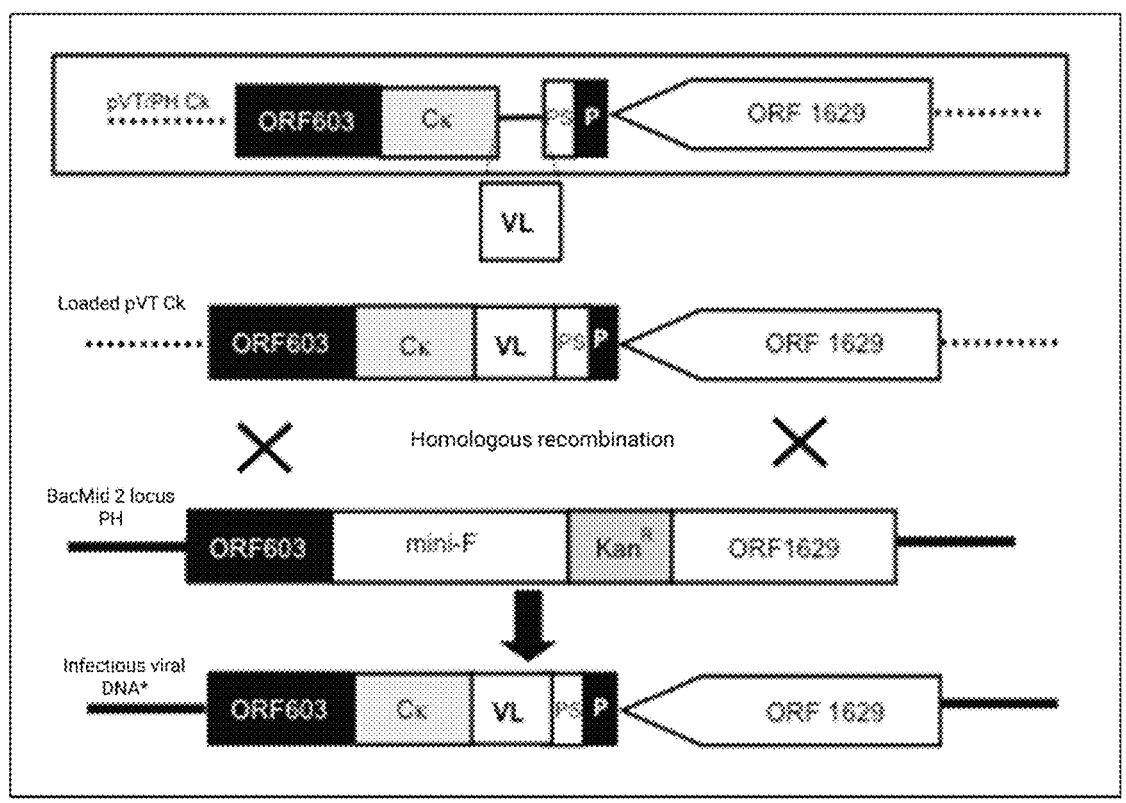

FIG. 7 is a diagram which illustrates the construction and the use of the transfer vector pVT/PHCκ with BacMid2 for the generation of a recombinant baculovirus genome comprising the light chain of an antibody.

Caption:
- ORF603: baculovirus gene encoding protein 603.
- ORF1629: baculovirus gene encoding protein 1629: gene essential for viral replication.
- Mini-F: origin of bacterial replication.
- pVT: plasmid transfer vector.
- pVT/PH-Cκ: plasmid transfer vector specific to the light chain of an immunoglobulin.
- Cc: DNAc encoding the kappa constant domain of a human immunoglobulin.
- VL: DNAc encoding the variable domain of the light chain of an immunoglobulin.
- P: viral or cellular promoter which controls the expression of the transgene.
- Kan®: bacterial expression cassette expressing the kanamycin resistance gene.
- PS: DNAc encoding a signal sequence (secretion of the light chain).

Figure 8:
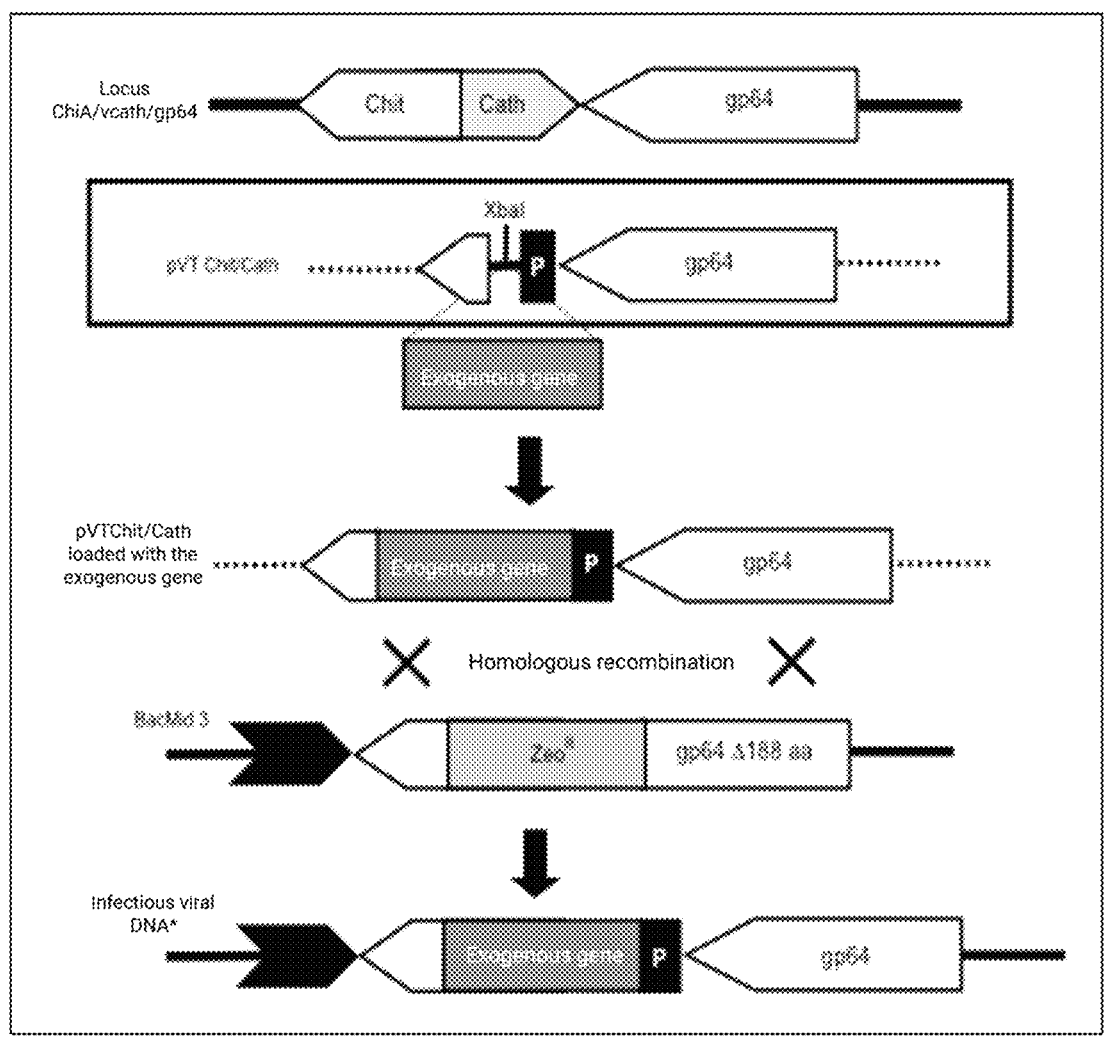

FIG. 8 is a diagram which illustrates the construction of the vector pVT/Chit-Cath and its use with BacMid3 and the generation of a recombinant baculovirus genome comprising a transgene.

Caption:
- pVT Chit/Cath: plasmid transfer vector capable of recombining at the locus of the region comprising the 2 non-essential genes, ChiA encoding chitinase and Cath encoding cathepsin.
- gp64Δ188 aa: gp64 gene, essential gene, deleted from the region encoding the 188 C-terminal amino acids.
- Exogenous gene: transgene of interest.
- P: viral or cellular promoter which controls the expression of the transgene.
- Zeo®: bacterial expression cassette expressing the zeocin resistance gene.

Figure 9:
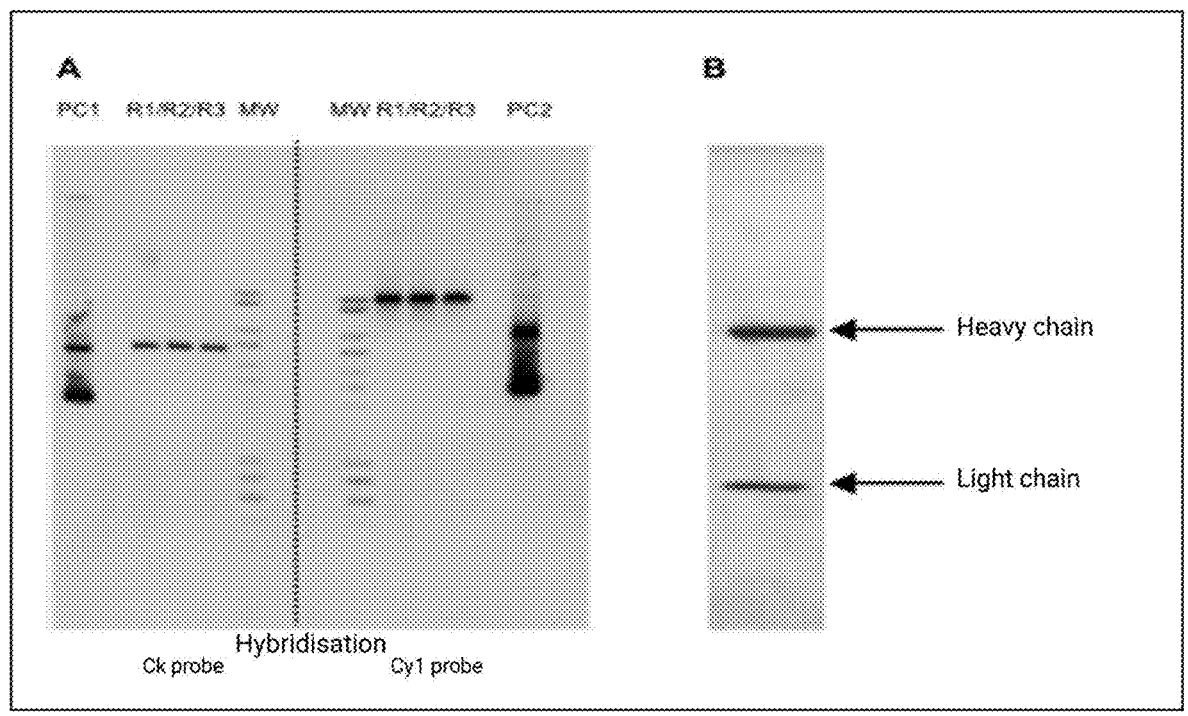

FIG. 9 is A) analysis by Southern blot of the genome of 3 purified independent recombinant baculoviruses, generated during the same transfection, and B) analysis of the recombinant antibodies after purification on Protein A Sepharose (GE Healthcare).

Caption:
- A: analysis of the organisation of the genomes of 3 independent recombinant baculoviruses expressing the antibodies 13B8II. These baculoviruses were isolated from a single transfection experiment. The hybridizations carried out respectively with a probe specific to the constant region of the kappa light chain: probe Cκ and a probe specific to the constant region of the heavy chain gamma 1: probe Cγ1 demonstrates a correct and identical organisation of the 3 recombinant viruses.
- B. Analysis by electrophoresis in polyacrylamide gel (SDS, 2-mercaptoethanol) and silver staining of the purified recombinant antibodies. The antibodies secreted in the culture medium of cells infected with the recombinant baculovirus were purified on a Protein A Sepharose column.
- PC1: Plasmid control, plasmid containing the gene of the kappa light chain,
- PC2: Plasmid control, plasmid containing the gene of the heavy chain γ1, R1-3, recombinant baculovirus 1, 2 and 3,
- MW: size marker.

Figure 10:
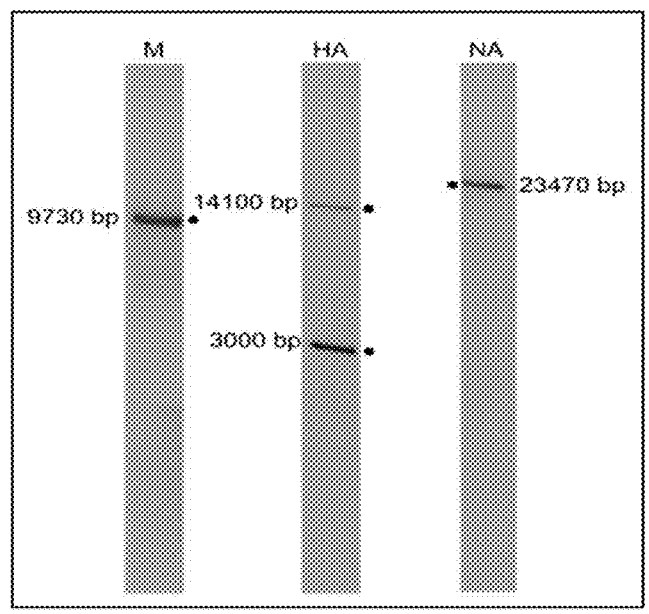

FIG. 10 is the analysis by Southern blot of the genome of a triple recombinant virus expressing the proteins M, HA and NA of the flu virus.

Caption:
- M: gene of the flu virus encoding the matrix protein.
- HA: gene of the flu virus encoding hemagglutinin.
- NA: gene of the flu virus encoding neuraminidase.
- bp: size of the DNA fragments expressed in pairs of bases.

Figure 11:
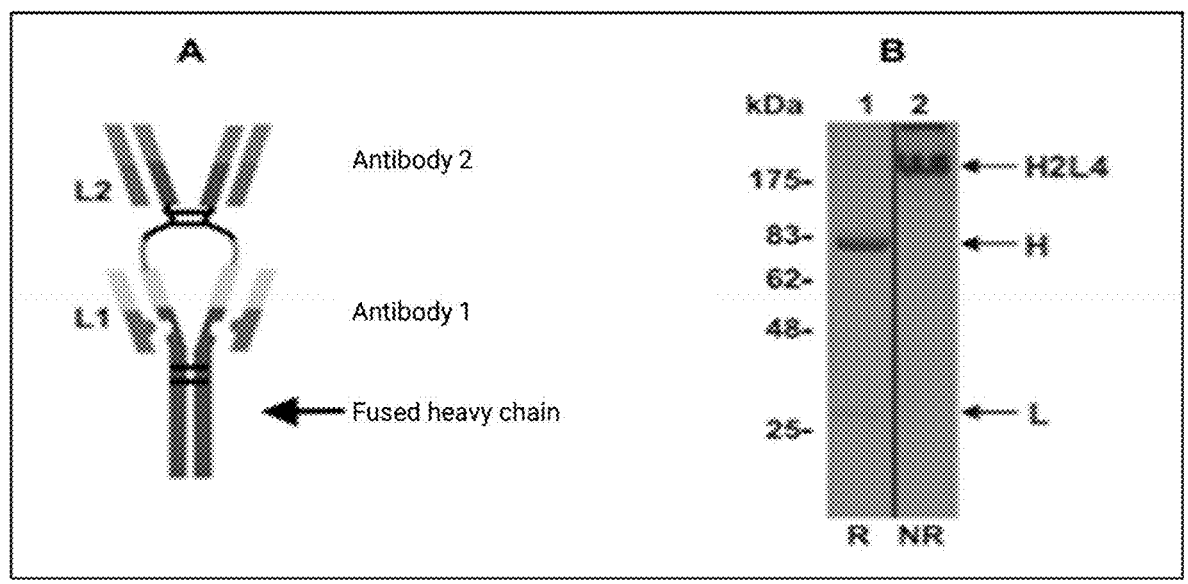

FIG. 11 is a diagram which illustrates in A the structure of the bispecific antibodies and in B the analysis by electrophoresis in polyacrylamide gel of the bispecific antibodies purified on protein A Sepharose column.

Caption:
- A: Diagrammatical representation of the structure of the bispecific antibodies. L1: light chain of the antibodies 1; L2, light chain of the antibodies 2.
- B: Purified bispecific antibodies, analysed by electrophoresis on polyacrylamide gel. The proteins were revealed by silver staining. (1) electrophoresis under reducing conditions (SDS, 2-mercaptoethanol). (2) electrophoresis under non-reducing conditions. H: heavy chain of the antibodies, L: light chain of the antibodies, H2L4: composition of the bispecific antibodies: 2 fused heavy chains bound by 4 disulphide bridges at the level of 2 hinge regions+4 light chains (2 chains L1+2 chains L2) paired in a specific manner to the corresponding regions VH1-CH1 and VH2-CH1.

Figure 12:
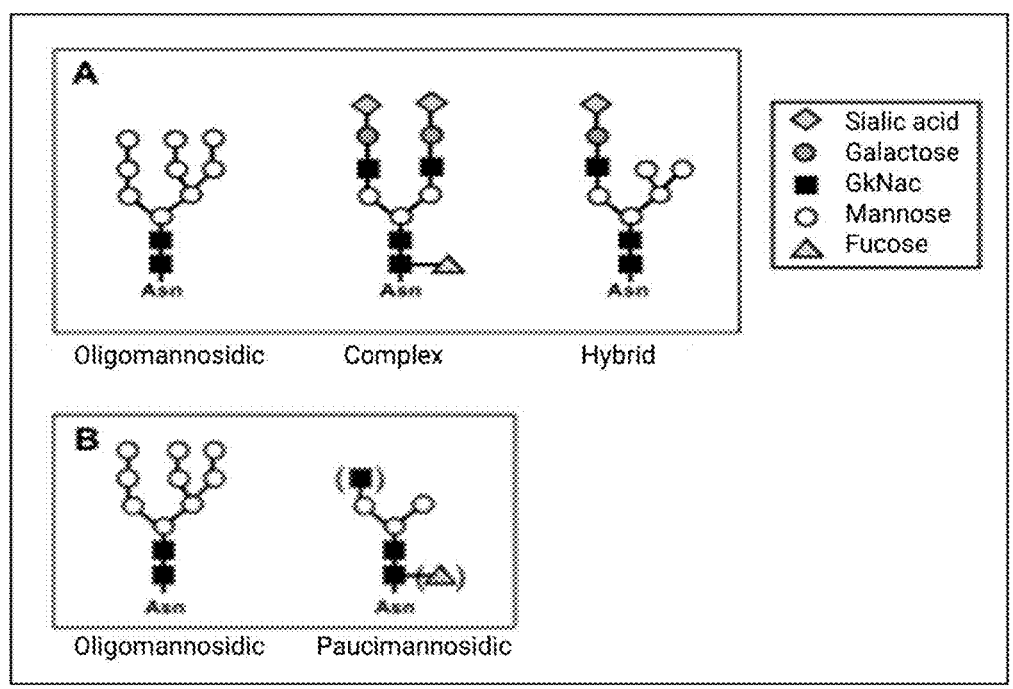
Figure 13:
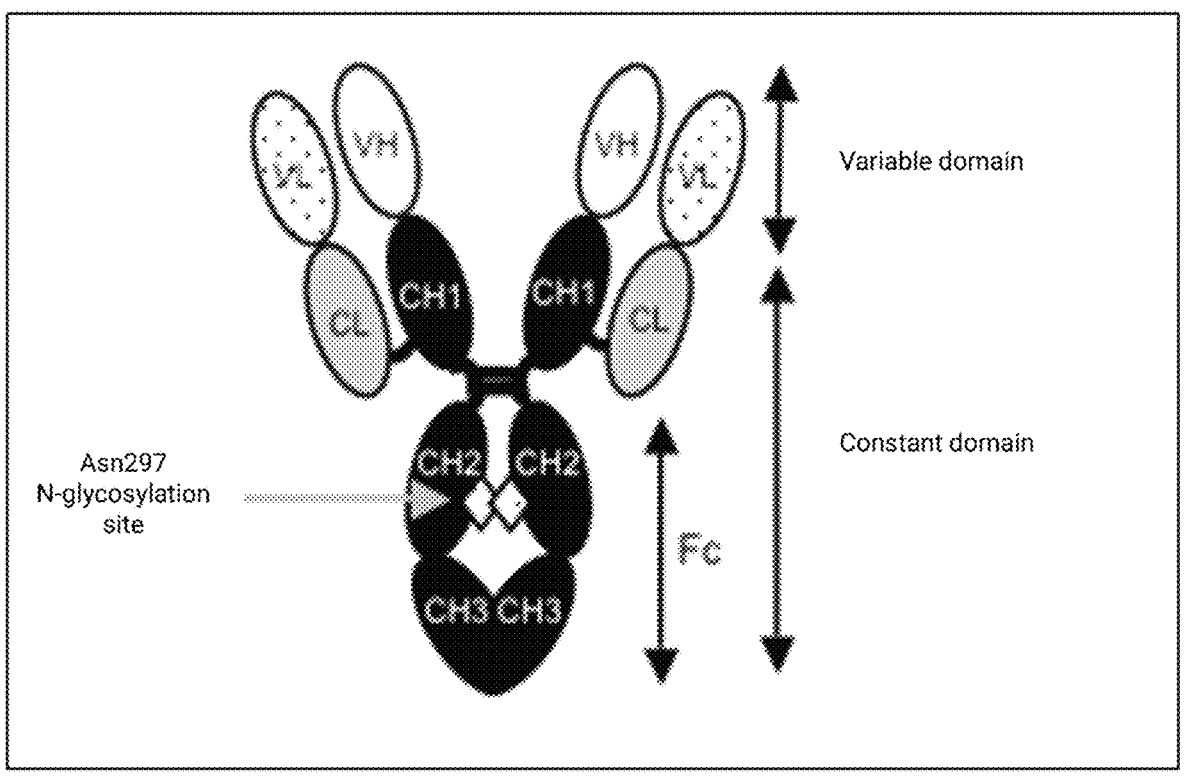

FIG. 12 is a representation of glycan structures bound to the glycoproteins synthesised by (A) human cells and (B) lepidoptera cells.

FIG. 13 is a representation of a human immunoglobulin (IgG). The asparagine residue 297, (Asn297) bound to an N-glycan is represented by a lozenge. The nature of this N-glycosylation, like the presence of galactose and sialic acid, may be an important element of the structure of the antibodies since it enables a modulation of certain effector activities, for example ADCC and CDC.

Figure 14:
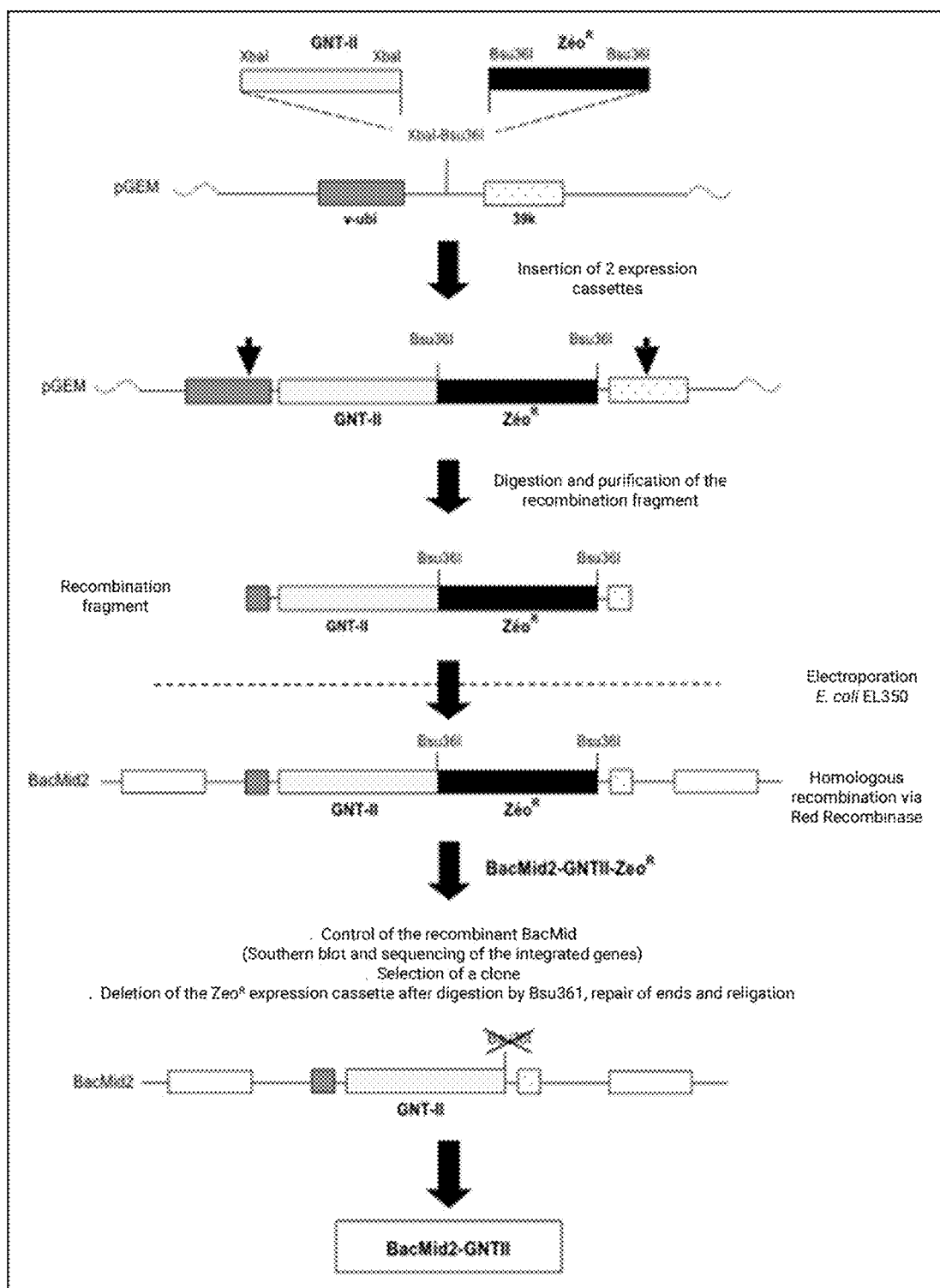

FIG. 14 is a representation of the different steps necessary for the construction of a BacMid2/MPT (MPT: Post Translational Modification) that is to say a BacMid2 of which the genome comprises a transgene each encoding a glycan biosynthesis enzyme—or more generally a BacMid2 of which the genome comprises one or more transgene(s) each encoding a protein maturation enzyme.

FIG. 14 specifically exemplifies the integration of a transgene encoding GNT-II in the intergenic region orf35 (v-ubi)-orf36(39k) (IG35/36) of BacMid2.

Two expression cassettes were successively inserted into the region IG35/36 cloned beforehand in a plasmid pUC (i) a viral expression cassette, composed of an early viral promoter (see Table 2) and the gene encoding GNT-II and (ii) a bacterial expression cassette controlling the zeocin resistance gene (Zeo®). A "recombination fragment" containing the 2 cassettes was generated by digestion of the above plasmid by 2 restriction endonucleases. The latter was introduced into the bacterium EL350/BacMid2 by electroporation. A homologous recombination took place via Red Recombinase between the flanking regions of the recombination fragment and the DNA of BacMid2 enabling the integration of the 2 expression cassettes. The recombinant bacteria thus obtained were selected with zeocin then the gene encoding the resistance to this antibiotic was eliminated from the DNA of the bacmid by simple digestion/reparation/relegation. The bacmid obtained, called BacMid2-GNTII, was re-introduced by electroporation into a bacterium EL350 (EL350/BacMid2-GNT-II).

FIG. 15 shows BacMid2-fur and BacMid2Gal-Fur.
- A and B: Control of the genomic organisation of BacMids BacFur and BacGal-Fur. A. The DNA of the 2 bacmids was digested by EcoRI, the fragments generated were separated on agarose gel at 1% then stained with ethidium bromide. B. The DNA was transferred onto a nylon membrane according to the Southern technique.

The membranes were incubated with a probe specific to the gene fur expressed by the Sf9 cell.

Caption:
  A, Agarose gel stained with ethidium bromide, Well 1: restriction profile EcoRI of BacMid2Gal-Fur, Well 2: Restriction profile EcoRI of BacMid2-Fur. B. Southern blot, Well 1: restriction profile EcoRI of BacMid2Gal-Fur, Well 2: restriction profile EcoRI of BacMid2-Fur.
  C and D: two recombinant viruses co-expressing the polyprotein Pr55Gag and gp160 of the virus HIV-1 were constructed one from BacMid2 and the other from BacMid2-Fur. The Sf9 cells were infected for 48 hours with the different viruses and the proteins secreted in the culture supernatant were concentrated or not with a solution of "Retro Concentin™ Virus Precipitation (SBI, reference RV100A-1)" then deposited on a polyacrylamide gel at 10% under denaturing and reducing conditions then analysed by Western blot. C. The proteins were revealed with an anti-gp120 antibody (reference Ab21179, Abcam). D. The proteins were revealed with an anti-Pr55$^{Gag}$ antibody (reference. 63917, Abcam).

Caption:
  BACWT: wild baculovirus, BACgp160/Gag/Fur: triple-recombinant baculovirus expressing gp160 and polyprotein Pr55$^{Gag}$ of HIV-1 as well as the furin of the cell Sf9 BACgp160/Gag: double-recombinant baculovirus expressing gp160 and polyprotein Pr55$^{Gag}$ of HIV-1, BACgp120: mono-recombinant baculovirus expressing gp120 of HIV-1, BACGag: mono-recombinant baculovirus expressing polyprotein Pr55$^{Gag}$ of HIV-1.

FIG. 16 is a representation of the principle of use of BacMid2-Gal (BacGal) for the generation of double- or mono-recombinant baculovirus genomes.
  A. Generation of a double-recombinant baculovirus genome.
    The 2 transgenes of interest are cloned in their respective transfer vector, pVT/PH targeting the couple GNE/GE PH/1629 and pVT/gp37 targeting the couple GNE/GE gp37/DNAPol. The Sf9 cells are transfected with 2 pVT and DNA of BacMid2-Gal. During homologous recombination, the 2 transgenes of interest are integrated in the genome of BacMid2-Gal whereas simultaneously the non-functional genes 1629 and dnapol borne by BacMid2-Gal are replaced by a functional copy. These events will have for consequence the elimination of the origin of bacterial replication and the generation of an infectious recombinant baculovirus genome. Recombinant baculoviruses are then produced and secreted in the culture medium, then cloned by the phage plaque assay method.
  B. Generation of a mono-recombinant baculovirus genome.
    The gene of interest is cloned in the transfer vector pVT/gp37. The Sf9 cells are transfected with pVT/gp37 comprising a transgene, pVT/PH not containing transgene and DNA of BacMid2-Gal. During homologous recombination, there is repair of the bacmid in the 2 loci and thus generation of infectious baculovirus.

Caption:
  GE: Essential gene
  GNE: Non-essential gene
  pVT/PH: Transfer vector which targets the couple GNE/GE PH/1629
  pVT/gp37: Transfer vector which targets the couple GNE/GE gp37/DNAPol
  DNA Pol$^{NF}$: Gene encoding non-functional viral DNA polymerase
  DNA Pol$^{F}$: Gene encoding functional viral DNA polymerase
  1629$^{NF}$: Gene encoding the non-functional protein 1629
  1629$^{F}$: Gene encoding the functional protein 1629
  β1,4 GalT: β1,4 galactosyltransferase
  GNT-II: N acetylglucosaminyltransferase II
  Kan®: kanamycin resistance gene
  mini-F: origin of bacterial replication
  PH: polyhedrin gene FIG. 17 is a representation of the principle of the preparation of a double-recombinant baculovirus genome expressing a galactosylated antibody. The Sf9 cells are transfected with pVT/H (see FIG. 6), pVT/L (see FIG. 7) and DNA of BacMid2-Gal. During homologous recombination, the transgenes encoding the heavy and light chains are integrated in the genome of BacMid2-Gal whereas simultaneously the non-functional genes 1629 and dnapol borne by BacMid2-Gal are replaced by a functional copy, making the baculovirus genome infectious. Recombinant baculoviruses are then produced, secreted in the culture medium then cloned by the phage plaque assay method.

Figure 18:
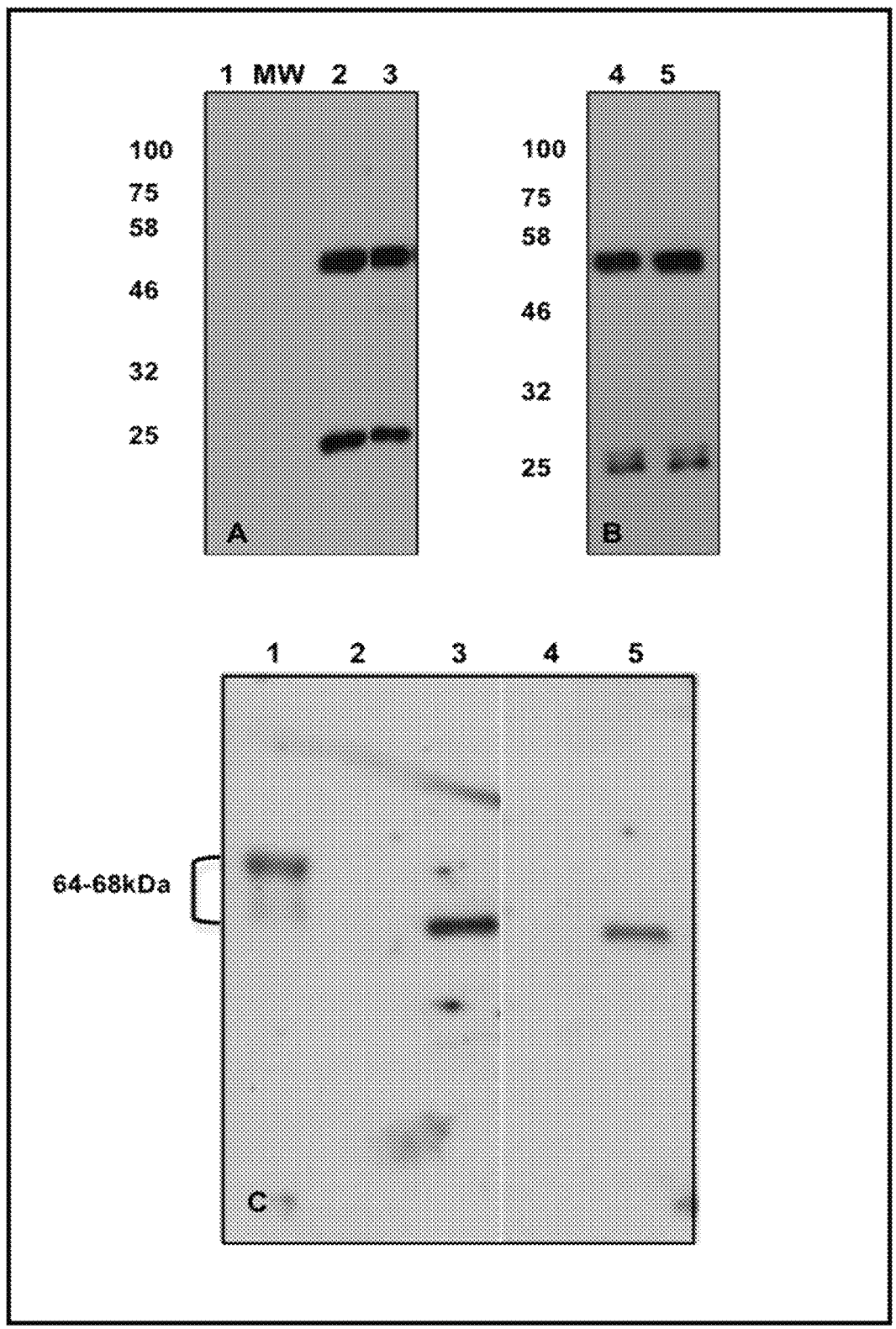

Caption:
  GE: Essential gene
  GNE: Non-essential gene
  pVT/PH: Transfer vector which targets the couple GNE/GE PH/1629
  pVT/gp37: transfer vector which targets the couple GNE/GE gp37/DNAPol
  DNA Pol$^{NF}$: Gene encoding non-functional viral DNA polymerase
  DNA Pol$^{F}$: Gene encoding functional viral DNA polymerase
  1629$^{NF}$: Gene encoding the non-functional protein 1629
  1629$^{F}$: Gene encoding the functional protein 1629
  β1,4 GalT: β1,4 galactosyltransferase
  GNT-II: N acetylglucosaminyltransferase II
  Kan®: kanamycin resistance gene
  mini-F: origin of bacterial replication
  PH: polyhedrin gene FIG. 18 represent an analysis by Western blot and lectin blot of antibodies produced by a Sf9 cell infected with a recombinant baculovirus generated from BacMid2 or BacMid2-Gal. These human antibodies (the recombinant antibodies 13B8II have a constant human domain) or mouse antibodies not having glycosylation in their paratope, the analyses thus reveal the nature of the N-glycosylation which is borne by their constant domain.

Caption:
  A and B. Western blot. A: the membrane was incubated with a sheep anti-human IgG whole antibody peroxidase conjugated (reference NA933V, GE Healthcare). B: The membrane was incubated with a sheep anti-mouse IgG whole antibody peroxidase conjugated (reference NA931V, GE Healthcare).
  A. Well 1: Fetuin (61-68 kDa), supplied in the "Dig Glycan Differentiation" kit from Roche, this α2,3 and α2,6 sialylated protein constitutes the positive control for analyses with lectin blot whether for SNA, MAA or diCBMA. According to the supplier, the molar mass (*) of this protein varies between 68 and 61 kDa, Well 2: Recombinant antibodies 13B8II/BacGal, Well 3: Recombinant antibody 13B8II/BacMan,
  B. Well 1: Recombinant mouse antibody/BacGal, Well 2: Recombinant mouse antibody/BacMan, C. Lectin blot. The membrane was incubated in the presence of $RCA_{120}$ conjugated with biotin. The presence of lectin was revealed as described in example 17.

Well 1: Fetuin (61-68 kDa) Well 2: Recombinant mouse antibody/BacMan, Well 3: Recombinant mouse, antibody/BacGal, Well 4: Recombinant antibody 13B8II/BacMan, Well 5: Recombinant antibody 13B8II/BacGal.

FIG. 19 is a diagram which describes the use of BacMid2-Sia for the preparation of multi-recombinant baculovirus genomes and the construction of a second generation of new BacMidSia, BacMidSia6-II. In FIG. 19A, the transgenes 1 and 2 are cloned respectively in pVT/PH targeting the couple GNE/GE PH/1629 and in pVT/gp37 targeting the couple GNE/GE gp37/DNAPol. The genome of BacMid-Sia is equipped with all the genes necessary for α2,3 sialylation [α2,3 sialyltransferase] (BacMid2-Sia3 or BacSia3) or α2,6 sialylation [α2,6 sialyltransferase] (BacMid2-Sia6 or BacSia6 and BacMid2Sia6-II or BacSia6-II) or α2,3+α2,6-sialylation [α2,3 sialyltransferase+α2,6 sialyltransferase] (BacMid2-Sia3/6 or BacSia3/6) and 2 genes necessary for the biosynthesis of the sugar nucleotide CMP-NeuAC. The Sf9 cells are transfected with 2 pVT and the DNA of one of the BacMid-Sia. During homologous recombination, the 2 transgenes are integrated in the genome of BacMid2-Sia whereas, simultaneously, the non-functional genes 1629 and dnapol borne by BacMid2-Sia are replaced by a functional copy, making the baculovirus genome infectious. Recombinant baculoviruses are then produced and secreted in the culture medium then cloned by the phage plaque assay method.

Caption:
GE: Essential gene
GNE: Non-essential gene
pVT/PH: Transfer vector which targets the couple GNE/GE PH/1629
pVT/gp37: Transfer vector which targets the couple GNE/GE gp37/DNAPol
DNA Pol$^{NF}$: Gene encoding non-functional viral DNA polymerase
DNA Pol$^{F}$: Gene encoding functional viral DNA polymerase
1629$^{NF}$: Gene encoding the non-functional protein 1629
1629$^{F}$: Gene encoding the functional protein 1629
β1,4 GalT: β1,4 galactosyltransferase
GNT-II: N acetylglucosaminyltransferase II
α2,3 ST: α2,3 sialyltransferase
α2,6 ST: α2,6 sialyltransferase
Kan®: kanamycin resistance gene
mini-F: origin of bacterial replication
PH: polyhedrin gene FIG. 19B is the analysis by Southern blot of the genome of 2 clones of BacMid2Sia6-II of which the construction is described in example 14.

Caption:
a: Analysis of the electrophoretic profile of digestion by EcoRI of 2 clones of BacMid2Sia6-II (1 and 2) in comparison with BacMid2-GNTII-β1,4GT-CMP-NeuAcS-NeuAcS (T) shows that the integration of the cassette ST6GalI in the region Pif1 generates 2 fragments EcoRI of 3122 pb and 6138 pb.
b: The hybridisation carried out with a probe specific to ST6GalI makes it possible to verify the marking of the 2 fragments EcoRI of 3122 pb and 6138 pb of the control plasmid (PC), plasmid containing the ST6GalI gene and demonstrates a correct and identical organisation of the 2 BacMids obtained.

MW: Smart Ladder (Eurogentec)

Figure 20:
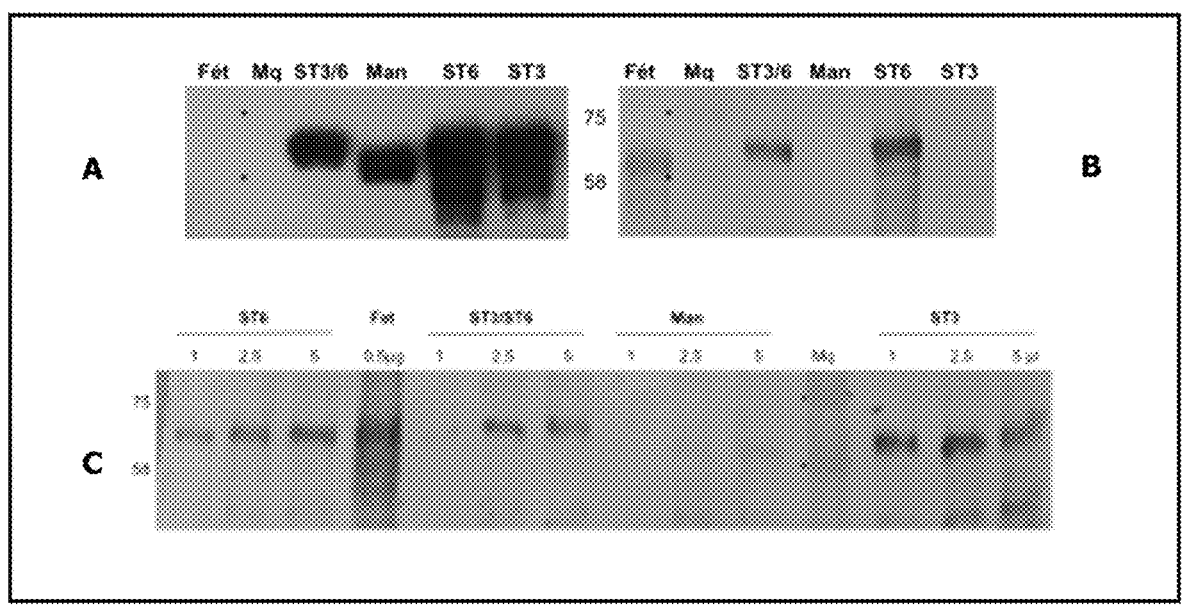

FIG. 20 represents the analysis by Western blot and lectin blot of the glycosylation of the viral protein gp64 expressed by different viruses generated from different Bacmids. The glycoprotein gp64 is the major glycoprotein of the baculovirus, it is located on the surface of the baculovirus. It has been shown that this glycoprotein is capable of being galactosylated and sialylated. The cells were infected with the different recombinant viruses. The baculoviruses secreted in the culture supernatant were sedimented then taken up by a lysis buffer to be analysed by Western blot then by lectin blot.

A. Western blot. The membrane was incubated with the antibodies anti-gp64 AcV5 (reference SC65499, Santa Cruz Biotechnology)
B and C: Lectin blot. B. The membrane was incubated in the presence of SNA, lectin which specifically recognises α2,6 bound sialic acids (C) the lectin di-CBM40 which recognises α2,3 bound sialic acids and to a lesser extent α2,6 bound sialic acids.

Caption:
Fet: Fetuin
Mq: Molecular weight markers
ST3: Virus generated from the bacmid BacSia3
ST6: Virus generated from the bacmid BacSia6
ST3/6: Virus generated from the bacmid BacSia3/6
Man: Virus generated from BacMid2

Figure 21:
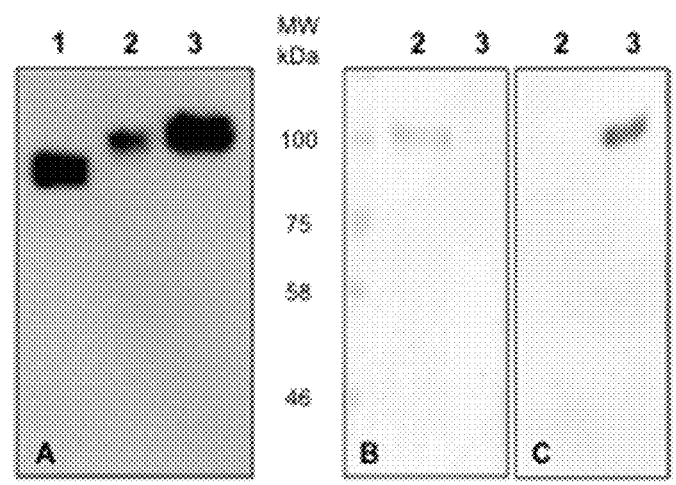

FIG. 21 represent the analysis by Western blot and lectin blot of the recombinant protein X produced thanks to a recombinant baculovirus generated from BacSia6. This protein being soluble, the analyses below were carried out on the purified protein. After electrophoresis in polyacrylamide gel then transfer onto a membrane, the protein was incubated in the presence either of a specific antibody for analysis by Western blot (A) or a lectin specific for lectin blot, SNA (B), or MAA (C).

Caption:
Well 1, the protein X was produced after infection of the Sf9 cells with a recombinant baculovirus generated from BacMid2. Well 2, the protein X was produced after infection of the Sf9 cells with a recombinant baculovirus generated from BacSia6. Well 3, commercially available Protein X produced in CHO cells. The presence of lectin was revealed as described in example 17. MW: Molecular weight marker (Pre-stained marker, Biolabs reference P7706).

Figure 22:
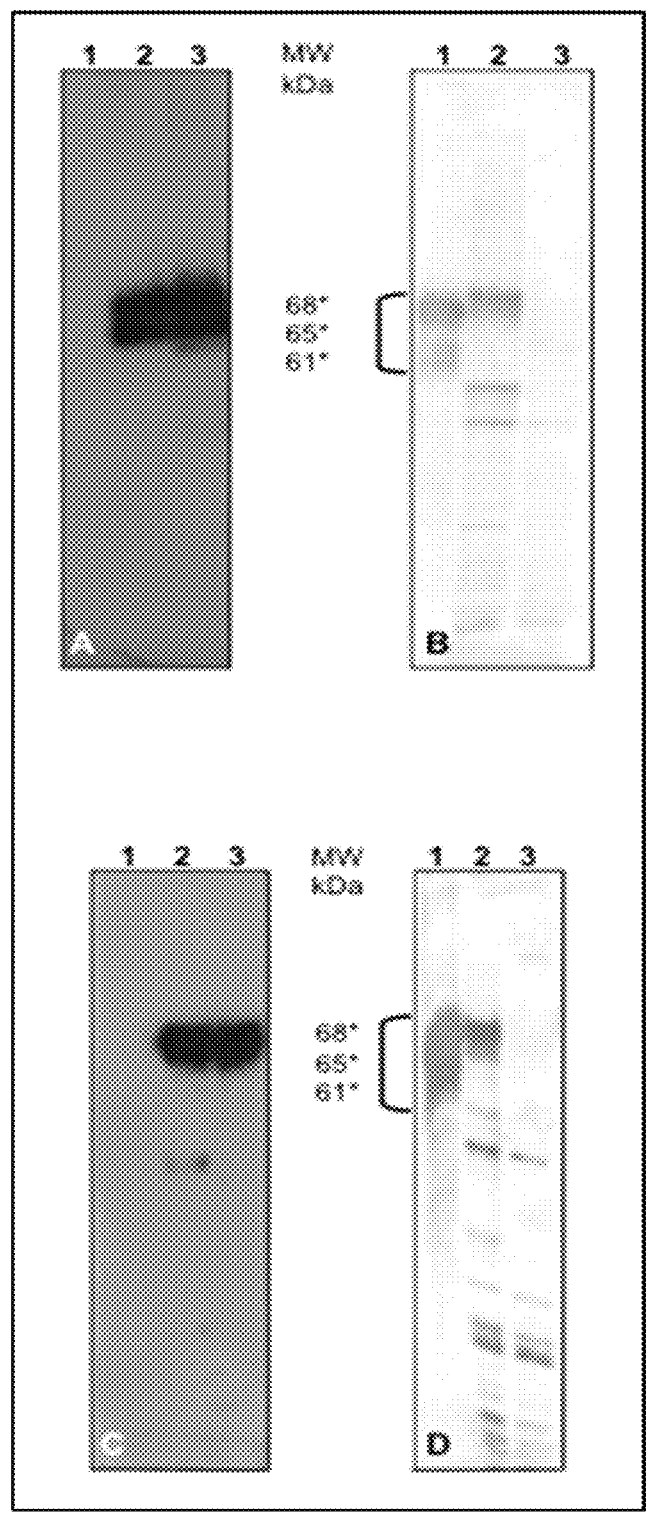

FIG. 22 represent the analysis by Western blot and lectin blot of the protein VSVg produced thanks to a recombinant baculovirus generated from BacSia6. The protein VSVg being membranal, the analyses were carried out on pellets of infected Sf9 cells.

A and B: Analysis of the Protein VSVg.
A. Western blot, after electrophoresis in polyacrylamide gel then transfer onto a membrane, the proteins were incubated in the presence of a specific antibody directed against VSVg (mouse antibodies peroxidase conjugated, reference A5977 Sigma).

Caption:
Well 1, Fetuin, Well 2, and 3, Sf9 cells infected with a recombinant baculovirus expressing the protein VSVg generated from BacSia6 (Well 2) or Bacmid2 (Well 3).
B. Lectin blot. The proteins transferred onto a nitrocellulose membrane were placed in the presence of lectin SNA (*Sambucus nigra* agglutinin) specific to residues of α2,6 bound sialic acids. The presence of lectin was revealed as described in example 17.

C and D. Analysis of the viral protein gp64.

We also verified that the recombinant baculovirus expressing sialylated VSVg was also bearing a sialylated gp64. To do so, the baculoviruses secreted in the culture supernatant were sedimented then taken up by a lysis buffer to be analysed by Western blot then by lectin blot.

C. Western blot, gp64 was revealed with a specific antibody (antibodies anti-gp64 AcV5, reference SC65499, Santa Cruz Biotechnology). D. Lectin blot. In the presence of lectin SNA as described in example 17.

Caption:

Well 1, Fetuin, Wells 2, and 3, particles of baculovirus prepared from the culture supernatants of cells infected with the recombinant baculovirus expressing protein VSVg and generated from BacMid2-Sia6 (Well 2) or a Bacmid2 (Well 3).

EXAMPLES

Examples 1 to 3 are relative to the construction of replication deficient baculoviruses, in which 1, 2 or 3 genes respectively are non-functional.

Examples 4 and 5 describe the generation of recombinant baculoviruses having integrated 2 or 3 transgenes, respectively.

Examples 6 to 8 are relative to the use of these recombinant baculoviruses having integrated 2 or 3 transgenes for the production of proteins of interest.

Examples 9 to 15 describe the construction of recombinant baculoviruses comprising transgenes encoding for protein maturation enzymes.

Examples 16 to 19 demonstrate that proteins of interest produced thanks to the baculoviruses of examples 9 to 15 have satisfactory maturation and/or glycosylation.

Example 1: Construction of a Replication Deficient Baculovirus Genome in which 1 Gene Essential for Viral Replication is Non-Functional (BacMid1)

BacMid1 has the deletion of a gene essential for viral replication, the gene 1629.
1. Integration of the Origin of Bacterial Replication in a Genome of the Baculovirus
This operation is carried out in the insect cell.

The origin of bacterial replication Mini-F was introduced into the polyhedrin locus of the baculovirus genome AcMNPV by homologous recombination in insect Sf9 cells (*Spodoptera frugiperda*). To do so, the cells were transfected with (i) a transfer vector PH (pVT/Mini-F-Kan®) in which the sequence of the gene ph was replaced by a fragment of DNA bearing the Mini-F+a bacterial expression cassette conferring kanamycin resistance (Kan®), and (ii) a baculovirus genome AcMNPV (baculovirus isolated from the lepidoptera *Autographa californica*). The baculovirus generated were purified by the phage plaque assay technique then characterised in order to confirm that they had indeed integrated the Mini-F and the expression cassette Kan®. A baculovirus was selected and was next transferred into the bacterium *E. coli* EL350, thus generating a first BacMid (BacMid0, non-deficient for viral replication in insect cells).
1. Deletion of the Essential Gene 1629

A bacterial expression cassette conferring ampicillin resistance (Amp®) and having on 5' and 3' the restriction site MauBI—site absent from the baculovirus genome AcMNPV—was integrated downstream of the bacterial expression cassette Kan® by homologous recombination in the bacterium *E. coli* EL350. In the course of this recombination, a fragment of DNA encoding the 27 C-terminal amino acids of the protein 1629 was deleted, making the protein 1629 non-functional (BacMid0/Amp®). The ampicillin resistance gene was next eliminated after digestion by MauBI then relegation, thus generating BacMid1. The genome of the baculovirus (i.e. BacMid1) is then deficient for replication in insect cells, because a gene essential for viral replication (i.e. the gene encoding the protein 1629) is non-functional. The bacteria containing BacMid1 are called hereafter "bacteria *E. coli* EL350/BacMid1".

FIG. 1 illustrates the steps of preparation of BacMid1.

Example 2: Construction of a Replication Deficient Baculovirus Genome in which 2 Genes Essential for Viral Replication are Non-Functional (BacMid2)

BacMid2 exhibits the deletion of 2 genes essential for viral replication, the gene 1629 and the gene encoding viral DNA polymerase (DNAPol). From BacMid1, the deletion of the gene DNAPol was carried out in the bacteria *E. coli* EL350/BacMid1 after electroporation of a recombination fragment of 4222 bp in which a part of the genes encoding gp37 (252 amino acids) and DNAPol (466 C-terminal amino acids) was deleted and replaced by a bacterial expression cassette enabling the production of hygromycin B phosphotransferase (Hygro®) thus conferring hygromycin resistance (Hygro®). The Hygro® gene was placed under the control of the bacterial promoter EM7 (derived from the commercially available vector pSelect-Hygro-mcs, Invitrogen), the terminator glms was introduced downstream of the Hygro® gene (Gay N. J. et al. *Biochem J.*, 1986, 234, 111-11). The bacteria containing BacMid2 (*E. coli* EL350/BacMid2) were selected for their hygromycin resistance. The baculovirus genome (i.e. BacMid2) is deficient for replication in insect cells, because two genes essential for viral replication (i.e. the gene encoding the protein 1629 and the gene encoding DNAPol) are non-functional.

FIG. 2 is a diagram which illustrates the step of deletion of a part of the gene DNAPol for the preparation of BacMid2.

Note: It is possible to use BacMid2 to produce a single protein (see Example 4). It suffices to have two transfer vectors, one providing the transgene and all or part of the deleted essential gene 1 and the other providing the wild gene corresponding to the deleted essential gene 2. The two deleted genes are repaired during homologous recombination.

Example 3: Construction of a Replication Deficient Baculovirus Genome in which 3 Genes Essential for Viral Replication are Non-Functional (BacMid3)

BacMid3 has the deletion of 3 essential genes, 1629, DNAPol and gp64. From BacMid2, the deletion of gene gp64 was carried out in the bacteria *E. coli* EL350/BacMid2 after electroporation of a recombination fragment of 3260 pb in which the totality of the gene of the cathepsin plus 779 bp of the sequence encoding 259 amino acids of chitinase and a part of the gene of gp64, deletion of 566 bp encoding 188 amino acids, was replaced by a bacterial expression cassette conferring zeocin resistance (Zeo®) (Drocourt et al., *Nucleic Acids Research*, vol. 18n° 13, 1990). The Zeo® gene derived from the commercially available plasmid pCR®-Blunt (Invitrogen) was placed under the control of the bacterial promoter T5N25, derived from the phage T5

(Gentz and Bujard, J. Bacteriology, vol. 164n° 1, 1985) and followed by the transcription terminator rrnBT1 (*E. coli* ribosomal RNA operon T1 terminator) (Kwon et al., *J Biol. Chem.*, vol 274 n° 41, 1999). The bacteria containing BacMid3 (*E. coli* EL350/BacMid3) were selected for their zeocin resistance. The baculovirus genome (i.e. BacMid3) is deficient for replication in insect cells, because three genes essential for viral replication (i.e. the gene encoding protein 1629 and the gene encoding DNAPol and the gene encoding gp64) are non-functional.

In the same way it will be possible to integrate the transgene in the locus PH. In this case, a pVT/gp37 not deleted (functional non-essential gene) or deleted totally or partially such as described in FIG. 4 will be used to repair the locus gp37/DNApol. It should be noted that the sequence of the gene gp37 which is present in pVT/gp37 described in FIG. 4, was modified, the ATG initiator (ATGi) was mutated and the gene gp37 was deleted from 240 amino acids, as explained hereafter:

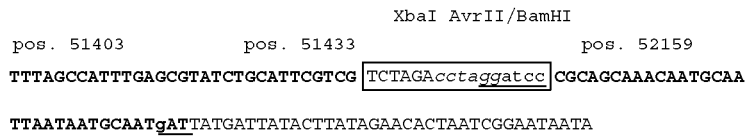

```
                   pos. 51403         pos. 51433                  pos. 52159
         TTTAGCCATTTGAGCGTATCTGCATTCGTCG TCTAGAcctaggatcc CGCAGCAAACAATGCAA TTAATAATGCAATgATTATGATTATACTTATAGAACACTAATCGGAATAATA
         ←
```

FIG. 3 is a diagram which illustrates the step of deletion of gp64 for the preparation of BacMid3.

Example 4: Use of BacMid2

A transfer vector pVT/gp37 was constructed to be able to generate recombinant baculoviruses expressing 2 transgenes. To do so, the fragment EcoRI F of the baculovirus genome AcMNPV containing the gene gp37 and the gene DNAPol was cloned in a bacterial plasmid pUC, thus generating pUC/gp37.

This plasmid was next modified in the following manner: a large part of the gene encoding gp37 was deleted (724 pb), the ATG initiator was mutated and replaced by two unique restriction sites XbaI and AvrII enabling the integration of a transgene under control of the natural promoter of gp37. These modifications thus led to the transfer vector pVT/gp37 being obtained.

The Sf9 cells were transfected by lipofection with the transfer vectors pVT/PH and pVT/gp37 loaded with the transgenes and DNA of BacMid2. The viruses generated after homologous recombination were cloned by the phage plaque assay method. The production of the recombinant protein was verified by a suitable method (e.g. for example ELISA, Western blot, enzymatic assay). The genome of the recombinant viruses was verified by Southern blot and the sequence of the transgene integrated in the viral genome was verified by sequencing after PCR amplification.

FIG. 4 is a diagram which illustrates the transfer vector pVT/gp37 for the expression of a gene X (where X is a gene different from the gene encoding the heavy chain of an antibody).

The genomes of recombinant baculoviruses generated after homologous recombination between BacMid2 and the transfer vectors no longer express gp37 (protein not essential for viral replication).

In order that the viral DNA is repaired in the 2 loci of BacMid2, a second recombination must take place with a transfer vector PH loaded or not with a transgene. In all cases, the DNA of the baculovirus genome will be repaired and thus infectious.

It will also be possible to use pVT/PH containing a wild sequence, that is to say containing the wild expression cassette (non-modified) leading to the production of polyhedrin. The pVT/PH could also be "empty" that is to say not contain transgene or polyhedrin gene.

Direction of Transcription of the Gene
Caption:
  Sequence of the gene in bold type
  ATG initiator underlined
  Polylinker XbaI/AvrII/BamHI in boxed section
  The nucleic sequence illustrated above is the sequence SEQ ID NO: 16

FIG. 5 is a diagram which illustrates the construction and the use of the transfer vector PH pVT/PH for the expression of a transgene X (where X is a transgene different from the gene encoding a light chain of an antibody).
Expression of the Heavy Chain of an Antibody.
  Construction of a specific pVT/gp37, pVT/gp37-Cγ1 This transfer vector contains the following expression cassette:
  Wild viral promoter P10 (SEQ ID NO: 1)
  DNA sequence encoding a signal sequence of a human immunoglobulin (secretion sequence)
  2 unique restriction sites for the cloning in phase of the variable region (VH) of the antibodies (region which gives the specificity of the antibodies)
  DNA sequence which encodes a constant region of epsilon, mu, or alpha human IgG (γ1-4).

FIG. 6 is a diagram which illustrates the construction and the use of the transfer vector pVT/gp37Cγ1 for the expression of the heavy chain of an antibody.
Expression of the Light Chain of an Antibody.
  Construction of a specific pVT/PH, pVT/PH-CL.
  This transfer vector contains the following expression cassette:
  Viral promoter P10 P10S1B (SEQ ID NO: 3)
  DNA sequence encoding a signal sequence of a human immunoglobulin (secretion sequence)
  2 unique restriction sites for the cloning in phase of the variable region (VL) of the antibodies (region which gives the specificity of the antibodies)
  DNA sequence which encodes a constant region of light chain (CL) kappa (κ) or lambda (λ) of human IgG.

FIG. 7 is a diagram which illustrates the construction and the use of the transfer vector pVT/PHC* for the expression of the light chain of an antibody.

Example 5: Use of BacMid3

A transfer vector, pVT/Chit-Cath, was constructed to be able to generate genomes of recombinant baculoviruses expressing 3 transgenes.

The fragment BstXI-XbaI derived from the regions EcoRI E and H of the baculovirus AcMNPV was cloned in a plasmid pUC. A deletion EcoNI-EcoRI of 1175 pb makes it possible to inactivate the genes encoding chitinase, non-essential, and cathepsin, also non-essential. The addition of a site XbaI between the sites EcoNI and EcoRI makes it possible to integrate a transgene. These modifications thus led to the transfer vector pVT/Chit-Cath being obtained. The Sf9 cells are transfected by lipofection with the transfer vectors pVT/PH, pVT/gp37 and pVT/chitCath loaded with the transgenes and the DNA of BacMid3. The viruses generated during homologous recombination were cloned by the phage plaque assay method. The production of the recombinant protein was controlled by a suitable method, ELISA, Western blot, enzymatic assay, etc., the genome of the recombinant viruses was controlled by Southern blot and the sequence of the transgene was controlled after PCR amplification.

FIG. 8 is a diagram which illustrates the construction of the vector pVT/Chit-Cath and its homologous recombination with BacMid3.

Example 6: Production of a Monoclonal Antibody Anti-CD4 (13B81) Using BacMid2

The DNAc encoding the regions VH and VL of the antibodies were integrated respectively in the transfer vectors pVT/PH-C$^-$ and pVT/gp37-Cγ1. Recombinant baculoviruses were generated after homologous recombination between 2 pVT and the DNA of BacMid2 of example 4:

The DNAc encoding the region VL of the antibodies was introduced into pVTPH/Ck which recombines with the region PH/1629 of BacMid2, The DNAc encoding the region VH of the antibodies was cloned in pVT/gp37-Cγ1 which recombines with the region gp37 of BacMid2.

The Sf9 cells were transfected by lipofection with BacMid2 and the 2 transfer vectors obtained in example 4 then incubated for 4 days at 28° C. The culture supernatants were collected and the recombinant baculoviruses generated and secreted in the culture medium were cloned by the phage plaque assay technique.

The organisation of the genome of the recombinant baculoviruses was controlled by Southern blot (see FIG. 9A) and the integrated transgenes (i.e. VL and VH) were verified after PCR amplification, cloning then sequencing. The recombinant antibodies secreted in the culture medium were purified on a Protein A Sepharose column (GE Healthcare) then analysed after migration in polyacrylamide gel and silver staining (FIG. 9B).

Example 7: Use of BacMid3 for the Production of VLP (Virus-Like-Particle)

Production of Flu VLP

To produce these VLPs, the 3 genes of the flu virus, M, HA and NA, were co-expressed. These 3 genes were integrated in the three transfer vectors necessary to recombine with the BacMid3 of example 5:

The gene M was introduced into the transfer vector pVT/PH as described in FIG. 5.

The gene HA was introduced into the transfer vector pVT/gp37 as described in FIG. 4.

The gene NA was introduced into the transfer vector pVT/Chit/Cath as described in FIG. 8.

The Sf9 cells were transfected by lipofection with BacMid3 and the 3 transfer vectors obtained above, then incubated for 4 days at 28° C. The recombinant baculoviruses generated then secreted in the culture supernatant were cloned by the phage plaque assay method.

The organisation of the genomes of recombinant baculoviruses was controlled by Southern blot (see FIG. 10) and the integrated genes were verified after PCR amplification, cloning then sequencing. Southern blot was carried out on the genomic DNA of the recombinant virus expressing the 3 proteins HA, NA and M of the flu virus. This experiment, carried out with specific probes for these 3 genes, made it possible to detect the presence of DNAc encoding the 3 proteins in the recombinant baculovirus genome.

Example 8: Use of BacMid3 for the Production of Bispecific Antibodies

The bispecific antibody constructed according to the international application WO 2013/005194 is constituted of a heavy chain composed of the domains VH+CH1+CH2+ CH3 of an antibody 1, N-terminal fused to the domains VH+CH1 of an antibody 2. Mutations introduced at the interface of the regions CL and CH1 of the antibodies 1 favour the correct pairings between the domains VL1 and VL2 of the light chains L1 and L2 which are produced separately and the corresponding domains VH1 and VH2. The production of this antibody necessitates the simultaneous production and in equal quantity of 3 chains, the fused heavy chain, the light chain L1 and the light chain L2.

The DNAc encoding the light chain L1 was introduced into the transfer vector pVT/PH as described in FIG. 5.

The DNAc encoding the light chain L2 was introduced into the transfer vector pVT/gp37 as described in FIG. 4.

The DNAc encoding the fused heavy chain was introduced into the transfer vector pVT/Chit-Cath as described in FIG. 8.

FIG. 11 is a diagram which illustrates in A the structure of the bispecific antibodies and in B the analysis by electrophoresis in polyacrylamide gel of the bispecific antibodies purified on Protein A Sepharose column (GE Healthcare).

Example 9: Construction of BacMid2-Fur Enabling the Generation of Recombinant Baculoviruses Correctly Expressing Matured Mannosylated Proteins The general principle that was used to introduce into the bacmids the genes enabling to optimise post translational modifications of the proteins (BacMid2/MPT (MPT: Post-Translational Modification) is described in FIG. 14 and detailed in example 10. When several genes are necessary, they are integrated in an iterative manner in regions or genes not essential for replication of the virus. Table 2 below describes the integration sites and the nature of the genes integrated in the different bacmids which were constructed.

TABLE 2

| Integration site in the viral genome | Promoter used to control the expression | | Name of the gene involved in post translational modification | | |
|---|---|---|---|---|---|
| | Origin of the promoter | RNA polymerase used | Gene | Origin of the gene | Reference |
| Intergenic v-ubi (orf35)/39k (orf36) pos. 29226 | P9 promoter of JcNDV | Cellular | GNT-II | Human | Tan et al. 1995 |
| egt (orf15) pos. 12786 Integration in the gene egt | Promoter of the gene gp64 of OpMNPV | Cellular and viral | β1,4GalTI | Bovine | d'Agostaro et al. 1989 |
| iap2 (orf71) pos. 61222 Integration in the gene iap2 and deletion of 335nt (112 aa) of iap2 | Promoter of the gene ie1 of CfMNPV | Cellular | CMP NeuAc synthase | Human | Munster et al. 1998 |
| | Promoter of the gene ie1 of LdMNPV | Cellular | NeuAc synthase | Human | Lawrence et al. 2000 |
| Intergenic orf51/orf52 pos. 44298 | Promoter of the gene ie1 of WSSV | Cellular | ST3GalIV | Human | Kitagawa and Paulson, 1994 |
| | Promoter of the gene ie1 of WSSV | Cellular | ST6GalI | Human | Grundmann et al. 1990 |
| | Promoter of the gene actin 3 of *B. mori* and promoter of the gene ie1 of WSSV | Cellular | ST3GalIV + ST6GalI | Human | |
| pif1 (Orf119) pos. 100697 Integration in the place of the gene pif1 which is entirely deleted | Promoter of the gene ie1 of WSSV | Cellular | ST6GalI | Human | |
| chit/cath (orf126/orf127) pos. 106160 Deletion of 787nt of chit(263 aa N-terminal) and 342nt of cath (114 aa N-terminal) | Synthetic promoter P10S1 | Viral | Sf9-fur | Lepidoptera Cell Sf9 | Cieplik et al. 1998 |

Numbering of the bases conforming to the sequence of the virus AcMNPV filed in GenBank under the reference "NC_001623, *Autographa californica* nucleopolyhedrosis genome, complete sequence"

reference "NC_001623, *Autographa californica* nucleopolyhedrosis genome, complete sequence"

Caption of table 2: the genes involved in the elaboration of the post-translational modifications (example: glycosylation, endoproteolytic cleavage) were inserted into non-essential genes/regions of the bacmids. Except in the case of the over-expression of cellular furin which is produced under the control of a strong late promoter P10S1, the promoters used to control the expression of these genes are early so as to produce these enzymes before the biosynthesis of the proteins of interest that will be expressed under the control of late promoters.

BacMid2-Fur was constructed from the BacMid2 obtained in example 2. The gene encoding furin of the lepidoptera cell Sf9 (fur) was cloned downstream of a synthetic late promoter P10S1 of sequence:

```
                                         (SEQ ID NO: 17)
5'-ATAAGTATTTTAATCTTTTCGTTTGTATATTAATTAAAATACTATAC

TGTATAAAAAAACCTATAAATATCCCGGATTATTCATACCGTCCCACCAT

CGGGCGTACGCCACC-3'.
```

The gene fur was integrated in the chitinase-cathepsin locus. The transfer vector, pVT/Chit-Cath of which the construction is described in example 5 was used. The expression cassette comprising the gene fur under control of the synthetic promoter P10S1 was introduced at the unique site XbaI of the pVT/Chit-Cath (position 106160 in the genome of the baculovirus), to give the plasmid pVT/Chit-Cath-Fur. The gene fur was cloned in the same direction as the inactivated cathepsin gene.

A bacterial expression cassette "zeocin resistance (Zeo®)" composed as follows: [Bacterial promoter T5N25-Zeo®-terminator rrnBT1] containing a site Bsu36I on either side was cloned at the site EcoRI of pVT/Chit-Cath-Fur, to give the plasmid pVT/Chit-Cath-Fur-Zeo®. This second cassette enables the expression of the gene Zeo® and thus confers on the bacterium bearing this plasmid zeocin resistance.

The recombination fragment of 5927 pb was prepared after digestion of the plasmid pVT/Chit-Cath-Fur-Zeo® by BglII thus generating flanking regions for the homologous recombination of 652 pb and 704 pb on either side of the fragment. After electroporation in the bacterium EL350/BacMid2, the bacteria were selected on zeocin. As described in FIG. 14, the bacterial expression cassette Zeo® was eliminated by digestion Bsu36I, repair then ligation.

BacMid2/Fur was thus obtained. The genomes of these new BacMids were controlled by Southern (FIG. 15) then by sequencing of the integrated gene fur.

Example 10: Construction of BacMid2-Gal Enabling the Generation of Recombinant Baculoviruses Expressing Galactosylated Proteins BacMid2-Gal was constructed from the BacMid2 obtained in example 2. The DNAc encoding 2 glycosyltransferases missing in lepidoptera cells and necessary for the biosynthesis of galactosylated glycans, human NI-acetylglucosaminyltransferase II (GNT-II) (EC 2.4.1.143, Accession n° NM_002408.3) and bovine β1,4 galactosyltransferase (β1,4GalT) (EC 2.4.1.38, Accession n° NM_177512.2) were introduced into non-essential genes or regions of BacMid2 by homologous recombination. In order that the enzymatic activities of β1,4GalT and GNT-II are expressed before the synthesis of the transgene(s) of interest encoding a polypeptide of interest, the transgenes encoding GNT-II and β1,4GalT were cloned downstream of early viral promoters such as described in table 2.

FIG. 14 illustrates in a general manner the different steps necessary for the construction of a BacMid comprising one or more transgene(s) each encoding a protein maturation enzyme BacMid2/MPT. In particular, in FIG. 14, the transgene encoding the protein maturation enzyme is the gene encoding GNTII (gene GNTII).

The addition of transgenes encoding respectively GNT-II and β1,4GalT was carried out in an iterative manner in BacMid2.

Insertion of the transgene GNT-II

This transgene was introduced in position 29226 of the viral genome by homologous recombination between orf35 (v-ubi) and orf36 (39k) designated intergenic region IG35/36. In order to be able to insert the expression cassette in the genome of BacMid, the unique sites for cloning XbaI (italics) and Bsu36I (underlined) were integrated by PCR in the region IG35/36 with the following primers:

```
antisense ig35/36
                                    (SEQ ID NO: 7)
5'-CCTGGTAATTTTTGACCACGG-3' (position 28806 in the viral genome)
and Sense mut ig35/36
                                    (SEQ ID NO: 6)
5'-GCCTTAGGTCTAGAGTATATTTAATGGTTTTTATTATTGTTATTATT AATACCCTCC-3' then Antisense mut ig35/36
                                    (SEQ ID NO: 5)
5'-CTCTAGACCTAAGGCATAAAAGTTTTTTATTTAATCTGACATATTTG TATCTTGTGTATTATCGC-3'
and Sense ig35/36
                                    (SEQ ID NO: 4)
5'-CGCAGCAATTCCAGCGAGC-3' (position 29657 in the viral genome)
```

The PCR fragment obtained of 861 bp was cloned in a plasmid pGEM® Teasy and controlled by sequencing, to give the plasmid pGEM-IG35/36.

Two expression cassettes were introduced into the above plasmid pGEM-IG35/36.

A viral expression cassette, composed as follows [Promoter P9 of the densovirus—JcNDV—transgene encoding GNTII—stop TkpA] was inserted at the level of the site XbaI, to give the plasmid pGEM-IG35/36-GNTII. The Promoter P9 of the densovirus JcNDV is described in Shirk P D, Bossin H, Furlong R B, Gillett J L. Regulation of *Junonia coenia* densovirus P9 promoter expression. Insect Mol Biol. 2007 October; 16(5):623-33. Epub 2007 Aug. 22.

The bacterial expression cassette "zeocin resistance" (Zeo®) (obtained from the commercially available plasmid pCR® Blunt, InVitrogen) composed as follows: [Bacteria/promoter T5N25-Zeo®—terminator rrnBT1] was cloned at the level of the site Bsu36I. This second cassette enables the expression of the Zeo® gene and thus will confer on the bacterium bearing it zeocin resistance, to give the plasmid pGEM-IG35/36-GNTII-Zeo®. The bacterial promoter T5N25 is described in Gentz R, Bujard H. Promoters recognized by *Escherichia coli* RNA polymerase selected by function: highly efficient promoters from bacteriophage T5. J Bacteriol. 1985 October; 164(1):70-7. The transcription terminator rrnBT1 is described in Kwon Y S, Kang C. Bipartite modular structure of intrinsic, RNA hairpin-independent termination signal for phage RNA polymerases. J Biol Chem. 1999 Oct. 8; 274(41):29149-55.

The recombination fragment of 3493 bp<IG35/36-GN77I-Zeo®> obtained after digestion by EcoRI of the plasmid generated above pGEM-IG35/36-GNTII-Ze® and having flanking regions for the homologous recombination of 420 bp and 428 pb on either side of the recombination fragment, was electrophoresed in the bacteria EL350/BacMid2. The bacteria containing BacMid2/GNTII-Zeo® (*E. coli*/EL350/BacMid2/GNTII-Zeo®) were selected for their kanamycin, hygromycin and zeocin resistance. The DNA of 3 clones of Bacmid2/GNTII-Zeo® selected was extracted then the GNT-II and Zeo® genes inserted into the region IG35/36 were controlled by PCR then sequencing.

The bacterial expression cassette flanked on either side of a site Bsu36I was next eliminated by simple digestion by Bsu36I, repair of the ends of the DNA with the DNA polymerase of Klenow then ligation of the plasmid on itself. It should be noted that the "repaired" sequence Bsu36I [5' CCTNATNAGG 3'] was conserved in Bacmid2/GNTII thus generated after ligation of the plasmid. This sequence is thus present in the recombinant baculovirus and it may constitute a specific signature.

The transgene encoding GNTII was cloned in the same direction as the gene 39K.

BacMid2/GNTII was thus obtained then controlled as described above before being used for the insertion of the gene encoding β1,4GalT.

Insertion of the gene β1,4GalT

The transgene encoding β1,4GalT was integrated in the locus of the non-essential gene egt (Ecdysteroid glycosyltransferase, ORF15, position in the genome position 11426-12946 of the viral genome AcMNPV) of BacMid2/GNTII according to the general principle described above. The fragment PstI-BamHI of 5110 bp (position 9999 to 15110 in the viral genome of AcMNPV) containing the gene egt, was cloned beforehand in a plasmid pUC to give the plasmid pUC-EGT. Then, the viral expression cassette comprising the DNAc encoding bovine β1,4GalT under control of the promoter gp67 of OpMNPV was introduced into the gene egt by insertion (inactivation of the gene by insertion) at the unique site XbaI (position 12782 in the genome of the baculovirus) present in the sequence encoding the gene egt, to give the plasmid pUC-EGT-GalT. The transgene encoding β1,4GT was cloned in the same direction as the gene egt.

An adaptor NsiI-Bsu36I-NsiI was next inserted in the site NsiI situated downstream of the gene β1,4GalT, which enabled the introduction of the bacterial expression cassette Zéo® in Bsu36I generating the plasmid pUC-EGT-GalT-Zeo®.

The recombination fragment of 3128 bp was prepared after digestion of the above plasmid pUC-EGT-GalT-Zeo® by SnaBI-NruI thus generating flanking regions for the homologous recombination of 474 bp and 866 pb on either side of the fragment. After electroporation in the bacterium EL350/BacMid2-GNTII, the bacteria were selected on zeocin. As previously, the bacterial expression cassette Zéo® was eliminated by digestion Bsu36I, repair then ligation.

BacMid2/GNTII/β1,4GalT (also called BacMid2-Gal or BacGal) was thus obtained. The genome of BacMid2-Gal was controlled by Southern then sequencing of all the integrated genes.

Example 11: Construction of BacMid2Gal-Fur Enabling the Generation of Recombinant Baculoviruses Correctly Expressing Matured Galactosylated Proteins BacMid2-Gal-Fur was constructed as described for BacMid2-Fur (Example 9).

The bacteria EL350/BacMid2-Gal were electrophoresed with the recombination fragment of 5927 pb described in example 9, then selected on zeocin. As previously, the bacterial expression cassette Zéo® was eliminated by digestion Bsu36I, repair then ligation. BacMid2Gal-Fur was thus obtained. The genome of the bacmid was controlled by Southern (FIG. 15) then sequencing of the new integrated gene.

Examples 12: Construction of BacMid-Sia3 (or BacSia3)

The transgenes encoding human CMPNeuAc synthase (CMPNeuAc synthase or CMPNeuAcS) (EC 2.7.7.43, accession n° NM_018686.5), human NeuAc synthase (NeuAc Synthase or NeuAcS) (EC 2.5.1.56, accession n° AF257466) and human α2,3 sialyltransferase (ST3), ST3GalIV (EC 2.4.99.4, accession n° X74570) were inserted into BacMid2/GNTII-β1,4GT in an iterative manner according to the general principle described in FIG. 14.

Cloning of the two transgenes encoding respectively NeuAc synthase and CMP NeuAc Synthase in locus iap2 of BacMid2-Gal.

The Applicant chose to clone these two enzymes head to tail under the control of very early promoters, the promoter IE1 (immediate-early 1) of the baculovirus of *Choristoneura fumiferana* for the control of the expression of the gene CMP NeuAc synthase and that of the baculovirus of *Lymantria dispar* for the control of the expression of the gene NeuAc synthase (see Table 2) The region comprising the gene iap2 (ORF71) of the baculovirus AcMNPV (position in the genome 61016-61765) was amplified beforehand by double PCR with the following primers:

```
Sense iap2
                                        (SEQ ID NO: 8)
5'- GATATTGTGTGCTCAATGTC-3' (Position 60736 in the viral genome)

Antisense BstBI
                                        (SEQ ID NO: 9)
5'- CCTAAGGTCTAGATTCGAATACGTGTGTCG -3' then Sense BstBI
                                       (SEQ ID NO: 10)
5'- CGAATCTAGACCTTAGGCCGCGGCTAAGCGTTAAACC -3'

Antisense iap2
                                       (SEQ ID NO: 11)
5'- CGATCACCGTCGCTGTCGTCTTC -3' (Position 61951 in the viral genome)
```

These successive PCRs also made it possible (i) to integrate the unique sites Bsu36I (underlined above) and XbaI (double underlined above) and (ii) to delete a large part of the sequence encoding iap2, deletion of 335 bp/112 amino acids. The amplified fragment of 896 bp was cloned in a plasmid pGEM® Teasy, to give the plasmid pGEM-IAP2.

A viral expression cassette, composed as follows [Stop SV40-CMPNeuAc Synthase-Promoter IE1Cf-Promoter IE1Ld-NeuAcSynthase] was inserted at the site XbaI of pGEM-IAP2, to give the plasmid pGEM-iap2-CMP-NeuAcS-NeuAcS.

The bacterial expression cassette "zeocin resistance" (Zeo®) composed as follows: [Bacterial promoter T5N25-Zeo®-terminator rrnBT1] was cloned at site Bsu36I of pGEM-iap2-CMPNeuAcS-NeuAcS, to give the plasmid pGEM-iap2-CMPNeuAcS-NeuAcS-Zeo®. This second cassette enables the expression of the Zeo® gene and thus confers on the bacterium bearing this plasmid zeocin resistance.

The recombination fragment [CMPNeuAc-NeuAcS-Zeo®] of 4548 pb was prepared after digestion of the plasmid pGEM-iap2-CMPNeuAcS-NeuAcS-Zeo® by the restriction endonuclease NotI which generates flanking regions for the homologous recombination of 486 bp and 396 pb on either side of the fragment. The bacteria EL350/BacMid2-GNTII-β1,4GT were electrophoresed with the recombination fragment thus generating BacMid2-GNTII-β1,4GT-CMPNeuAcS-NeuAcS-Zéo®. As previously, the zeocin resistance cassette was eliminated after digestion by Bsu36I, repair then relegation. BacMid2-GNTII-β1,4GT-CMPNeuAcS-NeuAcS was thus obtained.

Cloning of the transgene a2,3-sialyltransferase IV (ST3GalIV) in the intergenic region comprised between orf51 and orf52 (IG51/52) of BacMid2-GN-TII-β1,4GT-CMPNeuAcS-NeuAcS.

This region located in the fragment EcoRI N of the baculovirus AcMNPV was isolated after amplification by double PCR with the following primers:

```
Sense IG51/52
                                       (SEQ ID NO: 12)
5'- GGAAAACTTTCCGAAGACGAAC (position 43814 in the viral genome)
and Antisense Xba/IG51/52
                                       (SEQ ID NO: 13)
5'- CCTAAGGTCTAGAGTGCCTTTTGTTTGCTATTTTGCGCCG-3' then

Sense Xba/IG51/52
                                       (SEQ ID NO: 14)
5'- CTCTAGACCTTAGGTCCGCGCTCTCCCACGC-3'
and Antisense IG51/52
                                       (SEQ ID NO: 15)
5'- GGTGCAGAACATAATGACGTGGCCTTAC (position 44723 in the viral genome)
```

During these successive PCRs there is addition of 2 unique sites Bsu36I (underlined above) and XbaI (double underlined above) in the intergenic region ORF51/ORF52 which will enable integration of the expression cassette ST3 at site XbaI in position 44298 in the viral genome. The fragment obtained of 922 bp was cloned in a pGEM® T easy (Promega), to give the plasmid pGEM-IG51/52.

As for the other enzymes, ST3GalIV must be present in the cells before the glycoproteins of interest are expressed. We chose the promoter IE1 of the shrimp virus WSSV (White Spot Syndrome Virus) identified as being a functional cell promoter 519 of "immediate-early" type (See Table 2)(Liu et al., Virology, 2005; Liu et al. J of virology, 2007; Gao et al., J. Biotechnology, 2007).

A viral expression cassette, composed as follows [promoter WSSV-ST3] was inserted at site XbaI of pGEM-IG51/

52, to give the plasmid pGEM-IG51/52-ST3. ST3GalIV was cloned in the opposite direction of orf51.

The bacterial expression cassette "zeocin resistance (Zeo®)" composed as follows: [Bacterial promoter T5N25-Zeo®-terminator rrnBT1] was cloned at site Bsu36I of pGEM-ORF51-ST3, to give the plasmid pGEM-IG51/52-ST3-Zeo®. This second cassette enables the expression of the Zeo® gene and thus confers on the bacterium bearing this plasmid zeocin resistance.

A recombination fragment [ST3Ga/IV-Zeo®] of 2589 pb was generated from pGEM-IG51/52-ST3-Zeo® by digestion by the restriction endonuclease NotI. This digestion generated flanking regions for the homologous recombination of 498 bp and 411 pb on either side of the expression cassette. Homologous recombination was carried out in the bacterium EL350/BacMid2-GNTII-β1,4GT-CMPNeuAcS-NeuAcS, generating BacMid2-GNTII-β1,4GT-CMP-NeuAcS-NeuAcS-ST3. (or BacSia3). The genome of BacSia3 was controlled by Southern then sequencing of all the integrated genes.

Example 13: Construction of BacMid-Sia6 (or BacSia6)

Cloning of the transgene a2,6-sialyltransferase I (ST6GalI) in the intergenic region orf51/orf52 (IG51/52) of BacMid2-GNTII-β1,4GT-CMPNeuAcS-NeuAcS.

The method for cloning the gene encoding human α2,6 sialyltransferase, ST6GalI (EC 2.4.99.1, accession n° X17247) is similar to that described in example 12 for the transgene encoding ST3GalIV, summarised as follows:

a viral expression cassette, composed as follows [promoter WSSV-ST6] was inserted at site XbaI of pGEM-IG51/52, to give the plasmid pGEM-IG51/52-ST6. ST6GalI is cloned in the opposite direction to orf51 the bacterial expression cassette "zeocin resistance" (Zeo®) composed as follows: [Bacterial promoter T5N25-Zeo®-terminator rrnBT1] was cloned at site Bsu36I of pGEM-ORF51-ST6 generating the plasmid pGEM-IG51/52-ST6-Zeo®. This second cassette enables the expression of the Zeo® gene and thus confers on the bacterium bearing this plasmid zeocin resistance.

A recombination fragment [ST6Ga/I-Zeo®] of 2825 pb was generated from pGEM-IG51/52-ST6-Zeo® by digestion by restriction endonuclease NotI. This digestion generated flanking regions for the homologous recombination of 498 bp and 411 pb on either side of the expression cassette. The homologous recombination was carried out in the bacterium EL350/BacMid2-GNTII-β1,4GT-CMPNeuAcS-NeuAcS, generating BacMid2-GNTII-β1,4GT-CMPNeuAcS-NeuAcS-ST6 (or BacSia6). The genome of BacSia6 was controlled by Southern then sequencing of all the integrated genes.

Example 14: Construction of BacMid-Sia6II (or BacSia6-II)

a. Cloning of the transgene a2,6-sialyltransferase I (ST6GalI) in ORF119 (PIF1) of BacMid2-GNTII-β1,4GT-CMPNeuAcS-NeuAcS.

ORF119 (position in the genome 100699-102291), encoding PIF1, protein not essential for viral replication, is located in the fragment EcoRI E of the baculovirus AcMNPV. A fragment on either side of the gene was obtained after amplification by double PCR with the following primers:

```
Sense pif1
                                     (SEQ ID NO: 18)
5'-GAATACAACGCCACATCTATTCCTAGTACAAC-3' (position 100247 in the viral genome)
and pif1bac5'
                                     (SEQ ID NO: 19)
5'-CTAGAGGCGTTAACCTAAGGTACTTATTGGAGAATGTCCGAGTATTT TTG-3' then pif1for3'
                                     (SEQ ID NO: 20)
5'- CCTTAGGTTAACGCCTCTAGAACATGAGCATTTTAAAAGTTGTAGA AGCG-3'
and RevPif1
                                     (SEQ ID NO: 21)
5'- CATTAACAATTACTACGGCGCATTTTGACCATC-3' (position 102825 in the viral genome)
```

These successive PCRs made it possible to eliminate the totality of ORF119, to integrate the unique sites Bsu36I (underlined above) and XbaI (double underlined above). The site XbaI will enable the integration of the expression cassette ST6 in position 100697 in the viral genome. The fragment obtained of 998 bp was cloned in a pGEM® Teasy (Promega), to give the plasmid pGEM-PIF1.

The viral expression cassette, described in example 12 [promoter WSSV-ST6] was inserted at site XbaI of pGEM-PIF1, to give the plasmid pGEM-PIF1-ST6. ST6GalI was cloned in the direction of pif1.

The bacterial expression cassette "zeocin resistance (Zeo®)" composed as follows: [Bacterial promoter T5N25-Zeo®-terminator rrnBT1] was cloned at site Bsu36I of pGEM-PIF1-ST6, to give the plasmid pGEM-PIF1-ST6-Zeo®. This second cassette enables the expression of the Zeo® gene and thus confers on the bacterium bearing this plasmid zeocin resistance.

A recombination fragment [ST6Ga/I-Zeo®] of 2903 pb was generated from pGEM-PIF1-ST6-Zeo® by digestion by the restriction endonuclease NotI. This digestion generated flanking regions for the homologous recombination of 498 bp and 411 pb on either side of the expression cassette. The homologous recombination was carried out in the bacterium EL350/BacMid2-GNTII-β1,4GT-CMPNeuAcS-NeuAcS, generating BacMid2-GNTII-β1,4GT-CMPNeuAcS-NeuAcS-ST6-II (or BacSia6-II). The genome of BacSia6-II was controlled by Southern (FIG. 19B) then sequencing of all the integrated genes.

Example 15: Construction of BacMid-Sia3/6 or BacSia3/6

Head to tail cloning of the transgenes ST6GalI and ST3GalIV in the intergenic region orf51/orf52 (IG51/52) in BacMid2-GNTII-β1,4GT-CMPNeuAcS-NeuAcS.

The cloning method is similar to that described in Examples 12 and 13 for the transgene encoding ST3GalIV and the transgene encoding ST6GalI, summarised as follows:

a viral expression cassette comprising a transgene encoding ST6GalI and a transgene encoding ST3GalIV, composed as follows [ST6-promoter WSSV-actin promoter 3 B, mori-ST3-Stop actin 3] was inserted at site XbaI of pGEM-IG51/52, to give the plasmid pGEM-IG51/52-ST3/ST6.

the bacterial expression cassette "zeocin resistance" (Zeo®) composed as follows: [Bacterial promoter T5N25-Zeo®-terminator rrnBT1] was cloned at site Bsu36I of pGEM-IG51/52-ST3/ST6, to give the plasmid pGEM-IG51/52-ST3/ST6-Zeo®. This second cassette enables the expression of the Zeo® gene and thus confers on the bacterium bearing this plasmid zeocin resistance.

A recombination fragment [ST3/ST6-Zeo®] of 5008 pb was generated from pGEM-IG51/52-ST3/ST6-Zeo® by digestion by the restriction endonuclease NotI. This digestion generated flanking regions for the homologous recombination of 490 bp and 426 pb on either side of the expression cassette. The homologous recombination was carried out in the bacterium EL350/BacMid2-GNTII-β1, 4GT-CMPNeuAcS-NeuAcS, to give BacMid2-GNTII-β1, 4GT-CMPNeuAcS-NeuAcS-ST3/ST6 (or BacSia3/6). The genome of BacSia3/6 was controlled by Southern then sequencing of all the integrated genes.

Example 16: Use of BacMid2-Fur for the Production of Mature HIV1 Glycoprotein Gp160

HIV1 gp160 must undergo a step of maturation in order that the virus is infectious and that the surface glycoproteins of the virus are organised into trimers. These structures are today considered as essential for the formation of epitopes of interest necessary for the elaboration of a vaccine against HIV-1. This maturation is carried out by cellular furin which is going to cleave gp160 into gp120+gp41. The production of gp160 in a recombinant form in general leads to a partially matured form and does so whatever the expression system.

In order to obtain a completely matured gp160 we integrated the gene encoding furin of the Sf9 cell in the viral genome under the control of a very active promoter, a promoter P10-like called P10S1 and constructed BacMid2-Fur (Example 9).

From this bacmid, we constructed a double-recombinant virus expressing 2 proteins of HIV1, polyprotein Pr55Gag and gp160. The production of these 2 proteins leads to the secretion in the culture medium of virus-like-particles (VLP). In this experiment we concentrated (noted C and NC for non-concentrated) the VLP secreted with a solution of "Retro Concentin™ Virus Precipitation" (SBI, reference RV100A-1). The different samples obtained after infection with a wild virus BACWT or multi-recombinant viruses expressing gp160 and Pr55Gag (BAC/gp160/Gag), gp160 and Pr55Gag and furin (BAC/gp160/Gag) or mono-recombinant viruses like the virus BAC gp120 which expresses uniquely soluble gp120 and the virus BACGag which expresses uniquely the polyprotein Pr55Gag (BACGag) were analysed by Western blot with an antibody anti-gp120, Panel A (goat polyclonal antibodies directed against gp120 of HIV1, reference Ab21179, Abcam) or an antibody anti-Gag, Panel B (Anti-p55+p24+p17, Reference Ab63917, Abcam).

As is shown in FIG. 15C, the activity of the cellular furin is not sufficient to mature the totality of the gp160 which is produced (Well BACgp160/Gag). Conversely, when there is over expression of this enzyme, there is a complete maturation of gp160 into gp120 (Well BACgp160/Gag/fur).

Example 17: Use of BacMid2-Gal for the Production of Galactosylated Antibodies

A terminal N-galactosylation being a characteristic of glycosylation of Asn297 situated in the constant domain of the IgG (FIGS. 12 and 13), the examples described below concern the production of recombinant antibodies.

BacMid2-Gal was used like BacMid2 described previously (Examples 4 and 6) for the generation in a single step of a double recombinant baculovirus (FIGS. 16 and 17). As for BacMid2, co-transfection with BacMid2-Gal led to a very high content, close to 100%, of recombinant viruses (FIG. 9A).

Insertion of Transgenes Encoding the Heavy and Light Chains of an Antibody.

1. Principle of the Generation of Recombinant Baculoviruses.

DNAc encoding the variable regions VH and VL of the antibodies of interest were inserted into specific baculovirus transfer vectors (pVT) of the heavy and light chains of the antibodies, pVT/gp37-H (for cloning the variable region of the heavy chain) (FIG. 6) and pVT/PH-L (for cloning the variable region of the light chain) (FIG. 7). These vectors have been described in the article (Juliant et a., 2013). The Sf9 cells were next transfected with the 2 loaded pVT and DNA of BacMid2-Gal. Double-recombinant viruses co-expressing the heavy and light chains of antibodies were then produced in a single step (FIG. 17).

2. Construction of a Recombinant Virus Expressing a Galactosylated Antibody.

Recombinant viruses expressing the same antibodies were produced from BacMid2 and BacMid2-Gal. The antibodies produced after infection of Sf9 cells with the recombinant virus derived from BacMid2 serves as control since they have an "insect" glycosylation, that is to say glycan motifs of paucimannosidic type and to a lesser proportion of oligomannosidic type (FIG. 12).

Cloning in the transfer vectors.

The fragments of DNAc encoding the variable regions of the heavy and light chains of the antibodies of interest were cloned in the respective transfer vectors (pVT/gp37-H and pVT/PH-L). In the course of this cloning, the complete genes encoding the 2 chains of antibodies are reconstituted (FIGS. 6 and 7).

Generation and cloning of the recombinant baculoviruses.

The Sf9 cells were transfected by lipofection with the loaded pVT/gp37-H and pVT/PH-L and DNA of Bacmid2-Gal or BacMid2 (FIG. 17). After 7 days of infection at 28° C., the baculoviruses secreted in the culture supernatant were cloned by the phage plaque assay technique.

Control of the genomic organisation of the recombinant viruses.

Several baculoviral clones were selected, amplified and their genome extracted to be analysed by Southern blot. The genes encoding the heavy and light chains inserted into the baculoviral genome were also amplified by PCR then sequenced.

Production and purification of the recombinant antibodies.

Sf9 cells suited to the growth in serum free medium were infected at a level of 3 PFU/cell. After 3 days of infection, the culture supernatant was collected and deposited on a Protein A Sepharose column (GE-Healthcare). The quality of the antibodies was verified after migration in polyacrylamide gel and silver staining.

Analysis of glycosylation by lectin blot.

Principle of lectin blot: lectins are molecules that attach themselves specifically on glycan motifs. It is thus very simple to demonstrate the presence of a particular glycan bound to a protein after electrophoresis in polyacrylamide gel, transfer onto a nitrocellulose membrane and incubation of the membrane with a biotin conjugated lectin (example biotinylated lectin $RCA_{120}$, reference B1085, Vector Laboratories) or with digoxigenin (example the lectins of the "DIG Glycan Differentiation Kit", reference 11210238001, Roche). The presence of lectins is then detected indirectly thanks to an antibody directed against biotin or the digoxigenin itself peroxidase conjugated or with alkaline phosphatase. The presence of these enzymes is then detected thanks to their enzymatic activity which will generate either a brown red precipitate for peroxidase or a blue coloration for alkaline phosphatase.

Experimentation

The production of antibodies was controlled by Western blot. The proteins were separated by electrophoresis on a polyacrylamide gel at 10% in the presence of SDS and 2-mercaptoethanol then transferred onto a nitrocellulose membrane (Protran™ 0.45 µm NC, GE Healthcare). The transfer of the proteins was verified after ponceau red staining. The membrane was incubated with (FIG. 18A) a sheep polyclonal antibody directed against human IgG and peroxidase conjugated (Reference NA933V, GE Healthcare) or (FIG. 18B) with a sheep polyclonal antibody directed against mouse IgG and peroxidase conjugated (Reference NA931V, GE Healthcare). The peroxidase was revealed by chemiluminescence with the SuperSignal® West Pico Chemiluminescent Substrate System (reference: 34077, Thermo Scientific).

Analysis by lectin blot (FIG. 18C). In this example, we used biotinylated lectin $RCA_{120}$ (Ricinus communis agglutinin) which attaches itself specifically onto beta-galactosyl residues. The proteins were separated by electrophoresis on a polyacrylamide gel as described above for Western blot, transferred onto Protran™ 0.45 m NC membrane (GE Healthcare) then incubated in the presence of biotinylated $RCA_{120}$. The lectin was revealed indirectly after incubation of the membrane with an anti-biotin antibody peroxidase conjugated (Goat antibodies, reference A4541, Sigma). Revelation was carried out in the presence of a chemiluminescent substrate (SuperSignal® West Pico Chemiluminescent Substrate, Thermo Scientific)

3. Results

Human (FIG. 18A) and mouse (FIG. 18B) recombinant antibodies were produced, purified on Protein A Sepharose (GE Healthcare) then analysed by Western blot (FIGS. 18A and B) and by lectin blot (FIG. 18C). FIGS. 18A and B indeed confirm the presence of human and mouse recombinant antibodies, Wells 2 and 3: Wells 4 and 5. FIG. 18C, shows that only the antibodies—human or mouse—produced by cells infected with the recombinant baculoviruses generated from BacMid2-Gal are recognised by $RCA_{120}$ (Wells 3 and 5). The antibodies produced during infection by the recombinant viruses derived from BacMid2 are not recognised by the lectin, Wells 2 and 4.

These experiments clearly demonstrate that the BacGal virus is capable of complementing Sf9 cells to be able to produce galactosylated glycoproteins.

Example 18: Use of BacMid-Sia3

1. Construction of a Recombinant Baculovirus Expressing its Alpha 2,3 Sialylated Glycoprotein Envelope Gp64.

The activity of BacSia3 was controlled using as model protein the surface glycoprotein of the virus, gp64. Glycoprotein gp64 is the major glycoprotein of the baculovirus, it is involved in all the first steps of infection. It is located on the surface of the virus. It has been shown that this glycoprotein is capable of being galactosylated and sialylated (Jarvis et al. 1995). To do so, a recombinant virus was obtained by homologous recombination between BacMid-Sia3 and the empty transfer vectors pVTPH and pVT/gp37. The presence of α2,3 sialyl motifs was demonstrated thanks to a lectin blot carried out with lectin di-CBM40 described in the article (Ribeiro et al., 2016).

Generation and cloning of the recombinant baculoviruses.

The Sf9 cells were transfected by lipofection with empty pVTPH and pVT/gp37 and DNA of Bacmid2 (control) or BacMid-Sia3 obtained in example 12 and according to the principle of FIG. 19A. After 7 days of infection at 28° C., the viruses secreted in the culture supernatant were cloned by the phage plaque assay technique. Four viral clones were selected, amplified and their genome extracted to be analysed by Southern blot. The gene inserted in the viral genome was amplified by PCR then sequenced.

Analysis of glycosylation by lectin blot.

The lectin used in this example was biotinylated di-CBM40. The protocol that was used is similar to that which is described in example 17. After saturation, the membrane was incubated with diCBM40-Biotinylated lectin diluted 1/200 (5.7 µg/ml) in TBS-T or with SNA-Dig lectin (Roche, Kit DIG Glycan Differentiation Kit) diluted 1/1000 in TBS-T. The revelation of the membranes was carried out as described in example 17. The presence of gp64 was controlled by Western blot in the presence of an anti-gp64 antibody (monoclonal mice antibodies AcV5 reference SC65499, Santa Cruz Biotechnology).

2. Results

As shown in FIG. 20A, gp64 is detected in all the samples studied. In panel B, the SNA lectin which recognises very specifically α2,6 bound sialic acids bound to gp64 uniquely when it is produced with a virus that co-expresses ST6 (see Example 19) but does not bind to the gp64 which is produced during infection with a virus which co-expresses ST3.

FIG. 20C, shows on the other hand that the lectin di-CBM40 indeed recognises the gp64 that was produced during infection with the virus producing ST3. There is no marking of mannosylated gp64 either which is produced when the cells are infected with a wild virus. A weaker but clear marking of gp64 having α2,6 bound sialic acids will however be noticed.

These experiments clearly demonstrate that the virus BACSia3 is capable of complementing Sf9 cells to be able to produce α2,3 sialylated glycoproteins.

Example 19: Use of BacMid-Sia6

1. Construction of a Recombinant Baculovirus Expressing a Recombinant Alpha 2,6 Sialylated Protein.

The activity of BacSia6 was controlled using as model protein Glycoprotein G Vesicular Stomatitis virus, VSVg, the protein X and glycoprotein gp64 of the baculovirus.

Generation and cloning of the recombinant baculoviruses.

The DNAc fragment encoding the protein of interest was cloned in pVTPH according to the general principle described in FIG. 19A. The Sf9 cells were transfected by lipofection with loaded pVTPH, modified pVT/gp37 and DNA of Bacmid2 (control) or the BacMid-Sia6 obtained in example 13. After 7 days of infection at 28° C., the viruses secreted in the culture supernatant were cloned by the phage plaque assay technique. Four viral clones were selected, amplified and their genome extracted to be analysed by Southern blot. The genes inserted into the viral genome were amplified by PCR then sequenced.

Production of recombinant proteins

The proteins were produced as described in example 18.

Analysis of glycosylation by lectin blot.

The presence of recombinant proteins was controlled by Western blot. After transfer of the proteins, the nitrocellulose membranes were incubated in the presence of different specific antibodies, anti-VSVg (mice monoclonal antibodies peroxidase conjugated, reference A5977, Sigma), anti-gp64 (mice monoclonal antibodies AcV5 reference SC65499, Santa Cruz Biotechnology). Revelation was carried out either directly as described in example 16 when the antibody is directly peroxidase conjugated or after incubation with a secondary antibody peroxidase conjugated (rabbit anti-mouse IgG serum peroxidase conjugated, reference A9044). The peroxidase was revealed by chemiluminescence with the ECL SuperSignal® West Pico Chemiluminescent Substrate system (reference 34077, Thermo Scientific).

The lectin that was used in this example was SNA (*Sambucus nigra* agglutinin) which recognises α2,6 bound sialic acids. SNA was revealed as described in example 17.

2. Results a. Glycosylation of Protein X Expressed by the Recombinant Baculovirus Generated from BacSia6

As shown by Western lot, FIG. 21A, when protein X was produced with a recombinant virus derived from BacMid2, its size is clearly less than that of the commercially available protein which was produced by mammal cells, here the CHO cell (compare Wells 1 and 3). Conversely, when it was produced with a recombinant baculovirus derived from BacSia6, protein X had a size comparable to that which was produced in CHO cells (compare Well 2 and Well 3).

Analysis by lectin Blot, FIG. 21B, confirmed the presence of α2,6 bound sialic acids on this protein when it was produced with a recombinant baculovirus derived from BacSia6 (Well 2). Protein X was indeed recognised by SNA (revelation protocol described in example 17), thus explaining the increase in the molecular weight of protein X. This experiment also showed the absence of such a motif on the commercially available protein which was produced in CHO cells (Well 3), in fact the CHO line expresses uniquely a α2,3 sialyltransferase. Thus, as shown in FIG. 21C, protein X expressed in CHO (Well 3) was recognised by MAA (revelation protocol described in example 17) which is specific to α2,3 bound sialic acids, which is not the case of the protein which was expressed with the recombinant baculovirus derived from tBacSia6 (Well 2).

b. Glycosylation of VSVg Expressed by the Recombinant Baculovirus Generated from BacSia6.

VSVg being a membranal protein, we analysed the pellets of the infected cells. As shown in FIG. 22A (Wells 2 and 3), the protein VSVg was produced after infection of Sf9 cells with the 2 recombinant viruses whether they were derived from BacMid2 or BacSia6.

Conversely, analysis by lectin blot with SNA (revelation protocol described in example 17) showed an intense marking of protein VSVg uniquely when it is expressed from the baculovirus derived from BacSia6 (FIG. 22B, Well 2). With protein VSVg produced after infection with the baculovirus derived from BacMid2 a non-specific marking (FIG. 22B, Well 3) only was noted. The "positive control" protein which is supplied with the glycan differentiation kit (Dig Glycan Differentiation Kit), fetuin, was very well marked by SNA (FIG. 22B, Well 1).

c. Glycosylation of Gp64 of the Recombinant Baculovirus Generated from BacSia6.

We also verified that the recombinant virus expressing sialylated VSVg (see above) was also bearing a sialylated gp64. To do so, the baculoviruses secreted in the culture supernatant were sedimented (35,000 rpm for 60 minutes, Beckman Optima LE-80K centrifuge, TI-70-1 rotor) then taken up by a lysis buffer to be analysed by Western blot then lectin blot. As previously, fetuin was used as positive marker for SNA (FIG. 22C and FIG. 22D, Well 1).

FIG. 22C clearly shows the presence of gp64 in Wells 2 and 3. Like what we observed with VSVg, gp64 which was produced after infection with the virus derived from BacSia6 (Well 2) is the only one that is recognised by SNA (revelation protocol described in example 17) (FIG. 22D) thus confirming that gp64 is α2,6 sialylated. The presence of non-specific markings in Wells 2 and 3 (identical marking in both Wells) will also be noted.

These experiments clearly demonstrate that the BacSia6 virus is capable of complementing Sf9 cells to be able produce α2,6 sialylated glycoproteins.

Example 20: BacMid Sia6-II Virus

We analysed the genome of BacMidSia6II by Southern blot to control its genomic organisation.

As shown in FIG. 19B, the restriction profile and the hybridisation profile are compliant with the expected result. The gene of ST6 is thus well integrated in locus pif1.

Example 21: Use of BacMid Sia3/6

1. Construction of a Recombinant Baculovirus Expressing a Recombinant Alpha 2,3 and Alpha 2,6 Sialylated Protein.

The activity of BacSia3-6 was controlled using as model protein the surface glycoprotein of the virus, gp64. To do so, a recombinant virus was obtained by homologous recombination between BacMidSia3/6 and the empty transfer vectors pVTPH and pVT/gp37. The presence of α2,3 sialyl- and α2,6 sialyl-motifs was analysed by lectin blot carried out in the presence of lectin di-CBM40 which recognises α2,3 sialic acids and to a lesser extent α2,6 bound sialic acids and SNA which only recognises α2,6 bound sialic acids and not those which are a2,3 bound.

Generation and cloning of recombinant baculoviruses.

Sf9 cells were transfected by lipofection with empty pVTPH and pVT/gp37 and DNA of Bacmid2 (control) or BacMid-Sia3/6 obtained in example 15. After 7 days of infection at 28° C., the viruses secreted in the culture supernatant were cloned by the phage plaque assay technique. Four viral clones were selected, amplified and their genome extracted to be analysed by Southern blot. The gene inserted in the viral genome was amplified by PCR then sequenced.

Production of recombinant proteins

The proteins were produced as described in example 17.

Analysis of glycosylation by lectin blot

The analysis protocols were identical to those described in Examples 20, 21 and 22.

2. Results

The gp64 produced by the GalSia3-6 virus is the only one which is recognised both by SNA (FIG. 20B) and by di-CBM40 (FIG. 20C), which clearly demonstrates that the 2 types of sialic acids are bound to gp64.

These experiments clearly demonstrate that the BacSia3-6 virus is capable of complementing Sf9 cells to be able to produce a2,3 and a2,6 sialylated glycoproteins.

REFERENCES

Patents

WO 01/12829
WO 2013/005194

BIBLIOGRAPHIC REFERENCES

Palmberger D, Wilson I B, Berger I, Grabherr R, Rendic D. SweetBac: a new approach for the production of mammalianised glycoproteins in insect cells. PLoS One. 2012; 7(4):e34226.

Chang G D, Chen C J, Lin C Y, Chen H C, Chen H. Improvement of glycosylation in insect cells with mammalian glycosyltransferases. J Biotechnol. 2003 Apr. 10; 102(1):61-71.

Possee R D, Hitchman R B, Richards K S, Mann S G, Siaterli E, Nixon C P, Irving H, Assenberg R, Alderton D, Owens R J, King L A. Generation of baculovirus vectors for the high-throughput production of proteins in insect cells. Biotechnol Bioeng. 2008 Dec. 15; 101(6):1115-22.

Tan J, D'Agostaro A F, Bendiak B, Reck F, Sarkar M, Squire J A, Leong P, Schachter H. The human UDP-N-acetylglucosamine: alpha-6-D-mannoside-beta-1,2-N-acetylglucosaminyltransferase II gene (MGAT2). Cloning of genomic DNA, localization to chromosome 14q21, expression in insect cells and purification of the recombinant protein. Eur J Biochem. 1995 Jul. 15; 231(2):317-28.

D'Agostaro G, Bendiak B, Tropak M. Cloning of cDNA encoding the membrane-bound form of bovine beta 1,4-galactosyltransferase. Eur J Biochem. 1989 Jul. 15; 183 (1):211-7.

Münster A K, Eckhardt M, Potvin B, Mühlenhoff M, Stanley P, Gerardy-Schahn R. Mammalian cytidine 5'-monophosphate N-acetylneuraminic acid synthetase: a nuclear protein with evolutionarily conserved structural motifs. Proc Natl Acad Sci USA. 1998 Aug. 4; 95(16):9140-5.

Lawrence S M, Huddleston K A, Pitts L R, Nguyen N, Lee Y C, Vann W F, Coleman T A, Betenbaugh M J. Cloning and expression of the human N-acetylneuraminic acid phosphate synthase gene with 2-keto-3-deoxy-D-glycero-D-galacto-nononic acid biosynthetic ability. J Biol Chem. 2000 Jun. 9; 275(23):17869-77.

Kitagawa H, Paulson J C. Cloning of a novel alpha 2,3-sialyltransferase that sialylates glycoprotein and glycolipid carbohydrate groups. J Biol Chem. 1994 Jan. 14; 269(2):1394-401.

Grundmann U, Nerlich C, Rein T, Zettimeissl G. Complete cDNA sequence encoding human beta-galactoside alpha-2,6-sialyltransferase. Nucleic Acids Res. 1990 Feb. 11; 18(3):667.

Cieplik M, Klenk H D, Garten W. Identification and characterization of *Spodoptera frugiperda* furin: a thermostable subtilisin-like endopeptidase. Biol Chem. 1998 December; 379(12):1433-40.

Juliant S, Lévêque M, Cérutti P, Ozil A, Choblet S, Violet M L, Slomianny M C, Harduin-Lepers A, Cérutti M. Engineering the baculovirus genome to produce galactosylated antibodies in lepidopteran cells. Methods Mol Biol. 2013; 988:59-77.

Jarvis D L, Finn E E. Biochemical analysis of the N-glycosylation pathway in baculovirus-infected lepidopteran insect cells. Virology. 1995 Oct. 1; 212(2):500-11.

Ribeiro J P, Pau W, Pifferi C, Renaudet O, Varrot A, Mahal L K, Imberty A. Characterization of a high-affinity sialic acid-specific CBM40 from *Clostridium perfringens* and engineering of a divalent form. Biochem J. 2016 Jul. 15; 473(14):2109-18

The invention claimed is:

1. A method for producing a recombinant baculovirus of which the genome comprises: one or more transgene(s) each encoding a protein maturation enzyme, and n transgenes each encoding a polypeptide of interest to be expressed at a different locus, said method comprising the steps of:
   a) preparing, in an insect cell, a recombinant baculovirus genome capable of replicating which comprises said one or more transgene(s), each encoding a protein maturation enzyme, and said n transgenes each encoding a polypeptide of interest, by homologous recombination between:
      a1) a replication deficient baculovirus genome in which n genes essential for viral replication located in different regions of the viral genome are non-functional and which comprises said one or more transgene(s), each encoding a protein maturation enzyme, and
      a2) n transfer vectors each comprising:
         i) a nucleotide sequence enabling to restore the function of one of the n non-functional genes essential for viral replication located in different regions of the viral genome,
         ii) one of said n transgenes encoding a polypeptide of interest, each polypeptide of interest to be expressed at a different locus,
         the set of nucleotide sequences i) of the n transfer vectors being capable of restoring the replication of the replication deficient baculovirus genome,
         n being an integer at least equal to 2; and
   b) generating a recombinant baculovirus in an insect cell which comprises the recombinant baculovirus genome obtained at step a),
   wherein said homologous recombination between the replication deficient baculovirus genome and the n transfer vectors takes place in a single transfection step in the insect cell.

2. The method according to claim 1, wherein said replication deficient baculovirus genome of step a1) is prepared, in a bacterial cell, by homologous recombination between:
   a replication deficient baculovirus genome in which n genes essential for viral replication are non-functional, and
   one or more nucleotide sequence(s) each comprising one or more transgene(s) each encoding a protein maturation enzyme.

3. The method according to claim 1, wherein the genes essential for viral replication are selected from the group consisting of: 1629 (ORF9), Pk1 (ORF10), lef-1 (ORF14), ORF34, lef-11 (ORF37), p47 (ORF40), lef8 (ORF50), DNAJ domain (ORF51), ORF53, vp1054 (ORF54), Lef-9 (ORF62), DNA Pol (ORF65), lef-3 (ORF67), ORF73, ORF75, ORF81, p95 (ORF83), vp39 (ORF89), lef-4 (ORF90), p33 (ORF92), helicase (ORF95), vp80 (ORF104), ORF106-107, odv-ec43 (ORF109), gp64/67 (ORF128), ORF132, ORF133, odv-ec27 (ORF144), ORF146, ie1 (ORF147), and lef-2 (ORF6).

4. The method according to claim 1, wherein the n non-functional genes essential for viral replication are each adjacent to a gene not essential for viral replication.

5. The method according to claim 4, wherein the gene not essential for viral replication is selected from the group consisting of: Ph (ORF 8), ORF11, ORF13, egt (ORF15), v-ubiquitin (ORF16), 39K (ORF36), ORF38, p43 (ORF39), lef-12 (ORF41), pcna (ORF49), ORF52, ORF55, Fp (ORF61), ORF63, gp37 (ORF64), ORF68, ORF72, ORF74, ORF82, cg30 (ORF88), ORF91, pif-4 (ORF96), he65 (ORF105), ORF108, ORF110, cathepsin (ORF127), p24 (ORF129), pp34 (ORF131), ORF134, ORF145, odv-e56 (ORF148), and ORF5.

6. The method according to claim 1, wherein the n transgenes encoding a polypeptide each recombine at the locus of a gene not essential for viral replication adjacent to a non-functional gene essential for viral replication.

7. The method according to claim 1, wherein the protein maturation enzyme is selected from the group consisting of: a signal peptidase, a furin, a proprotein convertase, a glycosyltransferase, a glycosidase, a chaperone protein, an isomerase disulphide, an acyltransferase, a methyltransferase, a hydroxylase, a transglutaminase, a farnesyltransferase, a geranylgeranyl-transferase, a N-myristoyltransferase, a palmityltransferase, a phosphatase, a transpeptidase, a carboxylase, and a ubiquitin ligase.

8. The method according to claim 2, wherein the one or more transgene(s), each encoding a protein maturation enzyme, each recombines at the locus of a gene not essential for viral replication.

9. The method according to claim 8, wherein the gene not essential for viral replication is selected from the group consisting of: ptp (ORF1), ctx (ORF3), ORF4, ORF7, odv-e26 (ORF16), ORF17, ORF18, ORF19, ARIF-1 ORF20-21, pif2 (ORF22), protein F (ORF23), iap1 (ORF27), lef6 (ORF28), ORF29, ORF30, sod (ORF31), fgf (ORF32), gta (ORF42), ORF43, ORF44, ORF45, odv-e66 (ORF46), ORF47, ORF56, ORF57, chaB-like (ORF58/59), chaB-like (ORF60), mtase (ORF69), hcf-1 (ORF70), iap2 (ORF71), ORF86, ORF87, ORF111, ORF114, pif3 (ORF115), ORF116, ORF117, pif1 (ORF119), ORF120, ORF121, ORF122, pk2 (ORF123), ORF124, lef7 (ORF125), chitinase (ORF126), gp16 (ORF130), p35 (ORF135), p26 (ORF136), p10 (ORF137), p74 (ORF138), ORF149, ORF150, ie2 (ORF151), pe38 (ORF153) and ORF154.

10. The method according to claim 1, wherein the insect cell is selected from the group consisting of: Sf9, Sf21, Tn5-b14, lepidoptera cell lines sensitive to the baculovirus AcMNPV.

11. The method according to claim 2, wherein the bacterial cell is E. coli selected from DH10B and EL350.

12. The method according to claim 1, wherein the replication deficient baculovirus genome is obtained from a baculovirus genome selected from or derived from the genome of one of the following baculovirus: BmNPV, AcMNPV, ApNPV, BsSNPV, CfMNPV, EoSNPV, HaNPV, HzNPV, LdMNPV, MbMNPV, OpMNPV, SlMNPV, SeMNPV and TeNPV.

13. The method according to claim 1, wherein n is an integer ranging from 2 to 31.

14. A recombinant baculovirus or recombinant baculovirus genome, susceptible to be obtained by the production method according to claim 1, comprising:
   a) One or more transgene(s) each encoding a protein maturation enzyme, and
   b) n nucleotide sequences of formula (I):

[transgene encoding a polypeptide of interest]–
   [spacer nucleotide sequence]–[gene essential for
   functional viral replication]         (I), said spacer nucleic acid sequence being constituted of 0 to 600 base pairs,
   said gene essential for functional viral replication being selected from the group consisting of: 1629 (ORF9), Pk1 (ORF10), lef-1 (ORF14), ORF34, lef-11 (ORF37), p47 (ORF40), lef8 (ORF50), DNAJ domain (ORF51), ORF53, vp1054 (ORF54), Lef-9 (ORF62), DNA Pol (ORF65), lef-3 (ORF67), ORF73, ORF75, ORF81, p95 (ORF83), vp39 (ORF89), lef-4 (ORF90), p33 (ORF92), helicase (ORF95), Vp80 (ORF104), ORF106-107, odv-ec43 (ORF109), gp64/67 (ORF128), ORF132, ORF133, odv-ec27 (ORF144), ORF146, ie1 (ORF147), and lef-2 (ORF6); and n being an integer at least equal to 2.

15. The recombinant baculovirus or recombinant baculovirus genome according to claim 14, wherein said recombinant baculovirus or recombinant baculovirus genome do not comprise n genes not essential for viral replication chosen from the group consisting of: Ph (ORF 8), ORF11, ORF13, egt (ORF15), v-ubiquitin (ORF35), 39K (ORF36), ORF38, p43 (ORF39), lef-12 (ORF41), pcna (ORF49), ORF52, ORF55, Fp (ORF61), ORF63, gp37 (ORF64), ORF68, ORF72, ORF74, ORF82, cg30 (ORF88), ORF91, pif-4 (ORF96), he65 (ORF105), ORF108, ORF110, cathepsin (ORF127), p24 (ORF129), pp34 (ORF131), ORF134, ORF145, odv-e56 (ORF148), and ORF5.

16. A set of homologous recombination elements comprising:
    a) a replication deficient baculovirus genome in which n genes essential for viral replication located in different regions of the viral genome are non-functional and which comprises one or more transgene(s) each encoding a protein maturation enzyme;
    b) n transfer vectors each comprising:
       i) a nucleic acid sequence enabling to restore the function of one of the n non-functional genes essential for viral replication,
       ii) a transgene encoding a polypeptide of interest, each polypeptide of interest expressed at a different locus,
    n being an integer at least equal to 2.

17. A cell comprising a recombinant baculovirus or a recombinant baculovirus genome according to claim 14.

18. A process for the production of n polypeptides of interest comprising producing the polypeptides from a recombinant baculovirus or a recombinant baculovirus genome according to claim 14.

19. The method according to claim 10, wherein the insect cell is Sf9.

20. The method according to claim 12, wherein the replication deficient baculovirus genome is obtained from a baculovirus genome selected from or derived from AcMNPV.

21. The method according to claim 13, wherein n is equal to or greater than 3.

22. A cell comprising a set of homologous recombination elements according to claim 16.

23. A process for the production of n polypeptides of interest comprising producing the polypeptides in a cell according to claim 17.

24. The method according to claim 8, wherein the one or more transgene(s), each encoding a protein maturation enzyme each recombine at the locus of a gene not essential for viral replication non-adjacent to a non-functional gene essential for viral replication.

* * * * *